United States Patent
Amin et al.

(10) Patent No.: US 9,422,239 B1
(45) Date of Patent: Aug. 23, 2016

(54) DUAL PPAR-δ PPAR-γ AGONISTS

(71) Applicants: Rajesh Amin, Waverly, AL (US); Tracey Boncher, Rockford, MI (US); Orlando Acevedo, Auburn, AL (US)

(72) Inventors: Rajesh Amin, Waverly, AL (US); Tracey Boncher, Rockford, MI (US); Orlando Acevedo, Auburn, AL (US)

(73) Assignees: Auburn University, Auburn, AL (US); Ferris State University, Big Rapids, MI (US)

( * ) Notice: Subject to any disclaimer, the term of this patent is extended or adjusted under 35 U.S.C. 154(b) by 125 days.

(21) Appl. No.: 14/212,864

(22) Filed: Mar. 14, 2014

Related U.S. Application Data

(60) Provisional application No. 61/783,487, filed on Mar. 14, 2013.

(51) Int. Cl.
| | |
|---|---|
| *A01N 43/38* | (2006.01) |
| *A61K 31/40* | (2006.01) |
| *C07D 209/48* | (2006.01) |
| *C07C 229/38* | (2006.01) |
| *C07C 217/40* | (2006.01) |
| *A61K 31/195* | (2006.01) |
| *A61K 31/4035* | (2006.01) |
| *A61K 31/137* | (2006.01) |

(52) U.S. Cl.
CPC ............ *C07D 209/48* (2013.01); *A61K 31/137* (2013.01); *A61K 31/195* (2013.01); *A61K 31/4035* (2013.01); *C07C 217/40* (2013.01); *C07C 229/38* (2013.01)

(58) Field of Classification Search
None
See application file for complete search history.

(56) References Cited

PUBLICATIONS

Gathiaka et al., Design, development and evaluation of novel dual PPAR delta/PPAR gamma agonists, 2013, Bioorganic & Medicinal Chemistry Letters, 23, pp. 873-879.*
P. Stahl, et al., Handbook of Pharmaceutical Salts: Properties, Selection and Use, (VCHA/Wiley-VCH, 2002) (book reference, not submitted—Applicants will provide a copy if requested).
S.M. Berge, et al., "Pharmaceutical Salts," Journal of Pharmaceutical Sciences, vol. 66, No. 1, Jan. 1977.
Gathiaka et al., "Design, development and evaluation of novel dual PPARδ/PPARγ agonists," *Bioorg Med Chem Lett.*, 2013; 23(3):873-879.
Artis, Dean R., et al. "Scaffold-based discovery of indeglitazar, a PPAR pan-active anti-diabetic agent." *Proceedings of the National Academy of Sciences* 106.1 (2009): 262-267.
Connors, Richard V., et al. "Identification of a PPARδ agonist with partial agonistic activity on PPARγ." *Bioorganic & medicinal chemistry letters* 19.13 (2009): 3550-3554.
Lewis, Stephanie N., Josep Bassaganya-Riera, and David R. Bevan. "Virtual screening as a technique for PPAR modulator discovery." *PPAR research* 2010 (2009).

* cited by examiner

*Primary Examiner* — Kortney L Klinkel
*Assistant Examiner* — Tori M Strong
(74) *Attorney, Agent, or Firm* — Barnes & Thornburg LLP

(57) ABSTRACT

The present disclosure provides novel compounds with activity as PPARβ/δ and PPARγ dual agonists. The disclosure also provides methods of treating diabetes mellitus and methods of treating Alzheimer's disease utilizing the novel compounds, as well as pharmaceutical formulations comprising the novel compounds.

19 Claims, 25 Drawing Sheets

DUAL PPAR-δ PPAR-γ AGONISTS

CROSS-REFERENCE TO RELATED APPLICATIONS

This application claims the benefit under 35 USC §119(e) of U.S. Provisional Application Ser. No. 61/783,487, filed on Mar. 14, 2013, the entire disclosure of which is incorporated herein by reference.

TECHNICAL FIELD

The invention relates to novel compounds that act as dual agonists to PPAR-δ and PPAR-γ. The invention includes compositions, methods, and formulations for the treatment of disease, such as diabetes mellitus or Alzheimer's disease.

BACKGROUND AND SUMMARY OF THE INVENTION

Currently, the prevalence of diabetes mellitus is at an epidemic proportion in the general population and is associated with excessive cardiovascular morbidity and mortality. In particular, both impaired insulin secretion and resistance contribute to the development of the disease, particularly Type 2 diabetes mellitus. The drug class known as thiazolidinediones (TZDs) has been shown to improve whole body insulin sensitivity. The beneficial effects of TZDs are attributed to the activation of the nuclear receptor class of transcription factors known as PPAR (Peroxisomal Proliferator Activating Receptor). The PPAR family of nuclear receptors includes three members (PPARα, PPARβ/δ, and PPARγ) that are highly conserved in mammals, each forming a functional heterodimeric complex with 9-cis retinoic acid receptor (RXR).

However, currently available TZDs are associated with adverse cardiovascular events mostly due to development of peripheral edema and weight gain. For example, a full PPARγ agonist (rosiglitazone) has been shown to increase the risk of adverse cardiovascular events, in part due to the increase in fluid retention. Rosiglitazone is known to bind in the ligand binding domain (AF2 domain) of the PPAR-gamma receptor. This ligand interacts with many amino acids that confer bioactivity, especially His 449 and Tyr 443. It has been determined that Tyr 473 induces the increase in adipocyte maturation, including lipid accumulation and storage. However, strong interaction with this site also has led to unwanted off target effects including increased sodium retention in the kidneys, increased edema, ectopic fat accumulation in the heart, liver and muscle including skeletal muscle and heart. Therefore, the full agonist activity at PPARγ is believed to be associated with the deleterious side effects observed following treatment with TZDs such as rosiglitazone and pioglitazone.

PPARβ/δ activation is associated with improving overall circulating cholesterol levels (HDL, LDL, and triglycerides) and is ubiquitously expressed throughout the body. Furthermore, overexpression of PPARβ/δ in skeletal muscle improves the glycolytic muscle fiber type in animal models and thus improves circulating glucose and fatty acid levels. However, agonists for this class of receptors do not have a significant impact upon improving insulin sensitivity.

Therefore, there exists a need for new compounds such as new TZDs that can effectively treat diabetes mellitus. Because diabetes and metabolic syndrome are associated with defects in glucose oxidation and lipid metabolism, the development of dual agonists that can activate both PPARβ/δ and PPARγ simultaneously is highly desirable. Accordingly, the present disclosure provides novel compounds with activity as PPARβ/δ and PPARγ dual agonists which exhibit desirable properties and provide related advantages for improvement in the treatment of diabetes mellitus.

Furthermore, Alzheimer's disease (AD) is one the fifth leading causes of death amongst people over 65 years and over in the United States, illustrating the limitations of the current therapies to prevent the progression of the disease. Continuous increase in the mortality rates due to AD indicates the critical need for new drug discovery based upon discovery of novel molecular targets for therapeutic potential. In particular, possible novel molecular targets correlations between Type 2 diabetes mellitus and AD have been found to have direct pathological links. Moreover, the epidemic proportions of Type 2 diabetes mellitus highlights the contribution of diabetes to the development of AD. Although there are direct links between AD and diabetes in the manifestation of cognitive impairment, there is a lack of vital knowledge to understanding how impaired insulin signaling directly alters memory in AD.

It is well known that PPARs are centrally involved in regulating whole body insulin sensitivity and may serve as a potential therapeutic target for AD. Pharmacological activation of PPARs has been shown to improve pathologies as well as learning and memory in transgenic AD animal models. However, there exists a need to provide insights into the molecular signaling mechanisms mediated by central (hippocampal) PPAR activation and improved cognition in AD.

Recently, ligand based activation of the nuclear receptor PPARγ has been shown to improve cognition in AD patients and transgenic animal models of AD by attenuating amyloid beta levels and Tau hyperphosphorylation. However, the use of TZDs for AD is limited due to their poor blood-brain barrier (BBB) permeability and undesirable side effects. Pioglitazone (a PPARγ agonist) and rosiglitazone (a full PPARγ agonist) were initially characterized as BBB impermeable, thus requiring high dose treatment over an extended period of time to obtain a significant therapeutic effect. However, long term treatment of high doses of rosiglitazone lead to life threatening side effects in humans. Therefore, there exists a need for development of TZDs with potential application as a treatment for AD. Accordingly, the present disclosure provides novel compounds with activity as PPARβ/δ and PPARγ dual agonists which exhibit desirable properties and provide related advantages for improvement in the treatment of AD.

The present disclosure provides novel compounds with activity as PPARβ/δ and PPARγ dual agonists. The disclosure also provides methods of treating diabetes mellitus and methods of treating Alzheimer's disease utilizing the novel compounds, as well as pharmaceutical formulations comprising the novel compounds.

The novel compounds, pharmaceutical formulations, and methods comprising the novel compounds according to the present disclosure provide several advantages compared to other compositions, formulations, and methods known in the art. First, the novel compounds have strong binding affinity for both PPARγ and PPARβ/δ. Second, the novel compounds demonstrate increased gene expression of mitochondrial markers in skeletal muscle cells, as well as increased mRNA expression levels of advantageous PPARγ targets. Third, the novel compounds have increased BBB permeability, leading to enhanced CNS activity that is essential for potential treatment in Alzheimer's disease. Finally, the novel compounds have not been associated with adverse nonspecific side effects (e.g., ectopic lipid accumulation and hemodynamic effects resulting in increased incidences of myocardial infarctions) that have been observed with other TZDs known in the art.

The following numbered embodiments are contemplated and are non-limiting:

1. A composition comprising a compound selected from the group consisting of

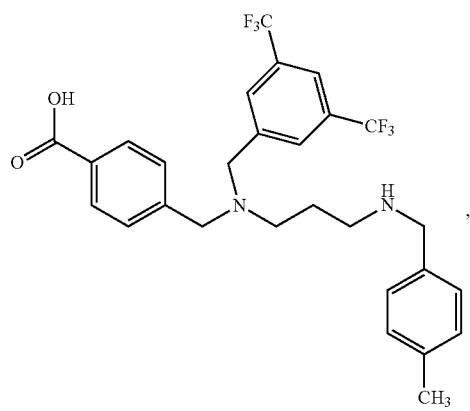

,

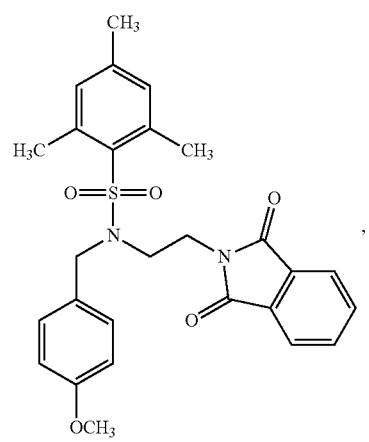

,

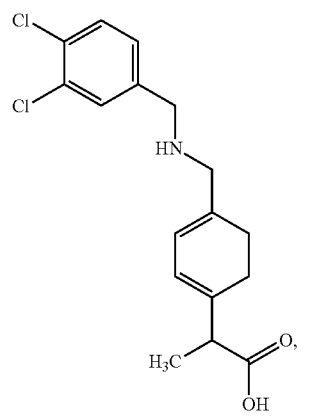

and

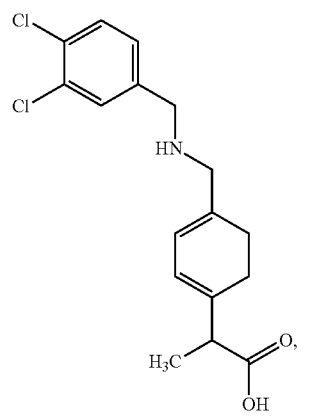

or a pharmaceutically acceptable salt or derivative thereof.

2. A composition comprising a compound of the formula

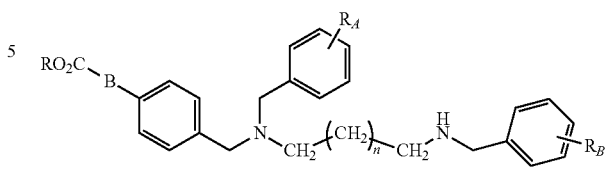

or a pharmaceutically acceptable salt thereof, wherein
B is a bond or $(CH_2)_x$ where x is 1, 2, 3, or 4;
n is 1, 2, or 3;
R is C1-C6 alkyl or hydrogen;
$R_A$ represents from 1 to 4 substituents independently selected in each instance from the group consisting of F and $CF_3$; and
$R_B$ is C1-C6 alkyl, F, Cl, Br, CN, or $CF_3$.

3. A composition comprising a compound selected from the group consisting of

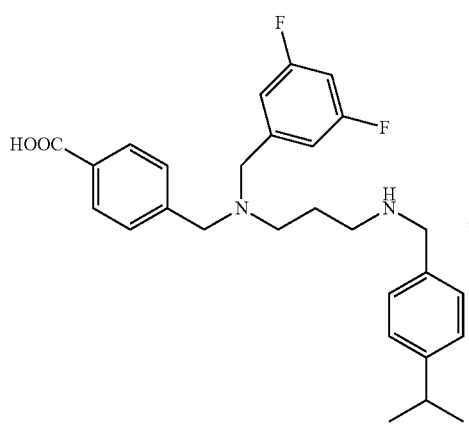

9S

,

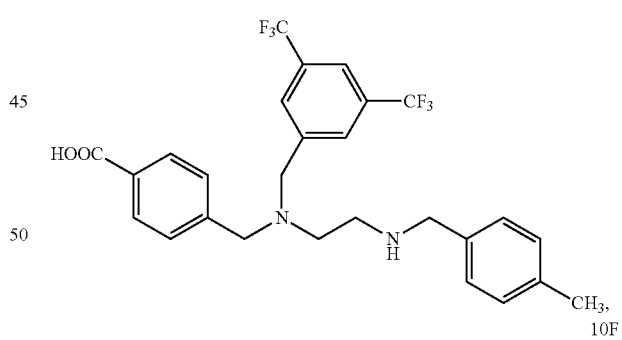

9Q

10F

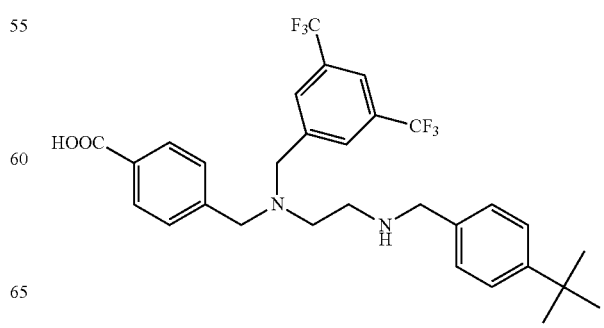

,

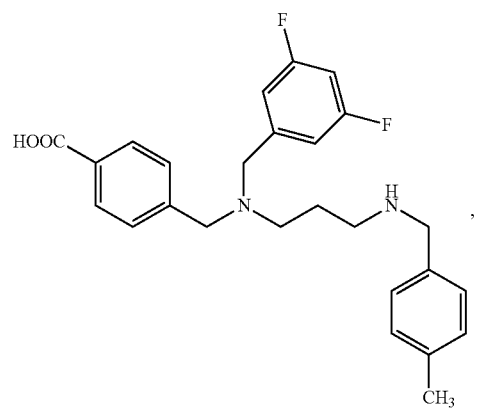
9R
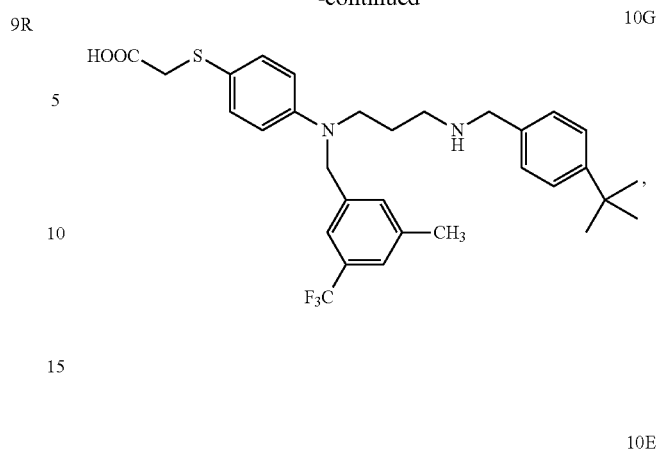
10G
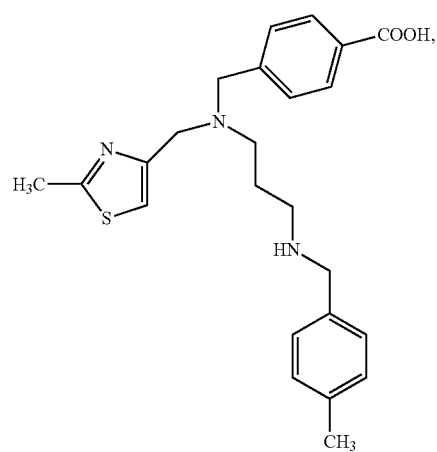
10A
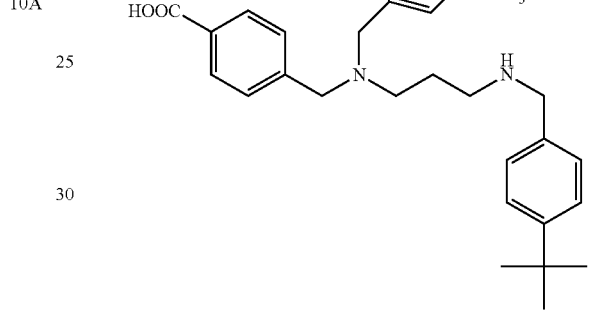
10E
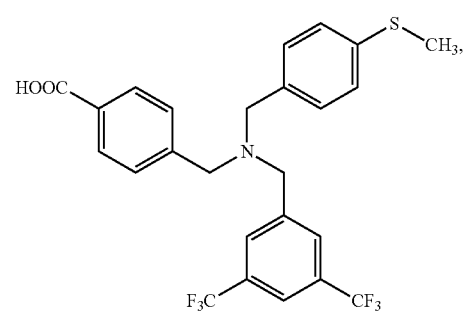
10C
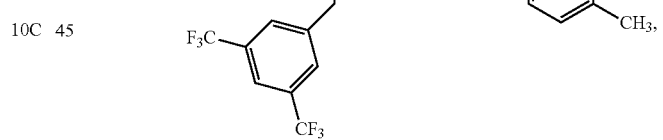
10d
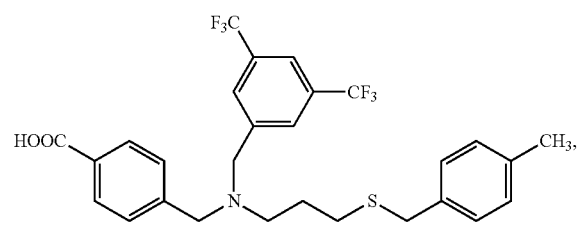
10B
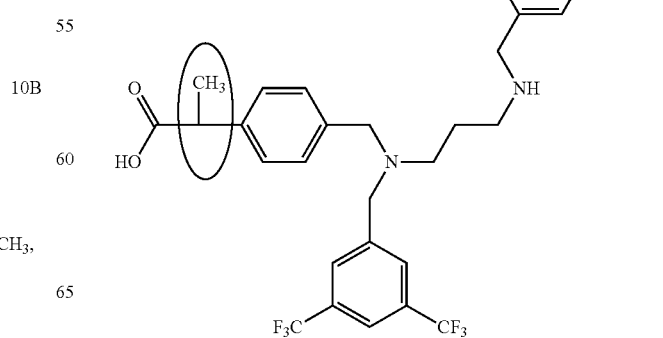
9-b

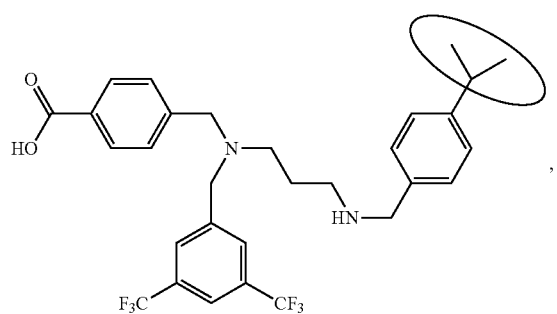
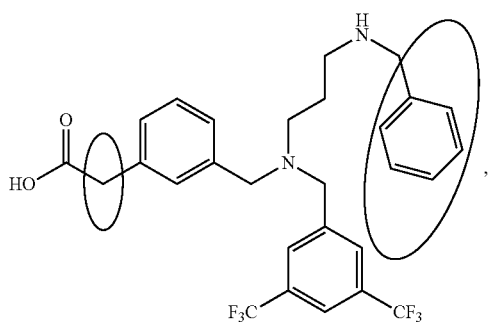
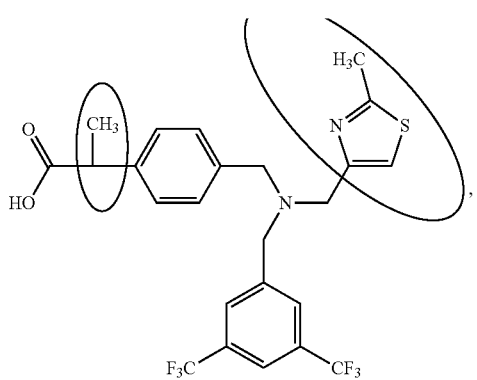
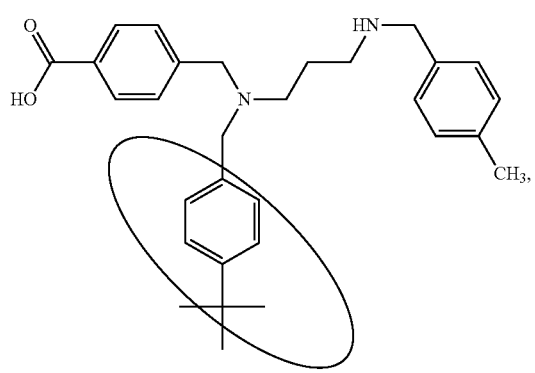
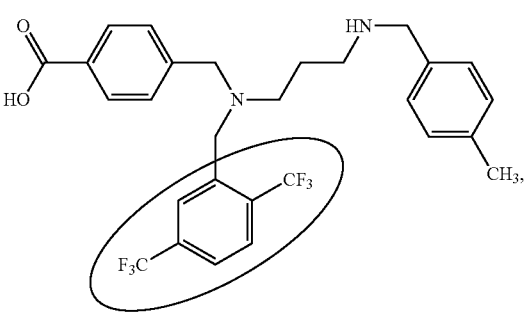

9-k
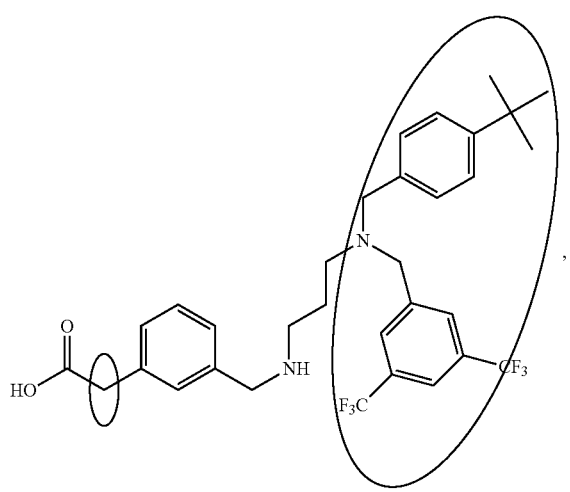
9-L
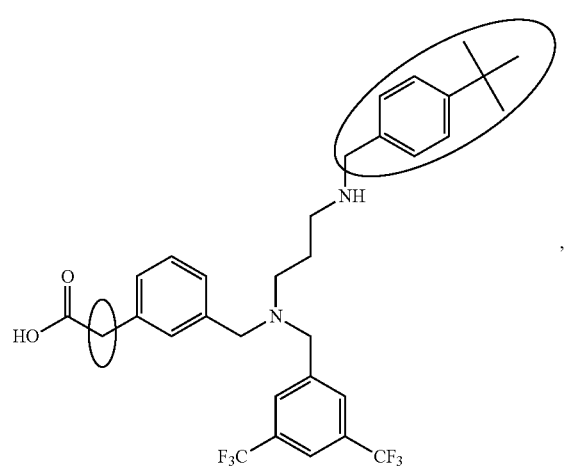
9-M
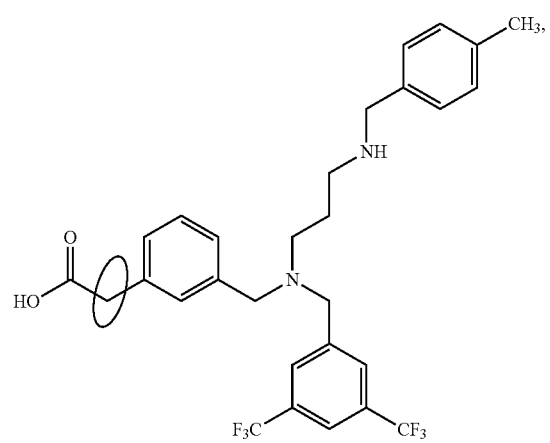
9-t
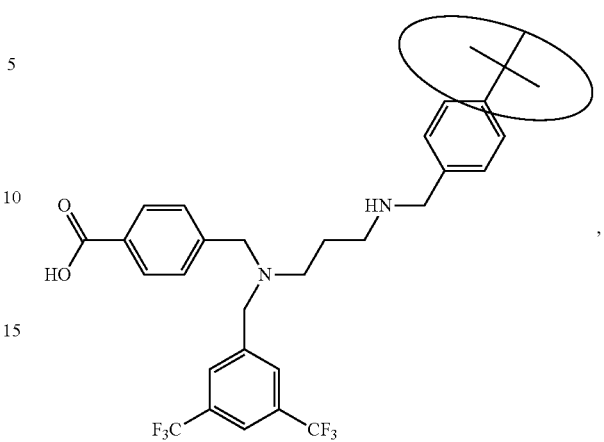
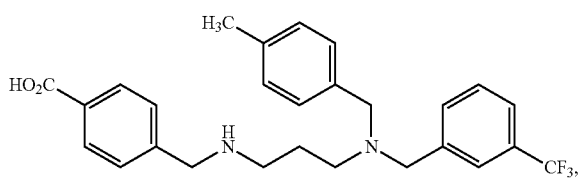
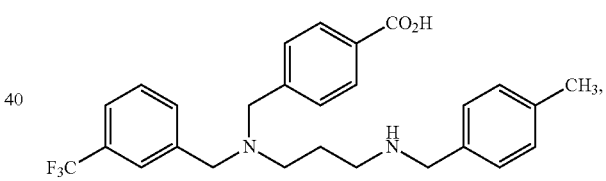
11-D (8-75)
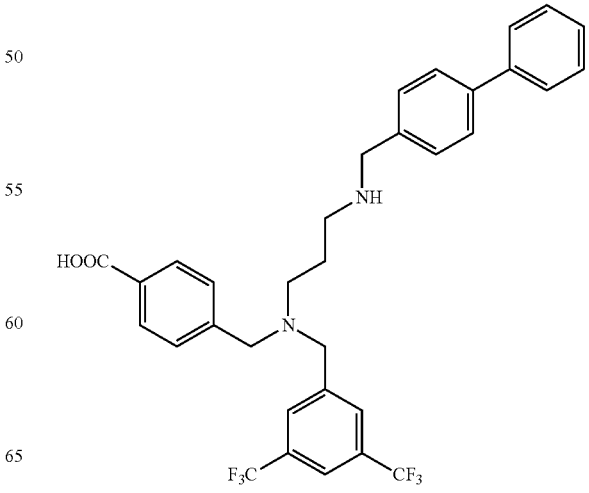

-continued

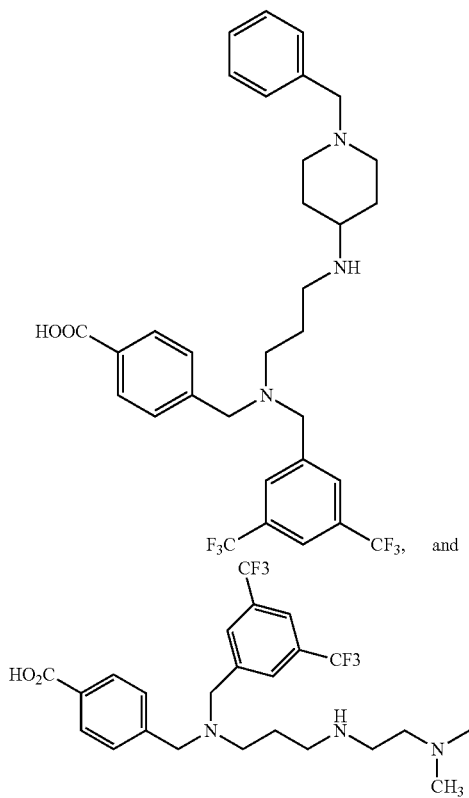

11-b (8-58a)

4. The composition of any of the above clauses, wherein the compound is an agonist of a PPARγ receptor.

5. The composition of any of the above clauses, wherein the compound has a binding affinity for the PPARγ receptor between −10.0 and −12.0 kcal/mol.

6. The composition of any of the above clauses, wherein the compound binds with an amino acid residue of the PPARγ receptor binding pocket, and wherein the amino acid residue is selected from the group consisting of Cys285, Thr288, Thr289, Leu330, Val334, Leu339, Leu353, and Phe368.

7. The composition of any of the above clauses, wherein the binding between the compound and the amino acid residue is a hydrogen bond.

8. The composition of any of the above clauses, wherein the compound is an agonist of a PPARγ receptor.

9. The composition of any of the above clauses, wherein the compound has a binding affinity for the PPARγ receptor between −10.0 and −12.0 kcal/mol.

10. The composition of any of the above clauses, wherein the compound binds with an amino acid residue of the PPARγ receptor binding pocket, and wherein the amino acid residue is selected from the group consisting of Leu228, Cys285, Gln286, Arg288, Ser289, Glu295, Met329, Leu330, Ser342, Glu343, Phe363, and His 449.

11. The composition of any of the above clauses, wherein the binding between the compound and the amino acid residue is a hydrogen bond.

12. The composition of any of the above clauses, wherein the compound is an agonist of PPARδ and an agonist of PPARγ.

13. The composition of any of the above clauses, wherein the compound permeates the blood-brain barrier.

14. A pharmaceutical formulation comprising a therapeutically effective amount of a compound selected from the group consisting of

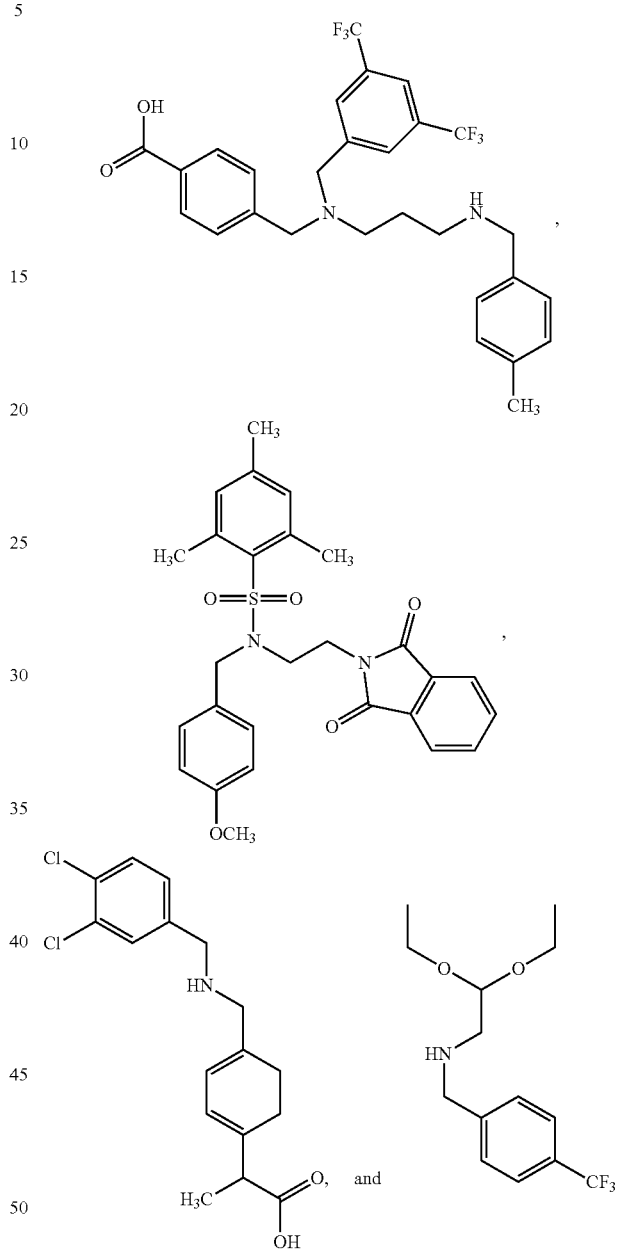

or a pharmaceutically acceptable salt or derivative thereof, and one or more pharmaceutically acceptable carriers.

15. A pharmaceutical formulation comprising a therapeutically effective amount of a compound of the formula

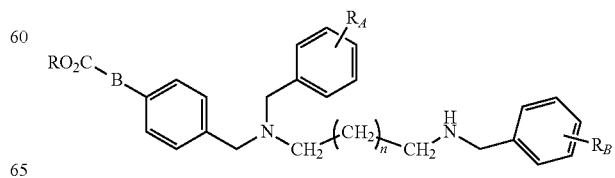

or a pharmaceutically acceptable salt thereof, wherein

B is a bond or $(CH_2)_X$ where x is 1, 2, 3, or 4;

n is 1, 2, or 3;

R is C1-C6 alkyl or hydrogen;

$R_A$ represents from 1 to 4 substituents independently selected in each instance from the group consisting of F and $CF_3$; and $R_B$ is C1-C6 alkyl, F, Cl, Br, CN, or CF, and one or more pharmaceutically acceptable carriers.

16. A pharmaceutical formulation comprising a therapeutically effective amount of a compound selected from the group consisting of

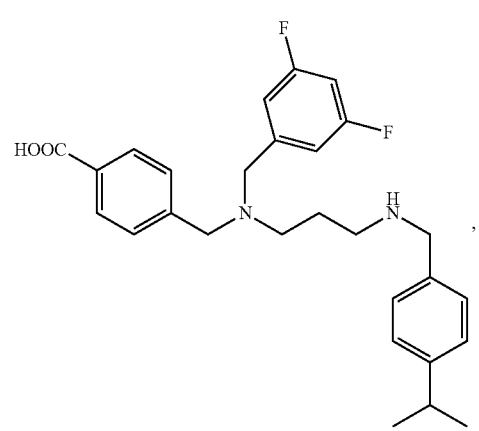
9S

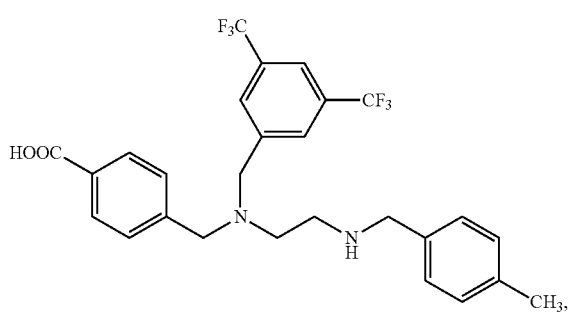
9Q

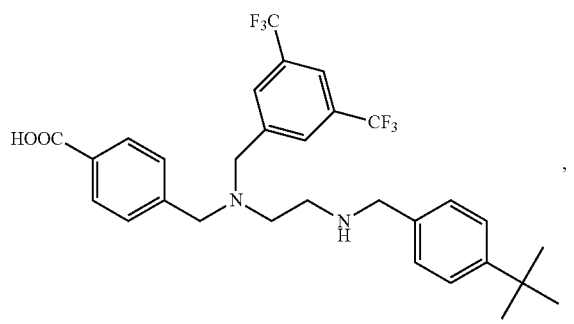
10F

-continued

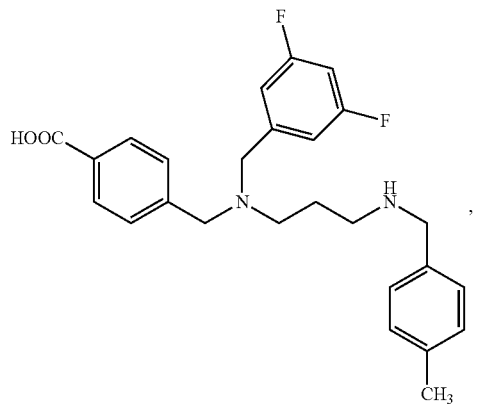
9R

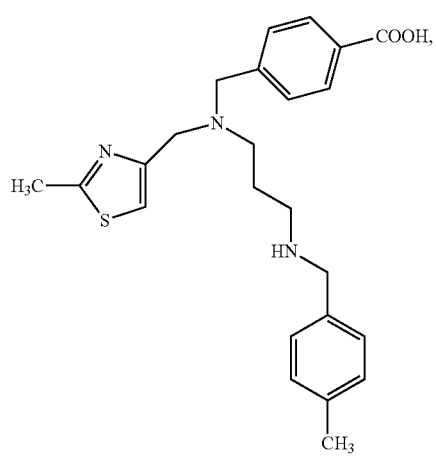
10A

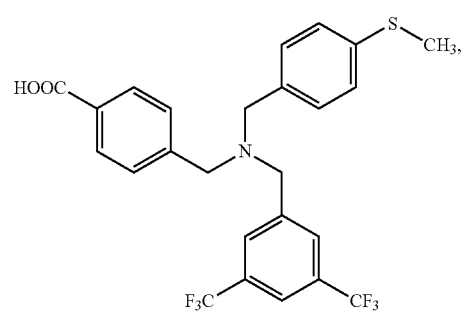
10C

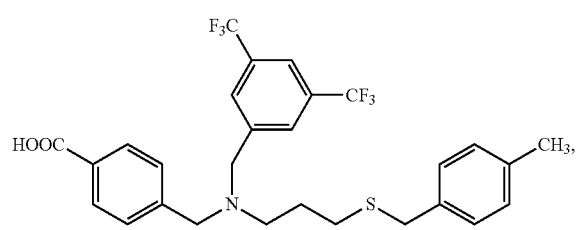
10B

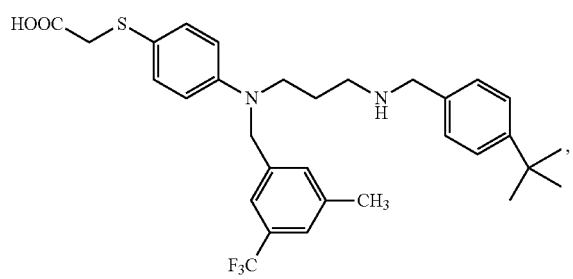
10G
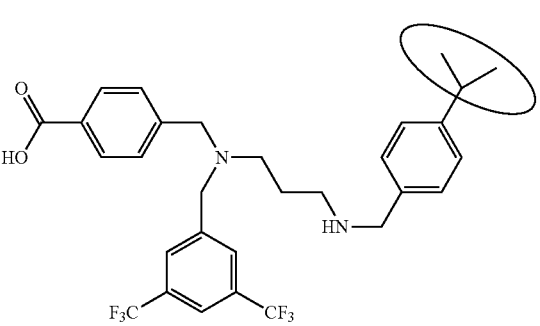
9-C
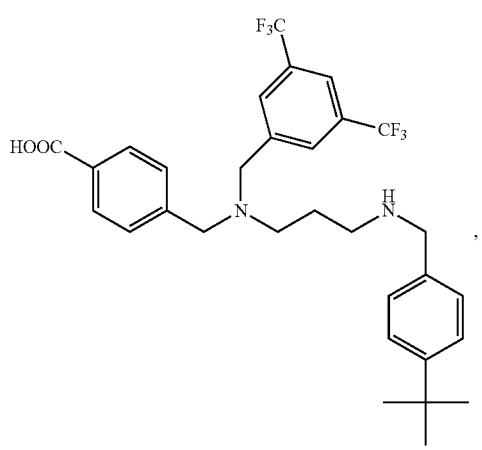
10E
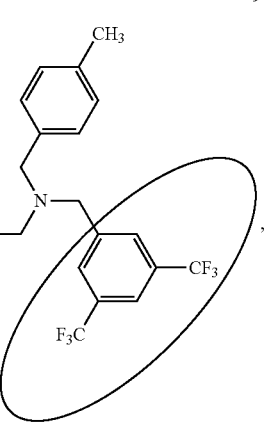
9-d
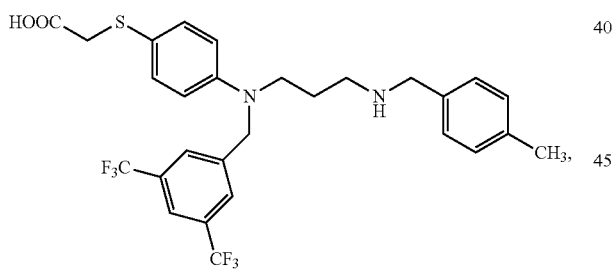
10d
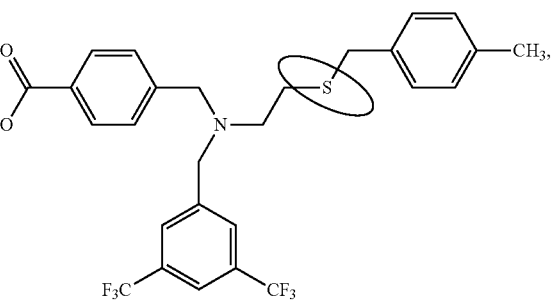
9-e
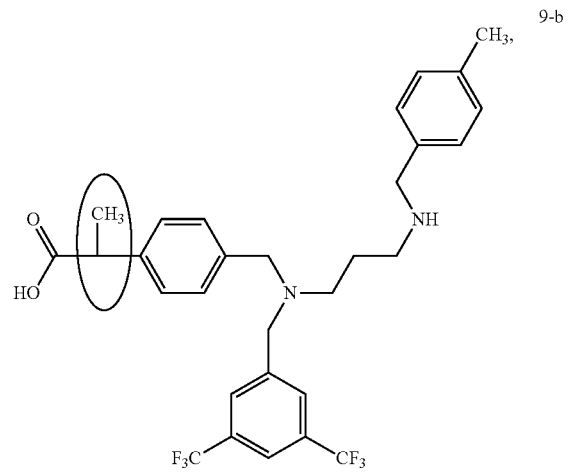
9-b
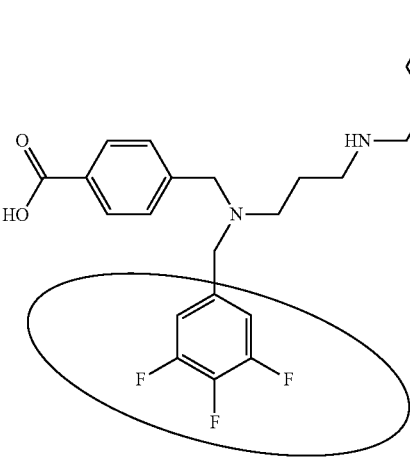
9-f

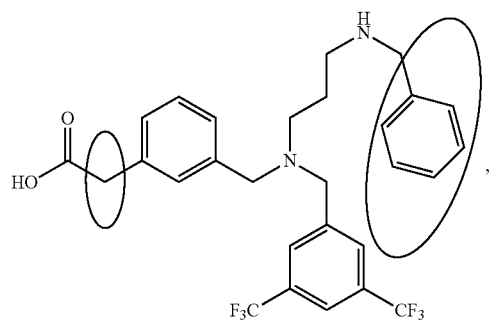
9-g
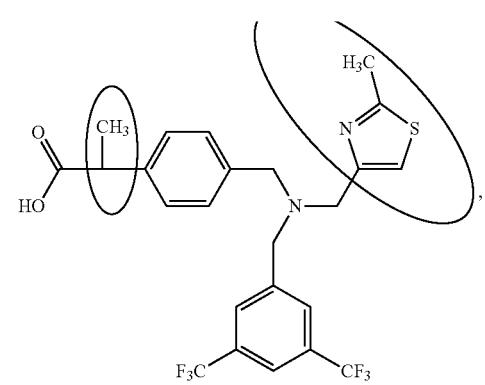
9-h
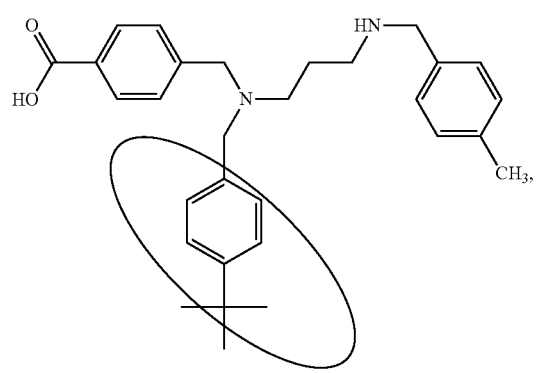
9-i
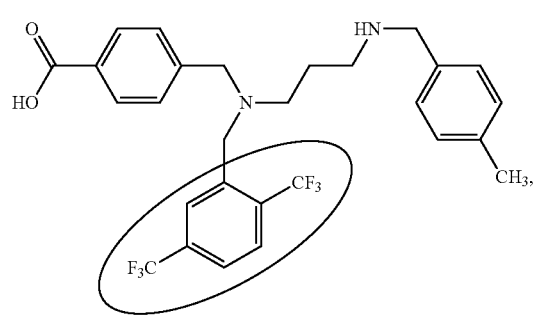
9-j
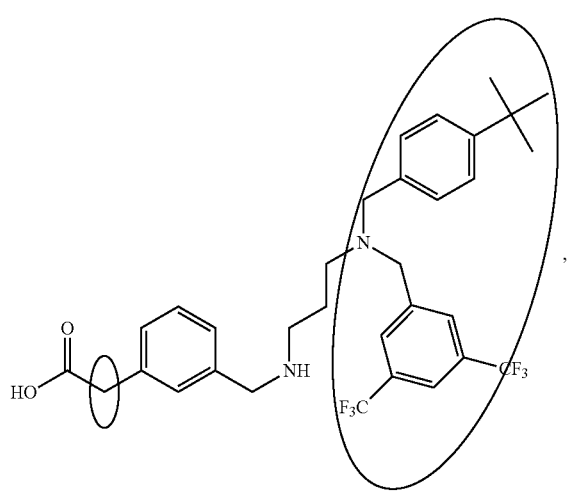
9-k
9-L
9-M 19
-continued

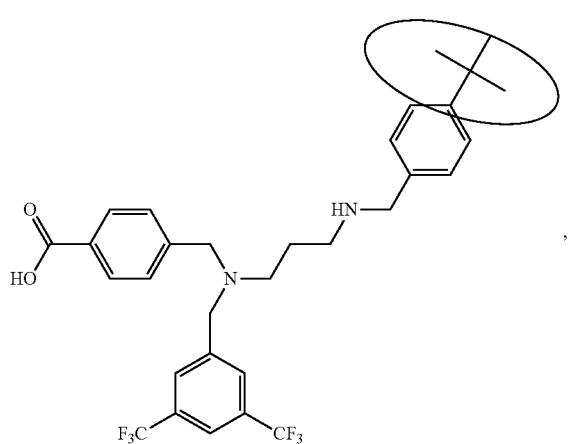
9-t

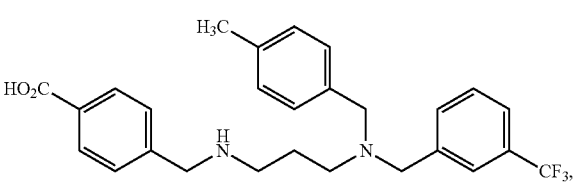

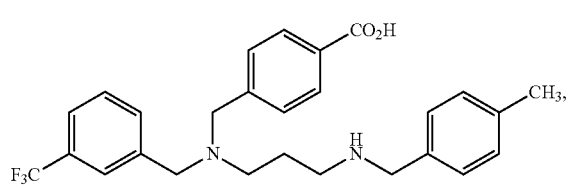

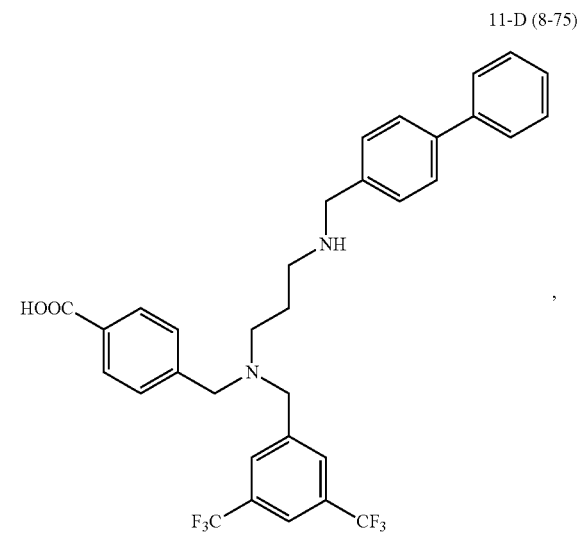
11-D (8-75)

20
-continued

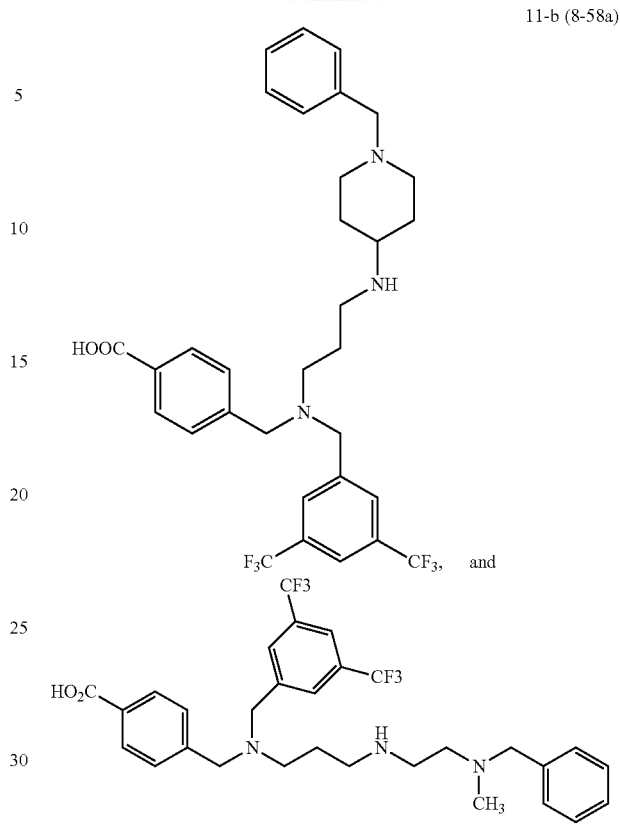
11-b (8-58a)

, and or a pharmaceutically acceptable salt or derivative thereof, and one or more pharmaceutically acceptable carriers.

17. The pharmaceutical formulation of any of the above clauses further comprising at least one additional active ingredient.

18. The pharmaceutical formulation of any of the above clauses, wherein the compound is an agonist of a PPARδ receptor.

19. The pharmaceutical formulation of any of the above clauses, wherein the compound has a binding affinity for the PPARδ receptor between −10.0 and −12.0 kcal/mol.

20. The pharmaceutical formulation of any of the above clauses, wherein the compound binds with an amino acid residue of the PPARδ receptor binding pocket, and wherein the amino acid residue is selected from the group consisting of Cys285, Thr288, Thr289, Leu330, Val334, Leu339, Leu353, and Phe368.

21. The pharmaceutical formulation of any of the above clauses, wherein the binding between the compound and the amino acid residue is a hydrogen bond.

22. The pharmaceutical formulation of any of the above clauses, wherein the compound is an agonist of a PPARγ receptor.

23. The pharmaceutical formulation of any of the above clauses, wherein the compound has a binding affinity for the PPARγ receptor between −10.0 and −12.0 kcal/mol.

24. The pharmaceutical formulation of any of the above clauses, wherein the compound binds with an amino acid residue of the PPARγ receptor binding pocket, and wherein the amino acid residue is selected from the group consisting of Leu228, Cys285, Gln286, Arg288, Ser289, Glu295, Met329, Leu330, Ser342, Glu343, Phe363, and His 449.

25. The pharmaceutical formulation of any of the above clauses, wherein the binding between the compound and the amino acid residue is a hydrogen bond.

26. The pharmaceutical formulation of any of the above clauses, wherein the compound is an agonist of PPARγ and an agonist of PPARγ.

27. The pharmaceutical formulation of any of the above clauses, wherein the compound permeates the blood-brain barrier.

28. A method of treating diabetes mellitus in a patient in need thereof, said method comprising the step of administering a therapeutically effective amount of a composition to the patient, wherein the composition comprises a compound selected from the group consisting of

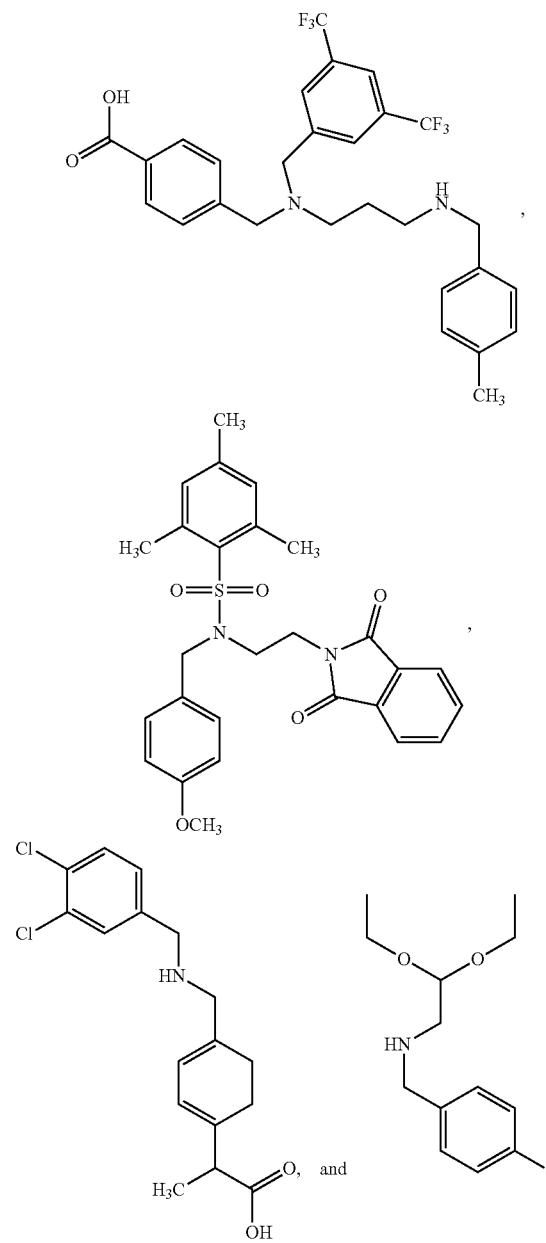

or a pharmaceutically acceptable salt or derivative thereof, and wherein the administration results in improvement of at least one symptom associated with diabetes mellitus in the patient.

29. A method of treating diabetes mellitus in a patient in need thereof, said method comprising the step of administering a therapeutically effective amount of a composition to the patient, wherein the composition comprises a compound of the formula

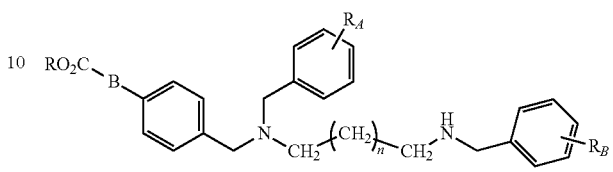

or a pharmaceutically acceptable salt thereof, wherein

B is a bond or $(CH_2)_X$ where x is 1, 2, 3, or 4;

n is 1, 2, or 3;

R is C1-C6 alkyl or hydrogen;

$R_A$ represents from 1 to 4 substituents independently selected in each instance from the group consisting of F and $CF_3$; and $R_B$ is C1-C6 alkyl, F, Cl, Br, CN, or $CF_3$, and wherein the administration results in improvement of at least one symptom associated with diabetes mellitus in the patient.

30. A method of treating diabetes mellitus in a patient in need thereof, said method comprising the step of administering a therapeutically effective amount of a composition to the patient, wherein the composition comprises a compound selected from the group consisting of

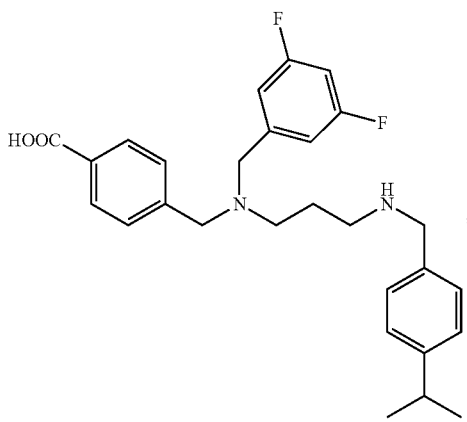

9S

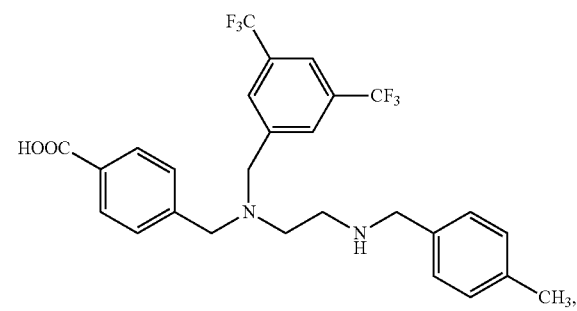

9Q

-continued
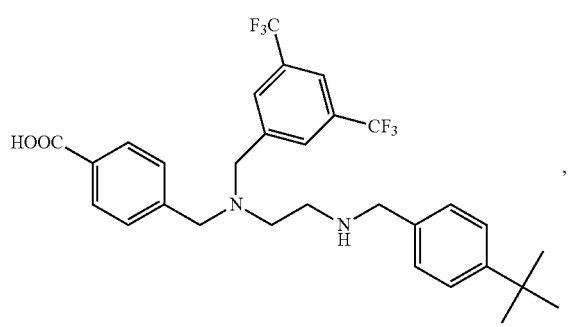
10F
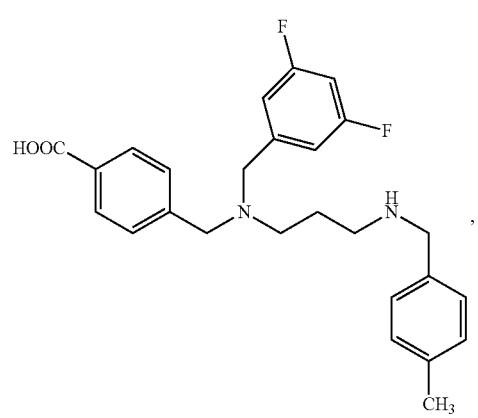
9R
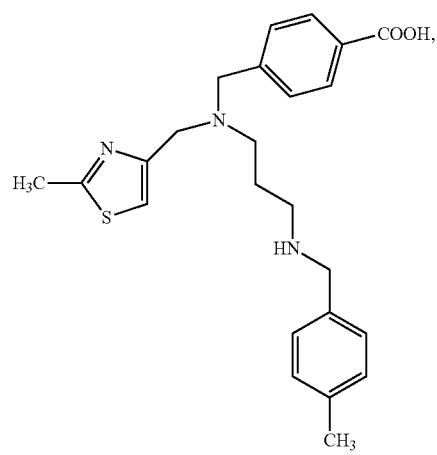
10A
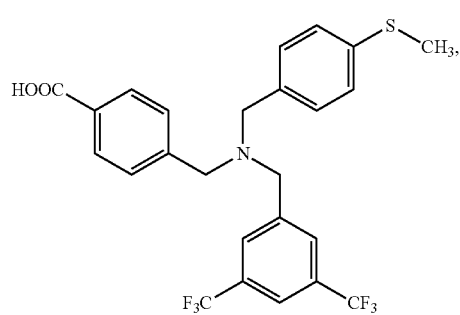
10C
-continued
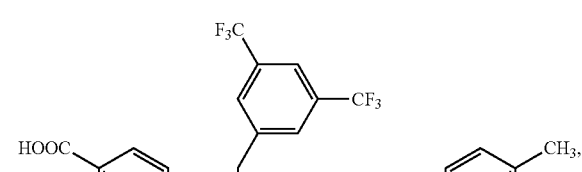
10B
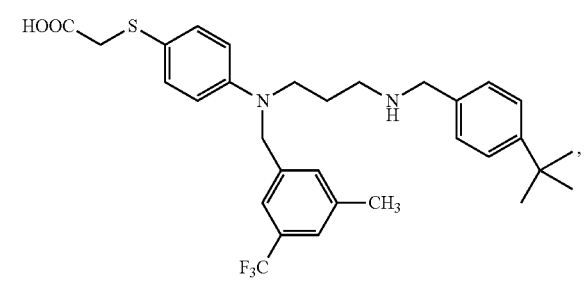
10G
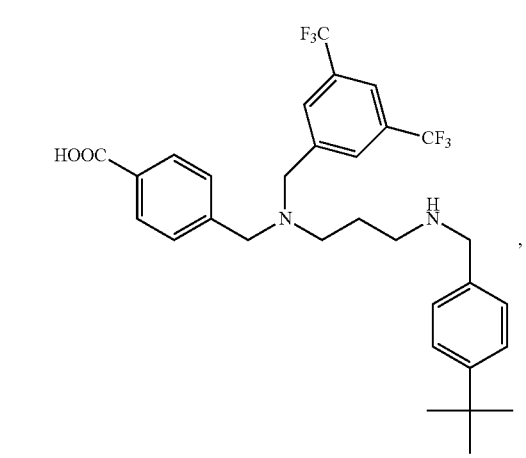
10E
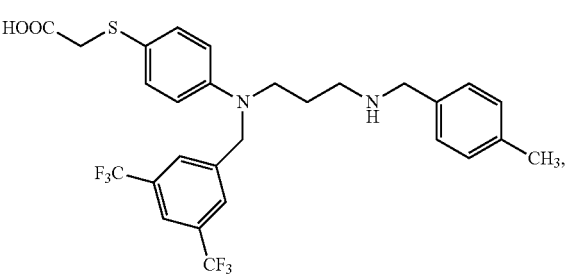
10d

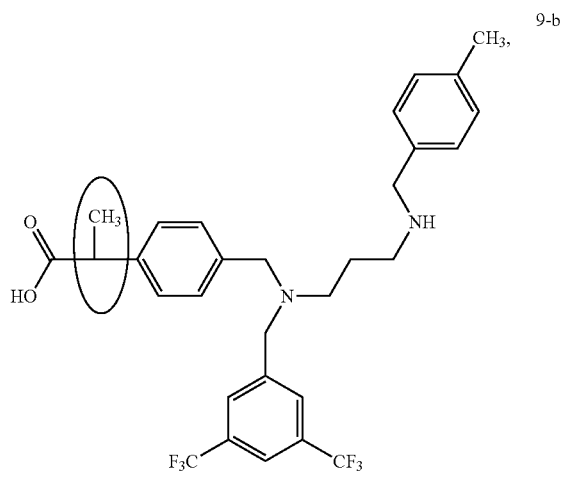
9-b
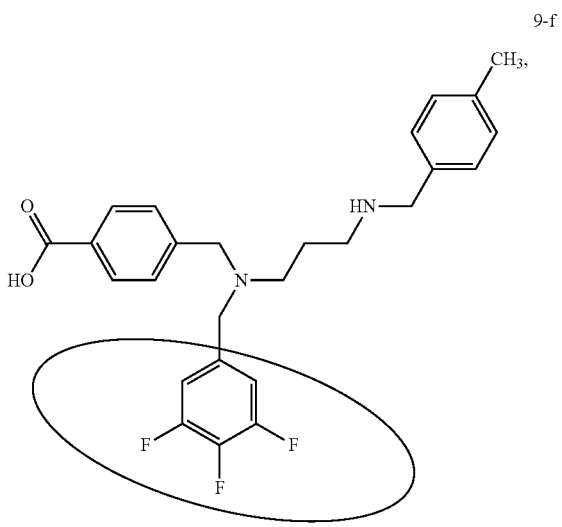
9-f
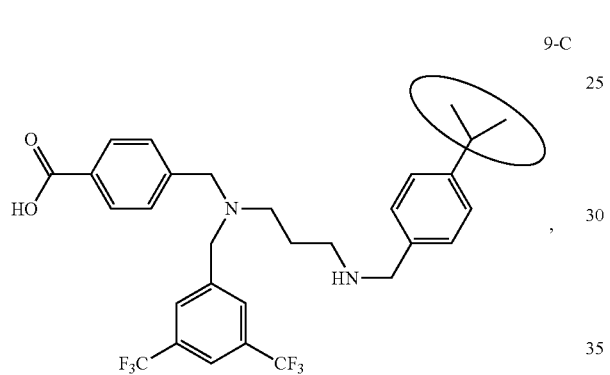
9-c
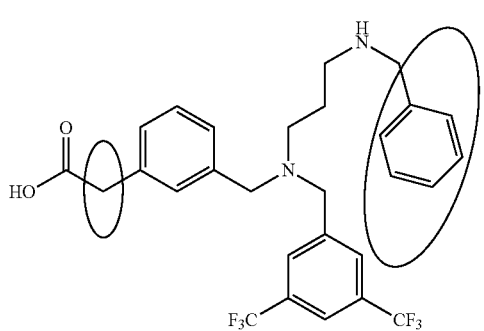
9-g
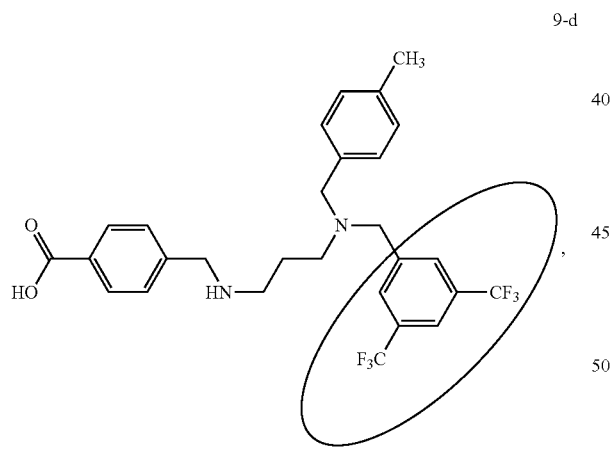
9-d
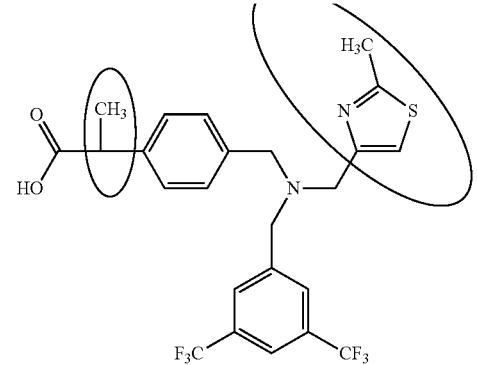
9-h
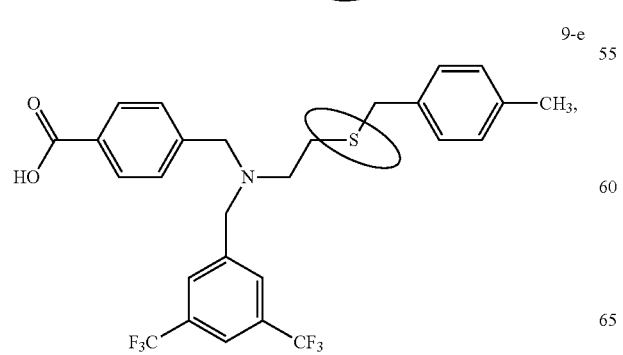
9-e
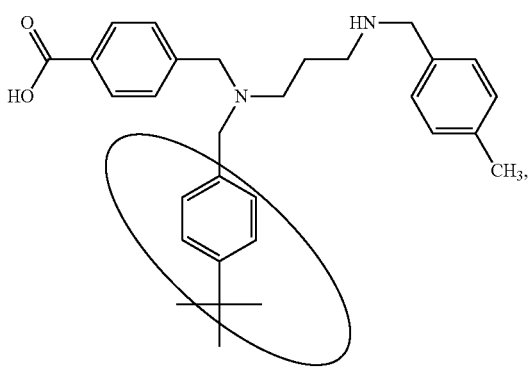
9-i

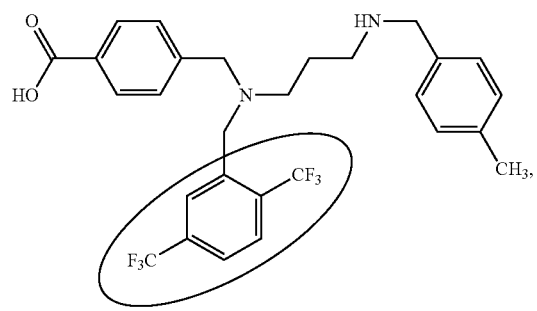
9-j
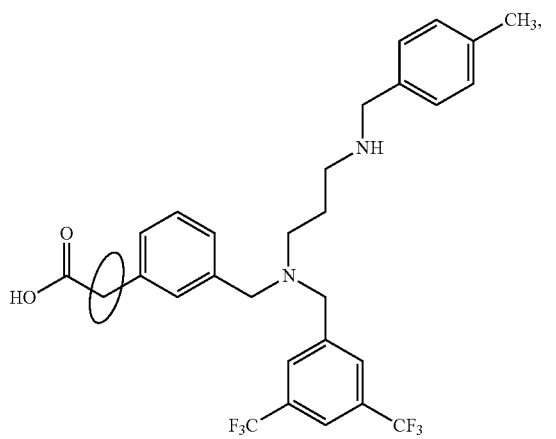
9-M
9-k
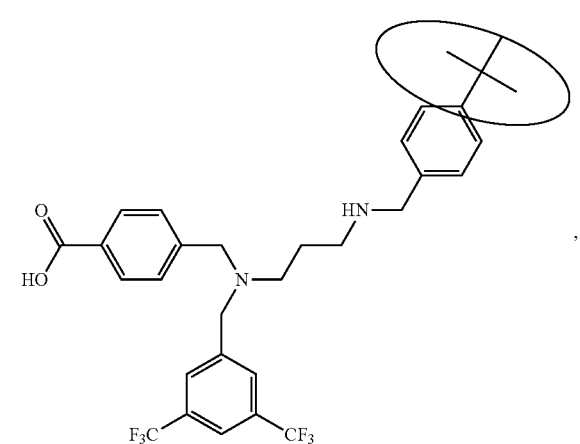
9-t
9-L

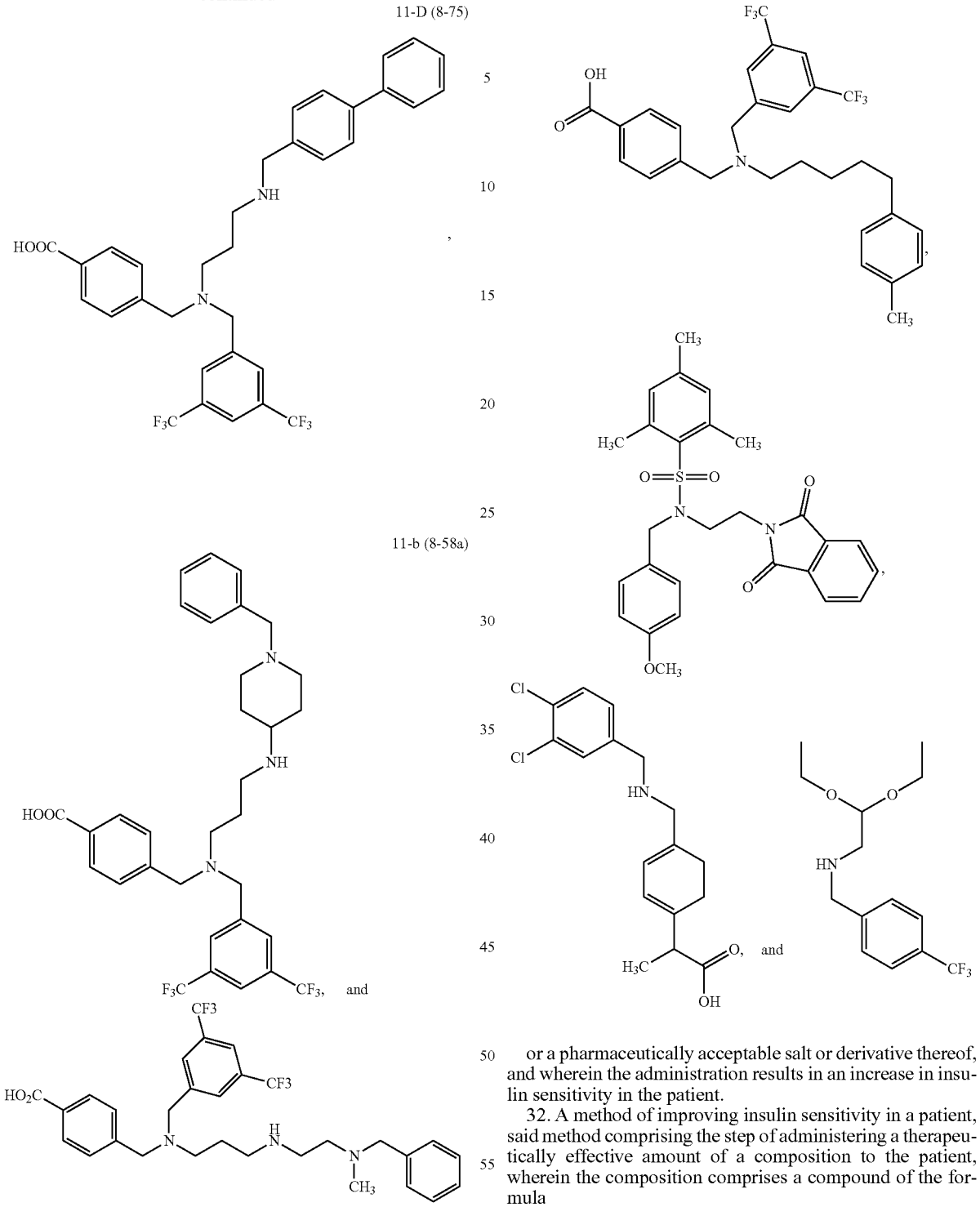

or a pharmaceutically acceptable salt or derivative thereof, and wherein the administration results in improvement of at least one symptom associated with diabetes mellitus in the patient.

31. A method of improving insulin sensitivity in a patient, said method comprising the step of administering a therapeutically effective amount of a composition to the patient, wherein the composition comprises a compound selected from the group consisting of or a pharmaceutically acceptable salt or derivative thereof, and wherein the administration results in an increase in insulin sensitivity in the patient.

32. A method of improving insulin sensitivity in a patient, said method comprising the step of administering a therapeutically effective amount of a composition to the patient, wherein the composition comprises a compound of the formula

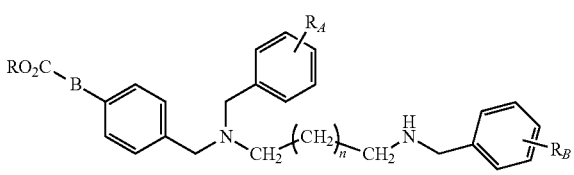

or a pharmaceutically acceptable salt thereof, wherein

B is a bond or $(CH_2)_X$ where x is 1, 2, 3, or 4;

n is 1, 2, or 3;

R is C1-C6 alkyl or hydrogen;

$R_A$ represents from 1 to 4 substituents independently selected in each instance from the group consisting of F and $CF_3$; and $R_B$ is C1-C6 alkyl, F, Cl, Br, CN, or $CF_3$, and wherein the administration results in an increase in insulin sensitivity in the patient.

33. A method of improving insulin sensitivity in a patient, said method comprising the step of administering a therapeutically effective amount of a composition to the patient, wherein the composition comprises a compound selected from the group consisting of

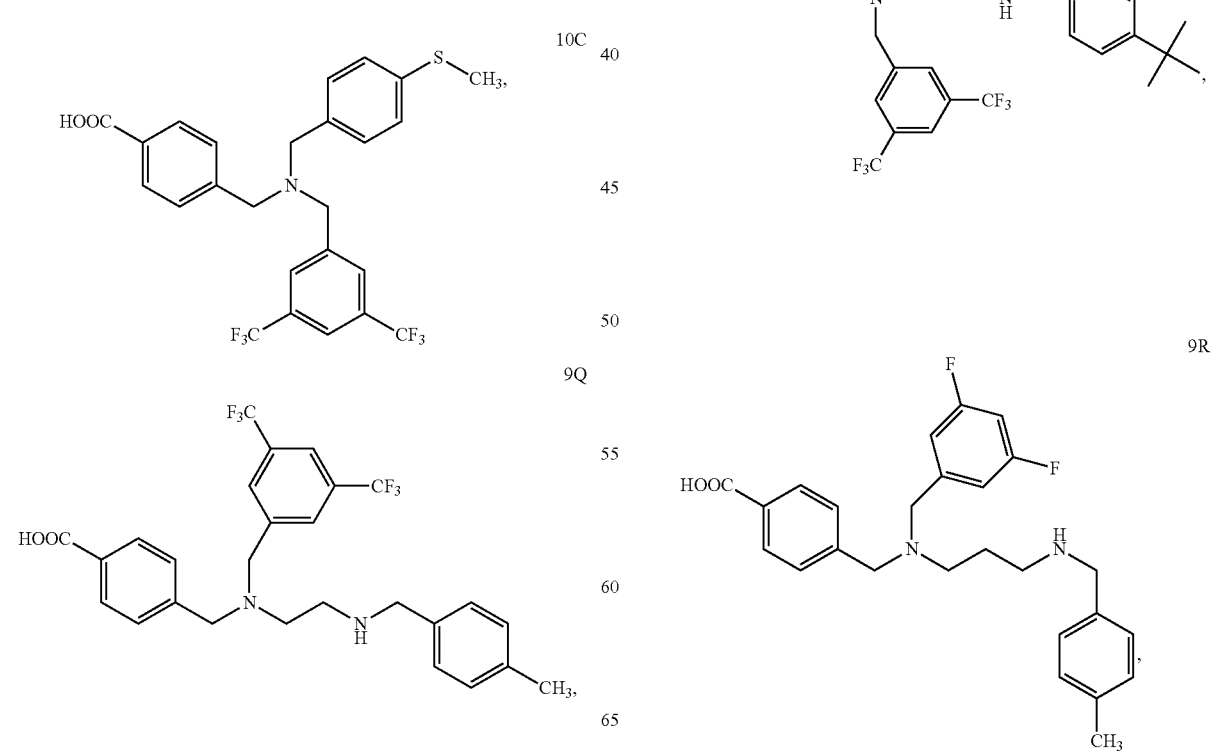

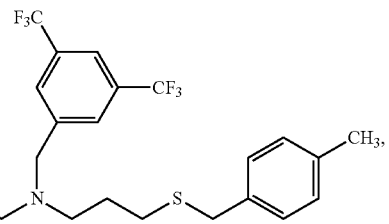

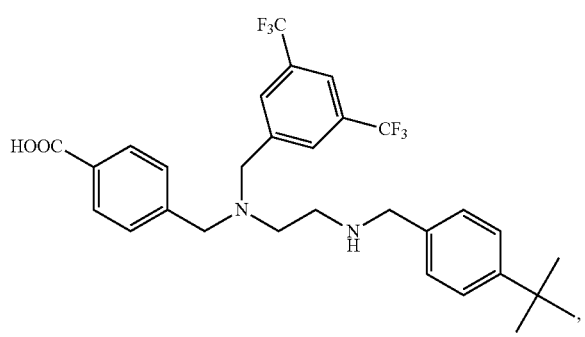

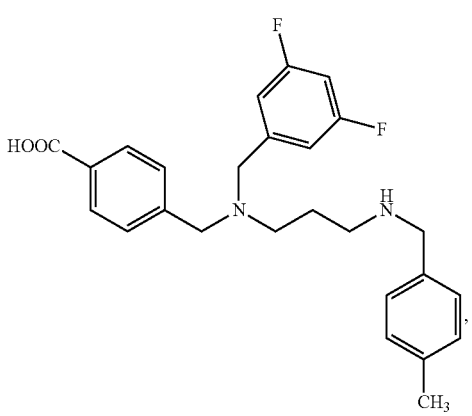

-continued
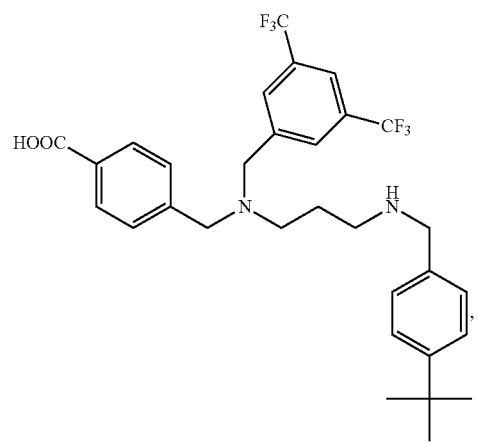
10E
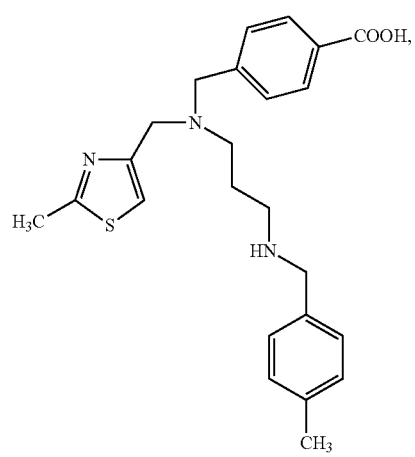
10A
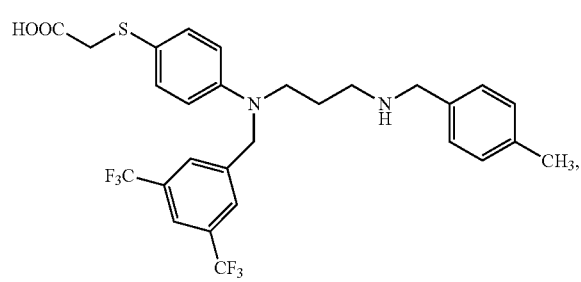
10d
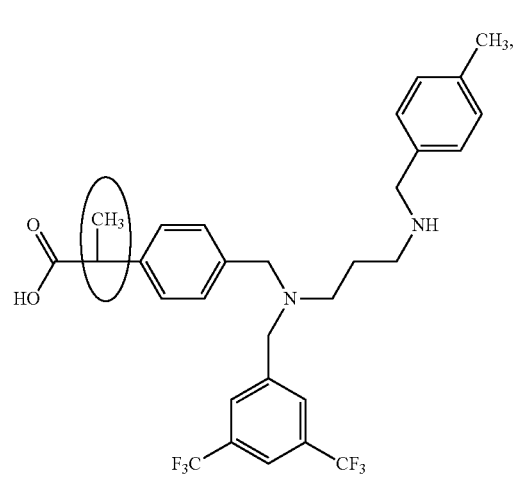
9-b
-continued
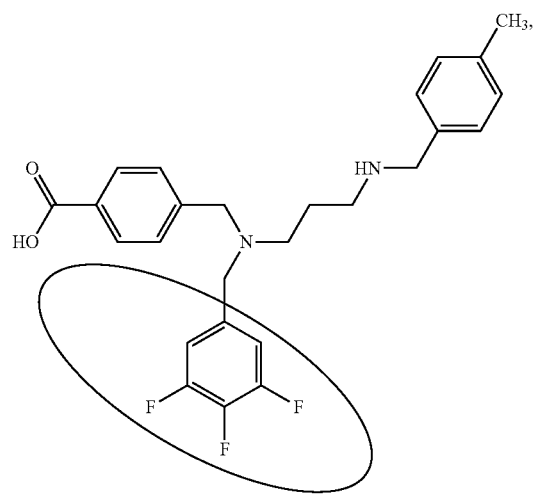
9-f
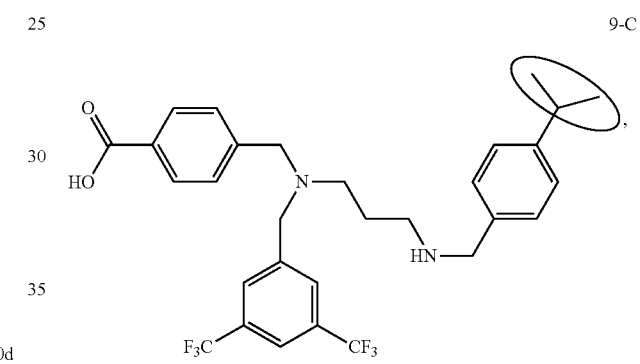
9-C
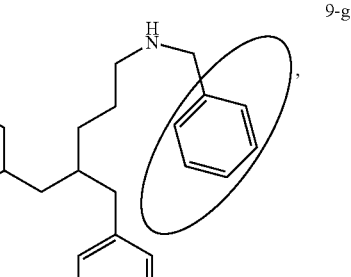
9-g
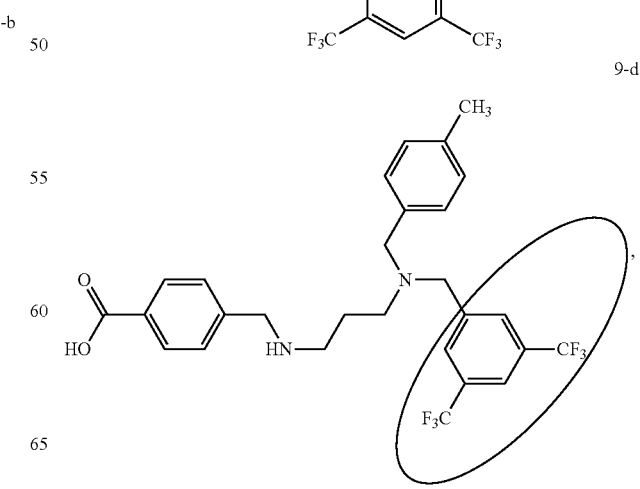
9-d 9-h
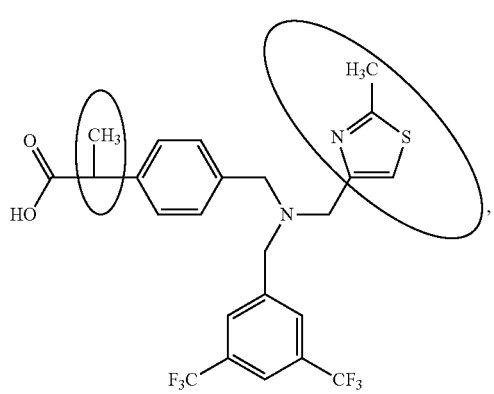
9-k
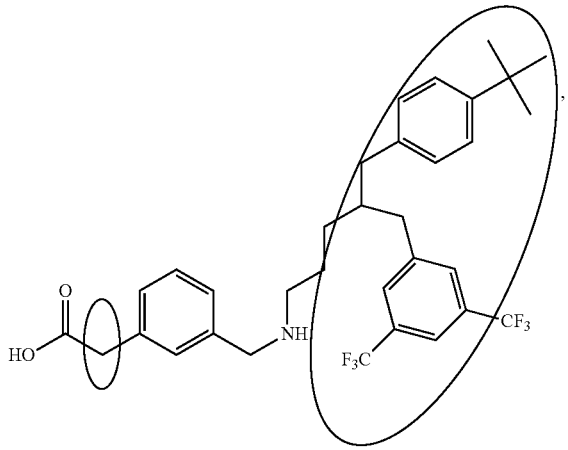
9-e
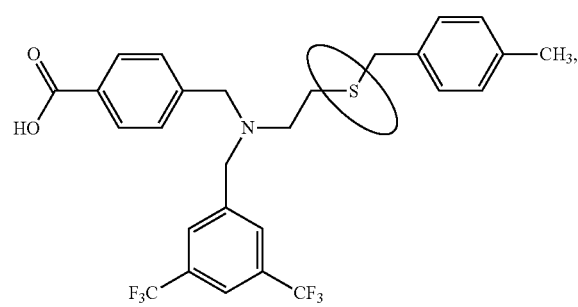
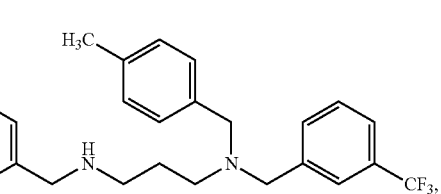
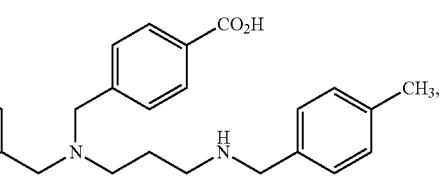
9-i
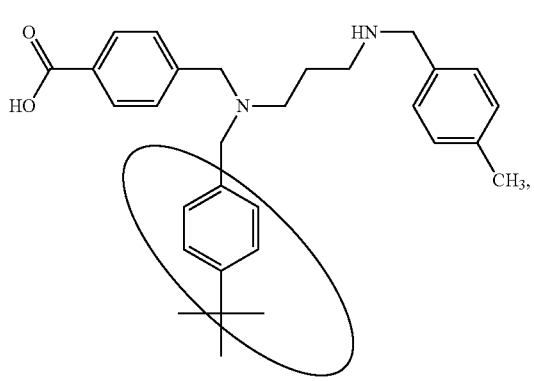
9-j
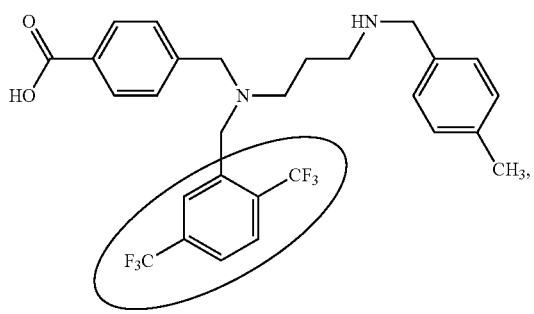
9-L
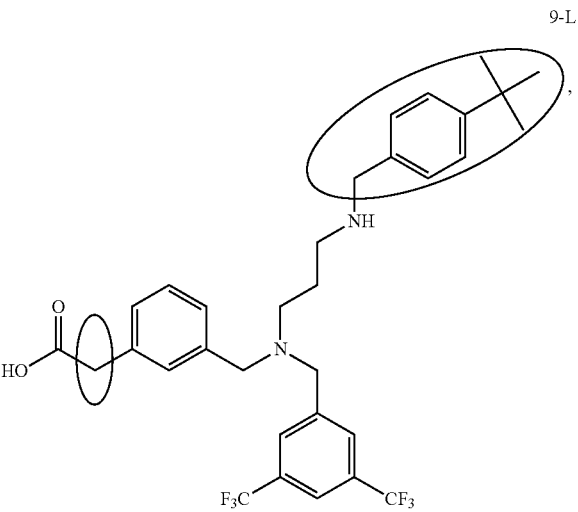

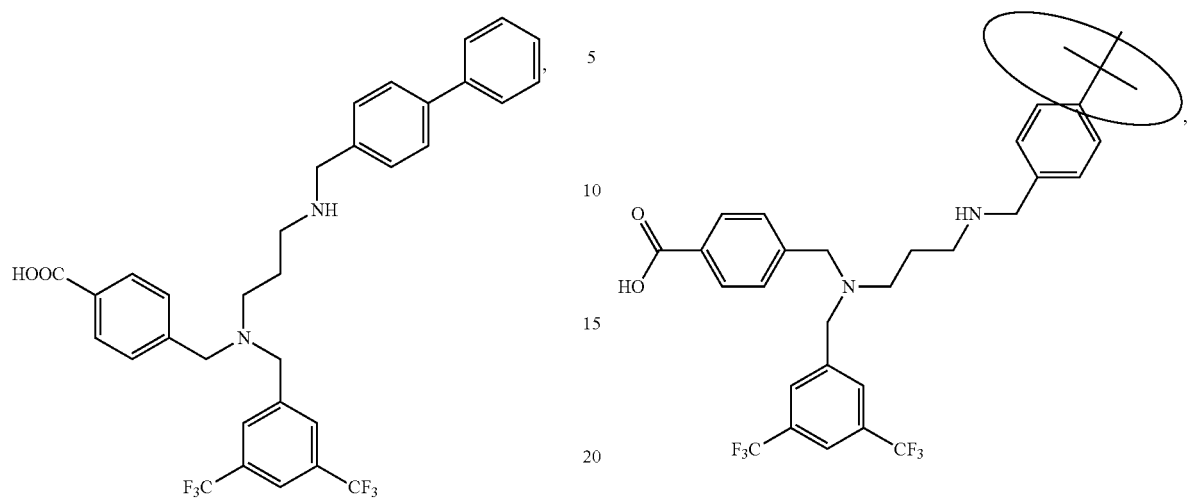

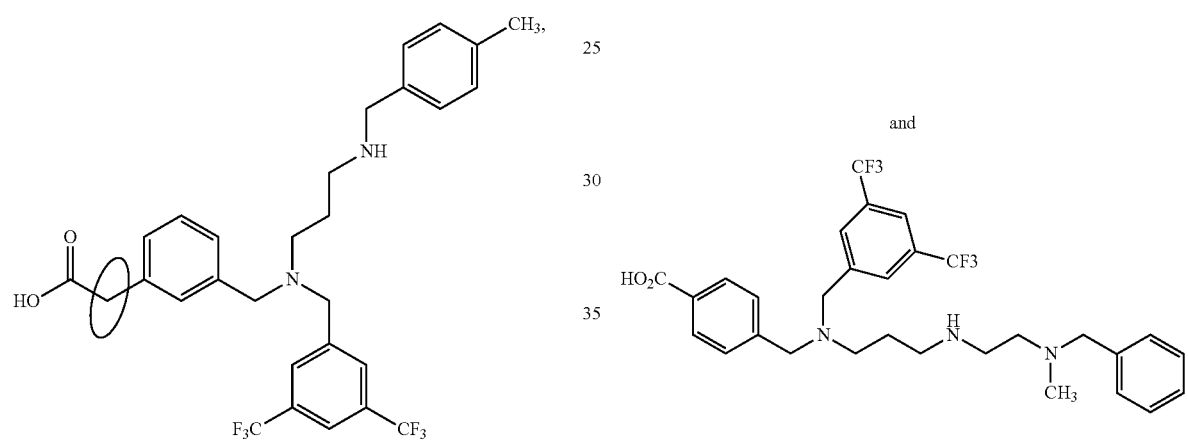

or a pharmaceutically acceptable salt or derivative thereof, and wherein the administration results in an increase in insulin sensitivity in the patient.

34. A method of improving glucose utilization in a patient, said method comprising the step of administering a therapeutically effective amount of a composition to the patient, wherein the composition comprises a compound selected from the group consisting of

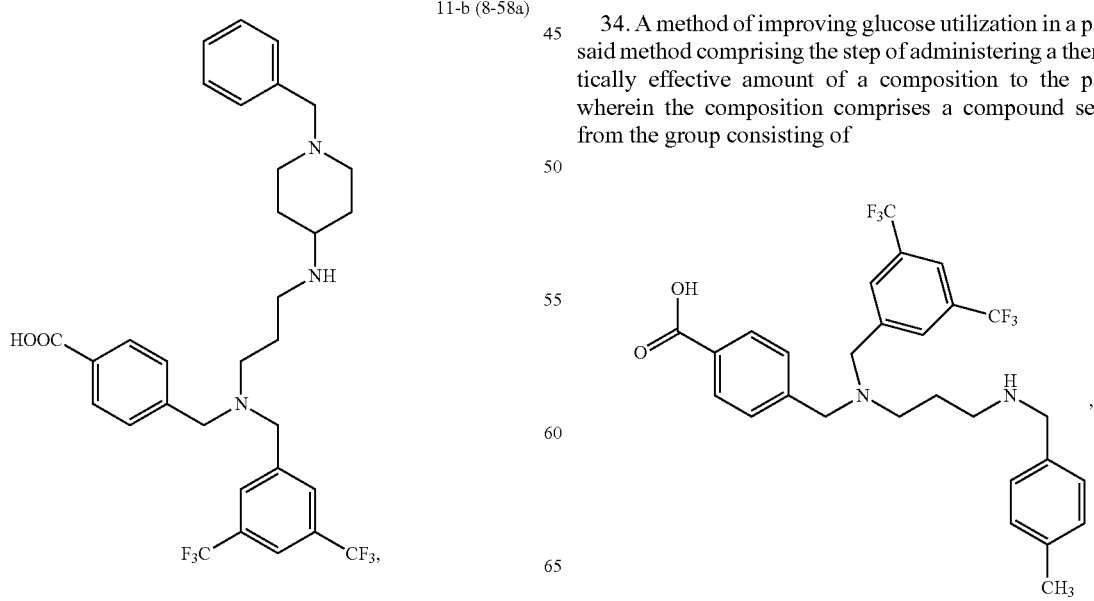

-continued

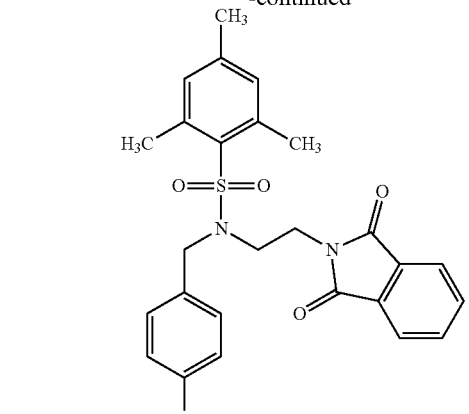

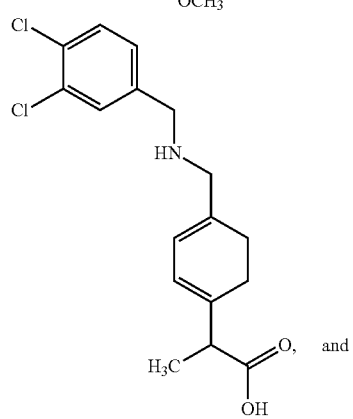, and 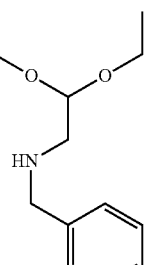

or a pharmaceutically acceptable salt or derivative thereof, and wherein the administration results in an increase in glucose utilization in the patient.

35. A method of improving glucose utilization in a patient, said method comprising the step of administering a therapeutically effective amount of a composition to the patient, wherein the composition comprises a compound of the formula

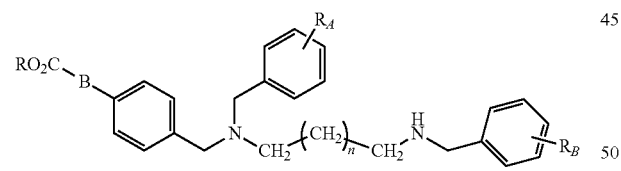

or a pharmaceutically acceptable salt thereof, wherein
B is a bond or $(CH_2)_x$ where x is 1, 2, 3, or 4;
n is 1, 2, or 3;
R is C1-C6 alkyl or hydrogen;
$R_A$ represents from 1 to 4 substituents independently selected in each instance from the group consisting of F and $CF_3$; and
$R_B$ is C1-C6 alkyl, F, Cl, Br, CN, or $CF_3$, and
wherein the administration results in an increase in glucose utilization in the patient.

36. A method of improving glucose utilization in a patient, said method comprising the step of administering a therapeutically effective amount of a composition to the patient, wherein the composition comprises a compound selected from the group consisting of

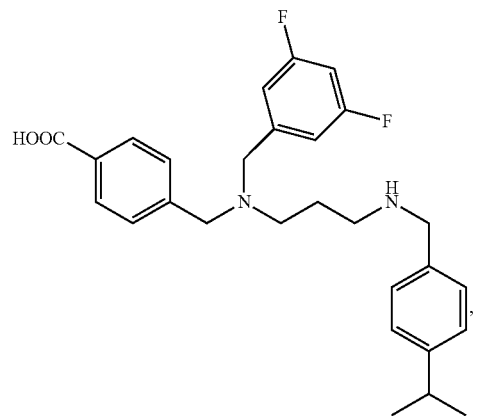
9S

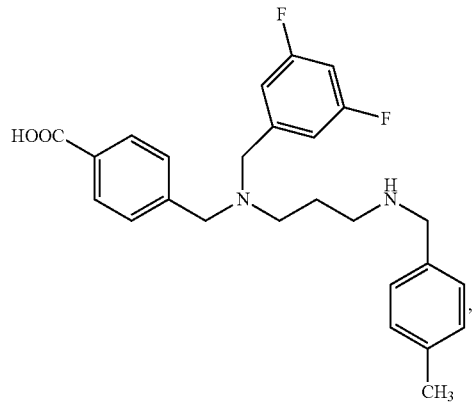
9R

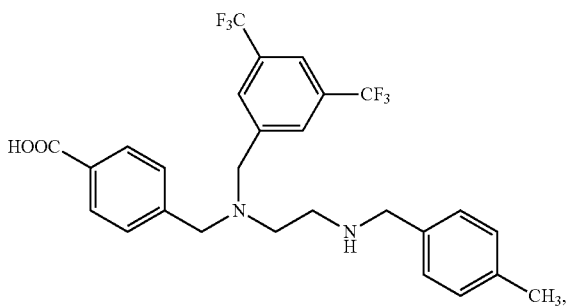
9Q

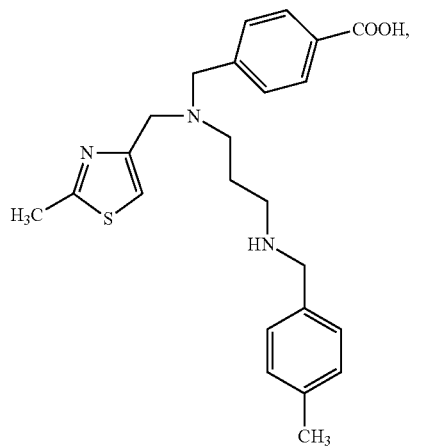
10A

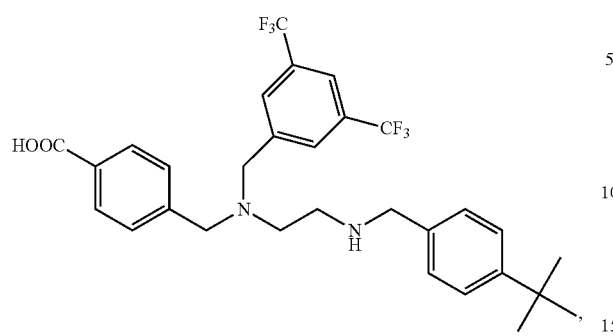
10F
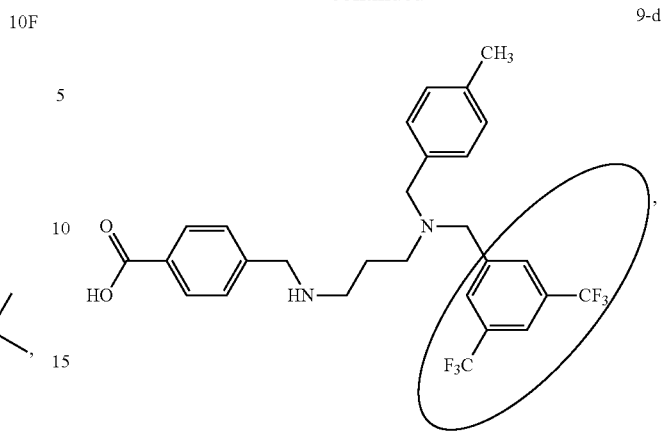
9-d
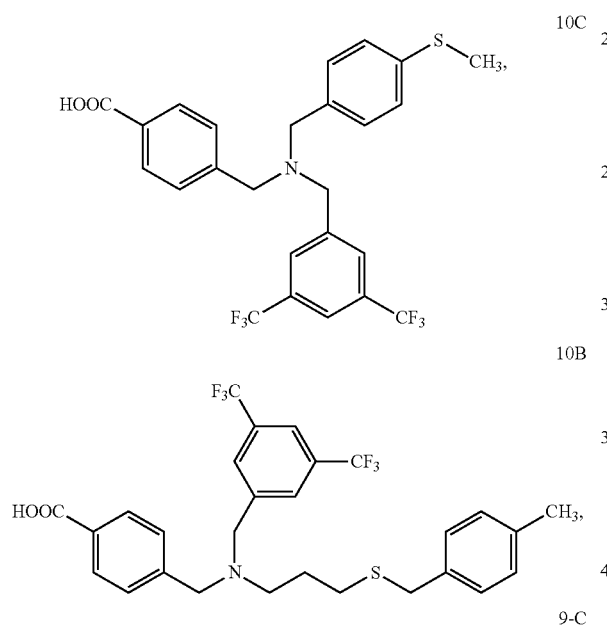
10C
10B
9-C
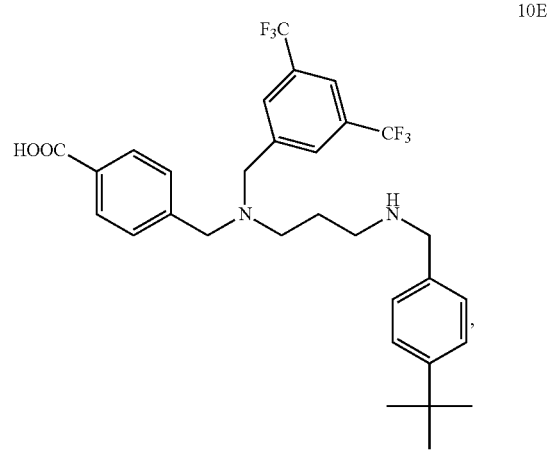
10E
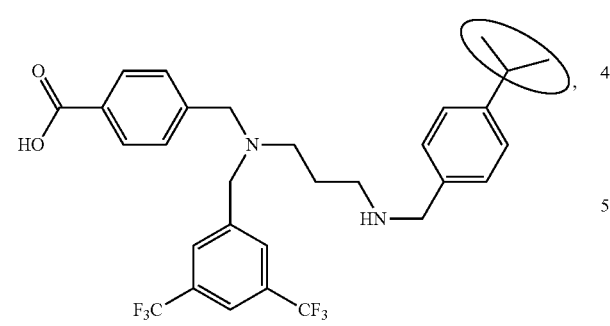
10G
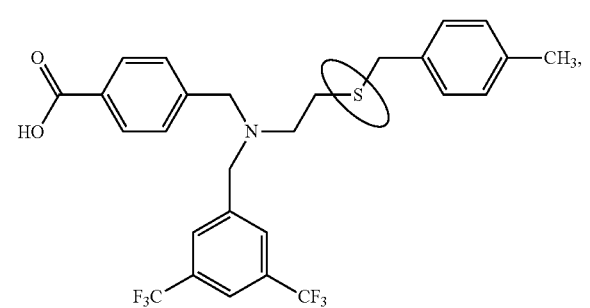
9-e
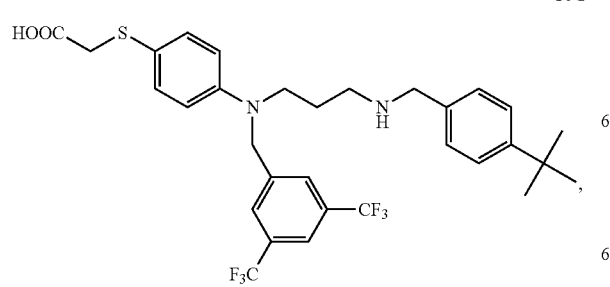
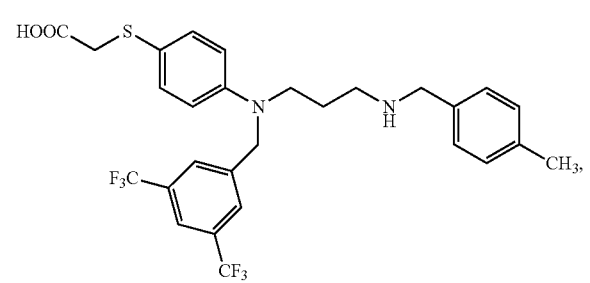
10d

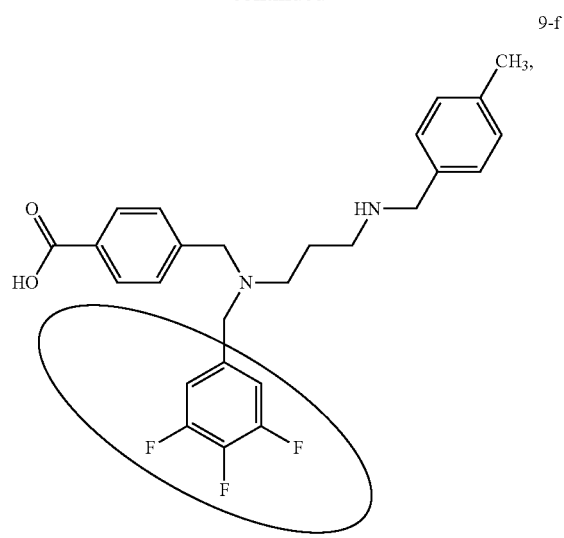
9-f
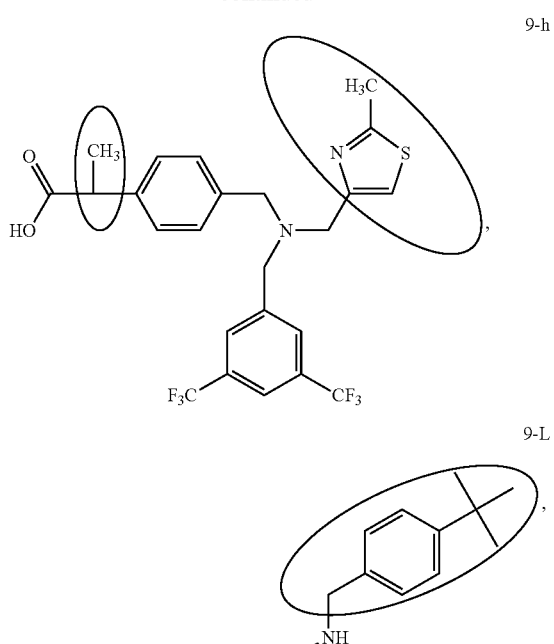
9-h
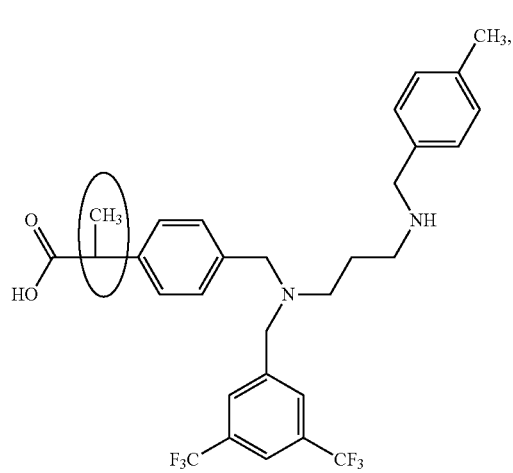
9-b
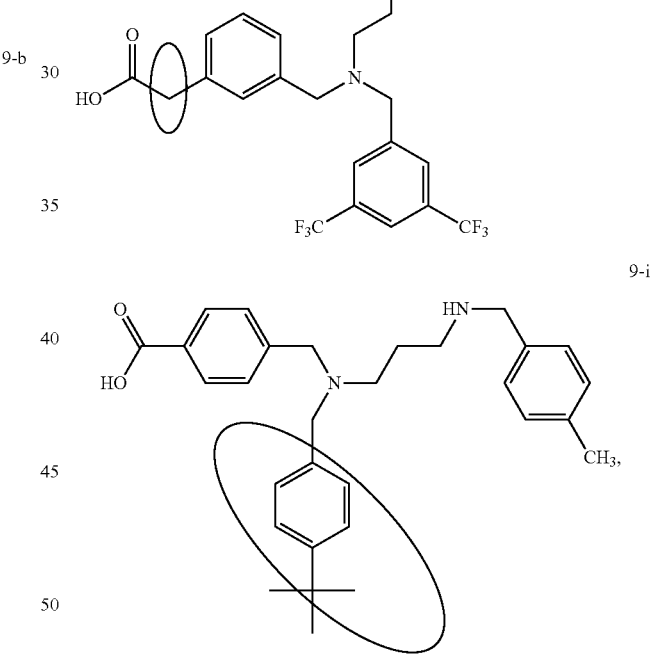
9-L
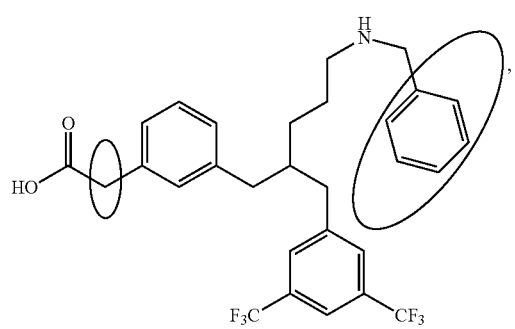
9-g
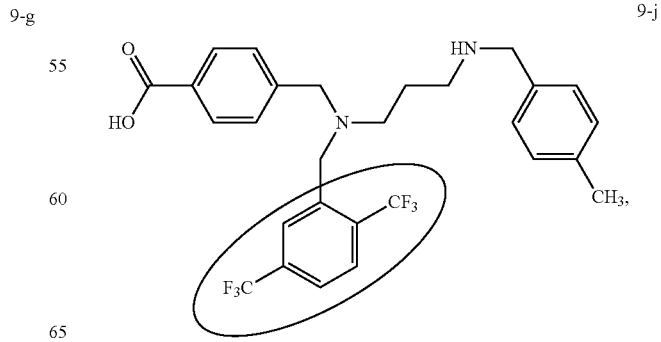
9-i
9-j

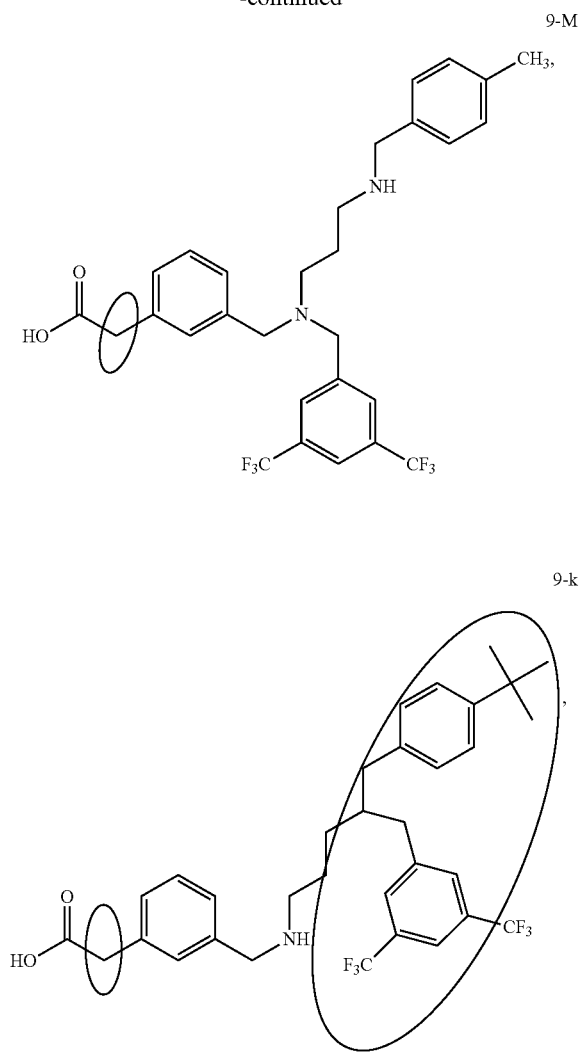
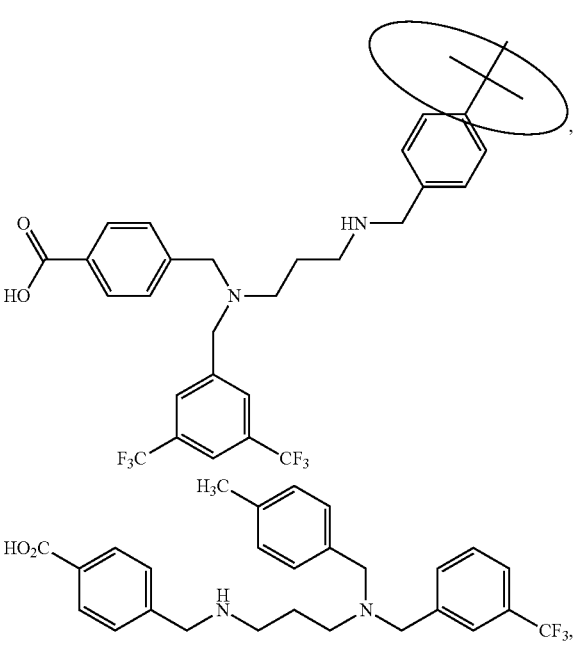
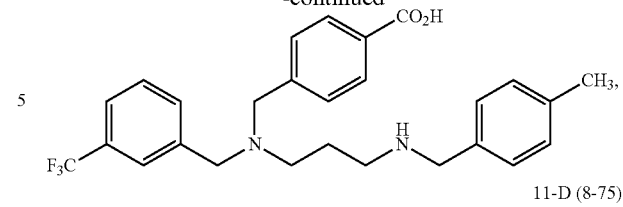
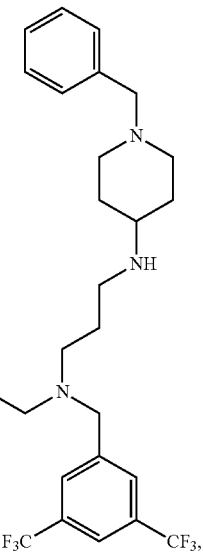
or a pharmaceutically acceptable salt or derivative thereof, and wherein the administration results in an increase in glucose utilization in the patient.

37. A method of treating Alzheimer's disease in a patient in need thereof, said method comprising the step of administering a therapeutically effective amount of a composition to the patient, wherein the composition comprises a compound selected from the group consisting of

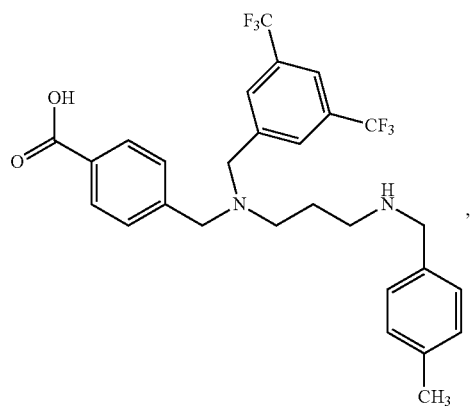 [SMILES: Cc1ccc(CNCCCN(Cc2ccc(C(=O)O)cc2)Cc2cc(C(F)(F)F)cc(C(F)(F)F)c2)cc1]

,

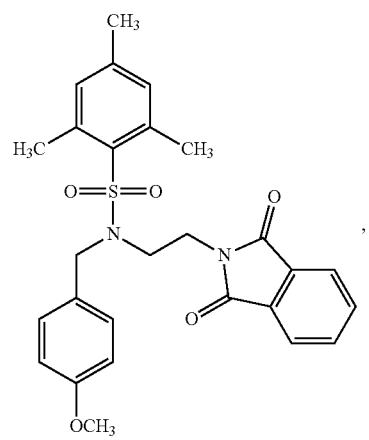

,

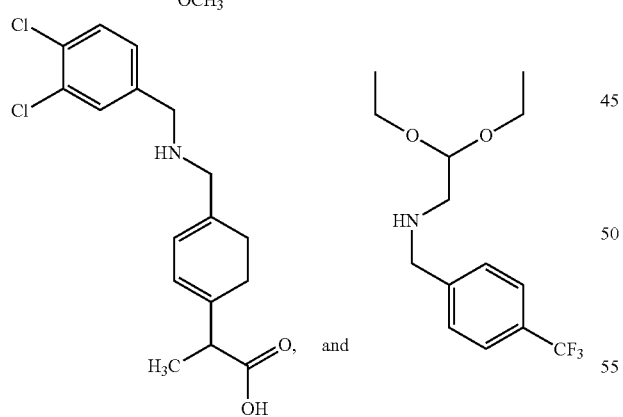

or a pharmaceutically acceptable salt or derivative thereof, and wherein the administration results in improvement of at least one symptom associated with Alzheimer's disease in the patient.

38. A method of treating Alzheimer's disease in a patient in need thereof, said method comprising the step of administering a therapeutically effective amount of a composition to the patient, wherein the composition comprises a compound of the formula

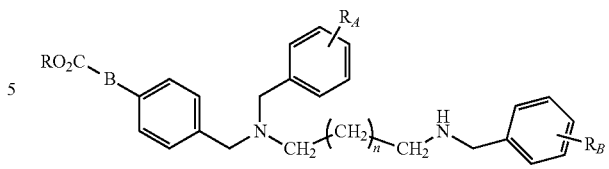

or a pharmaceutically acceptable salt thereof, wherein

B is a bond or $(CH_2)_X$ where x is 1, 2, 3, or 4;

n is 1, 2, or 3;

R is C1-C6 alkyl or hydrogen;

$R_A$ represents from 1 to 4 substituents independently selected in each instance from the group consisting of F and $CF_3$; and $R_B$ is C1-C6 alkyl, F, Cl, Br, CN, or $CF_3$, and wherein the administration results in improvement of at least one symptom associated with Alzheimer's disease in the patient.

39. A method of treating Alzheimer's disease in a patient in need thereof, said method comprising the step of administering a therapeutically effective amount of a composition to the patient, wherein the composition comprises a compound selected from the group consisting of

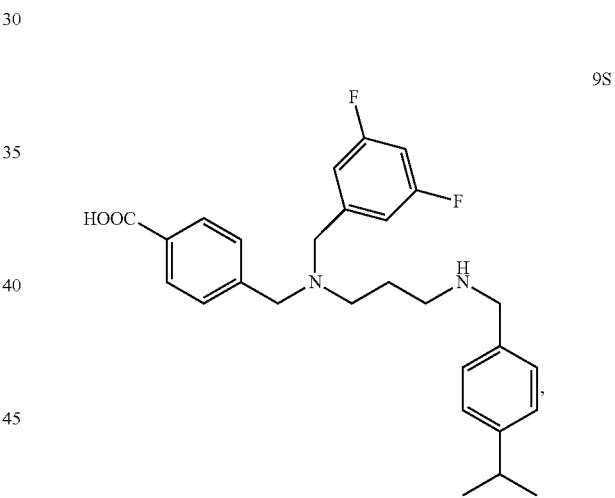

9S

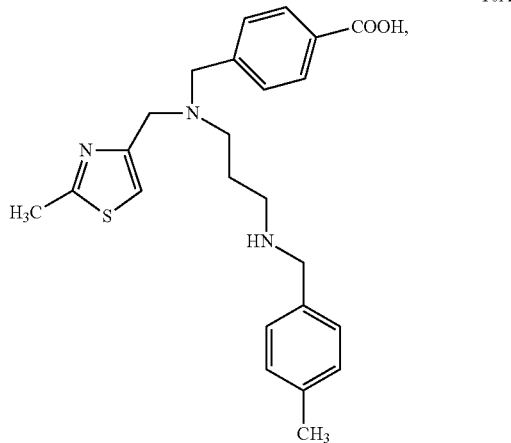

10A

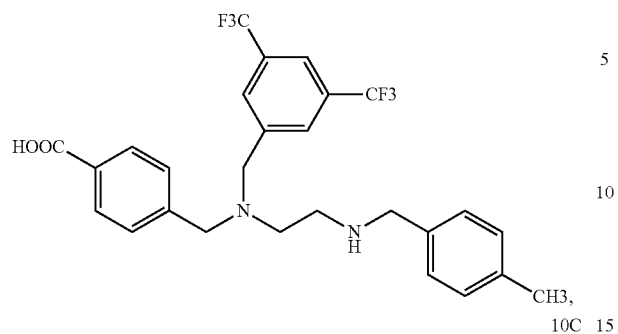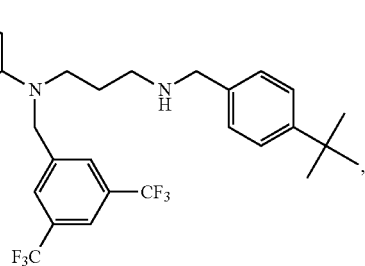

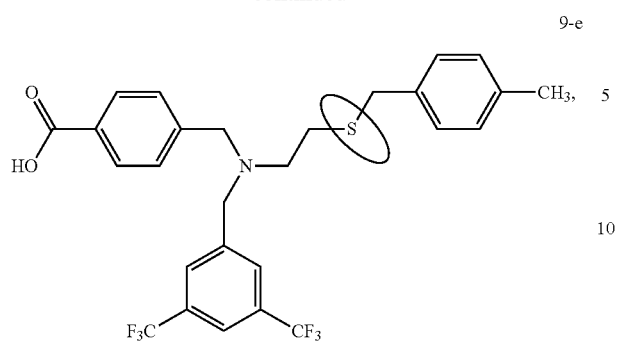
9-e
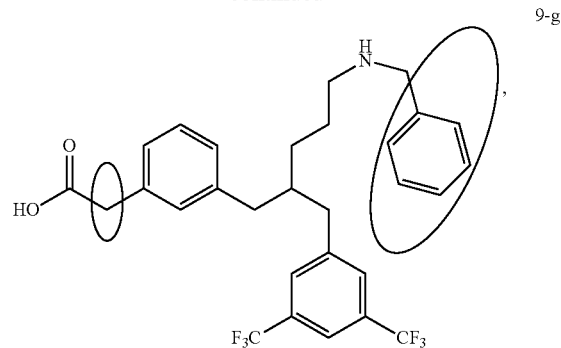
9-g
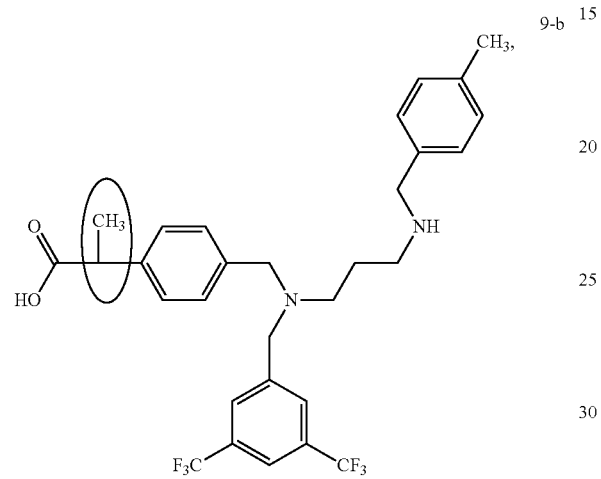
9-b
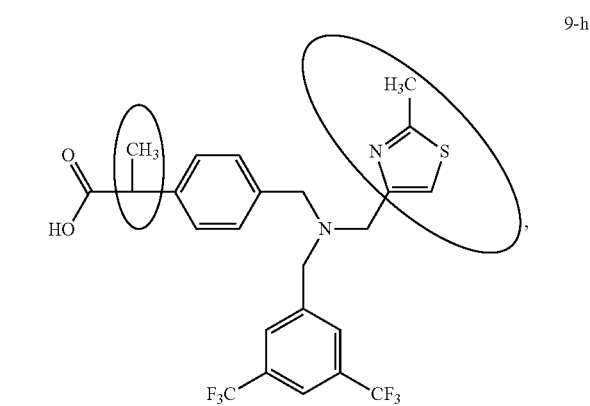
9-h
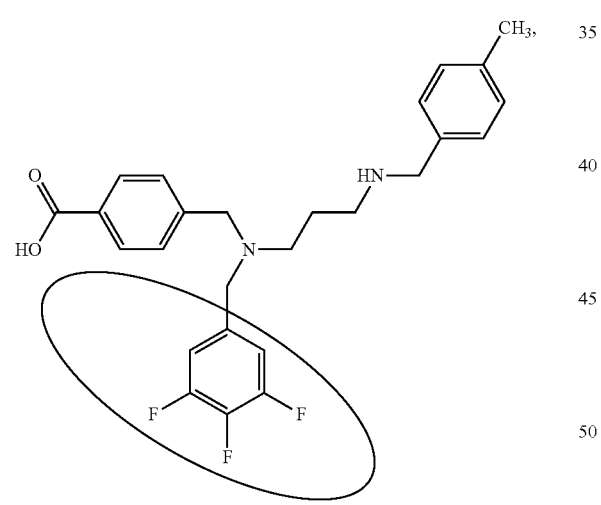
9-f
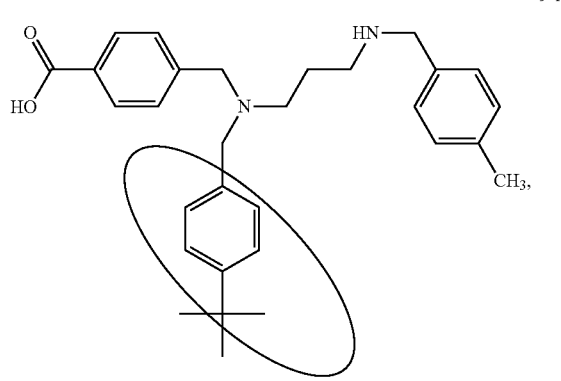
9-i
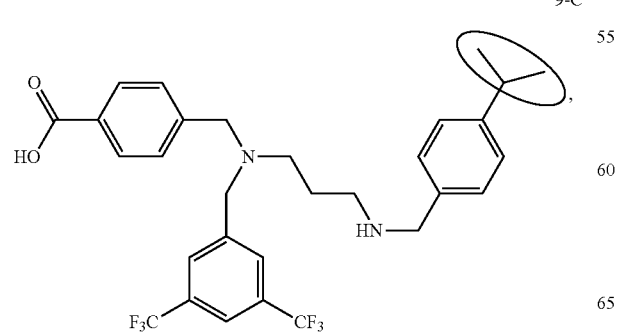
9-C
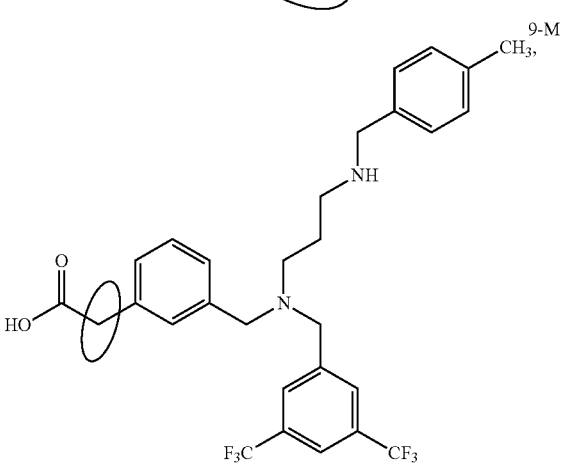
9-M

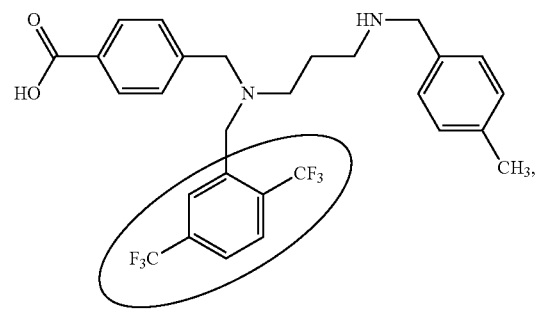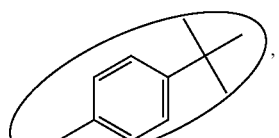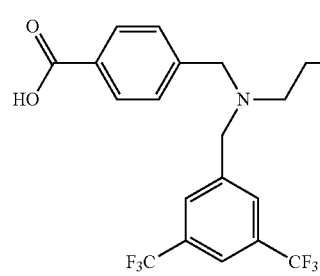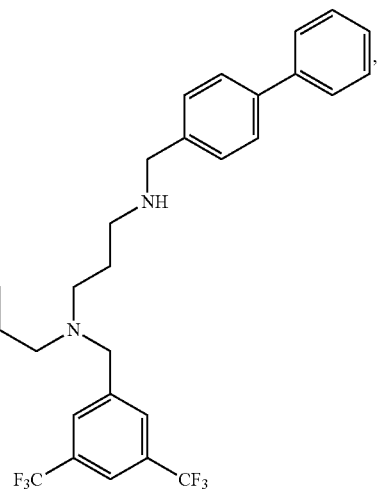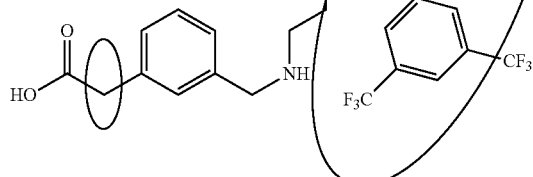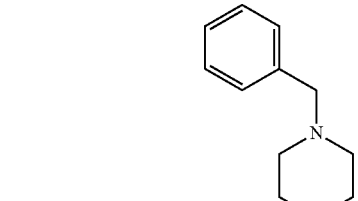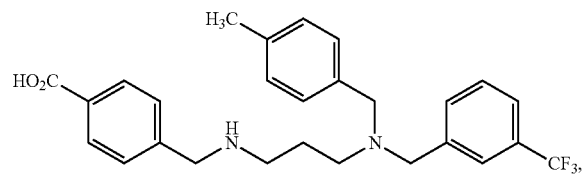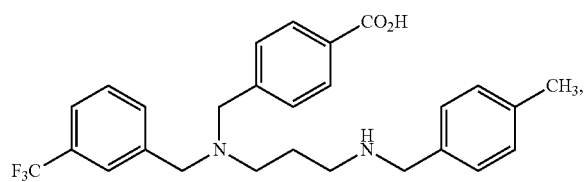

-continued

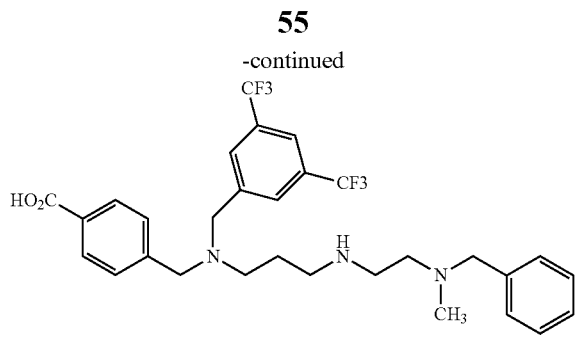

or a pharmaceutically acceptable salt or derivative thereof, and wherein the administration results in improvement of at least one symptom associated with Alzheimer's disease in the patient.

40. A method of improving a cognitive deficit in a patient, said method comprising the step of administering a therapeutically effective amount of a composition to the patient, wherein the composition comprises a compound selected from the group consisting of

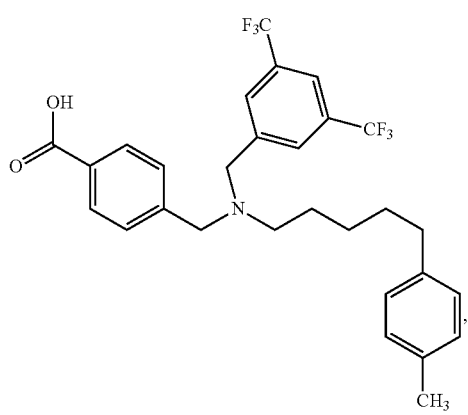

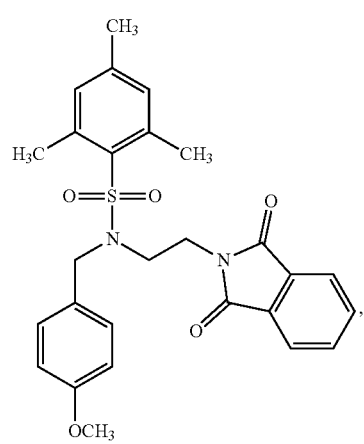

-continued

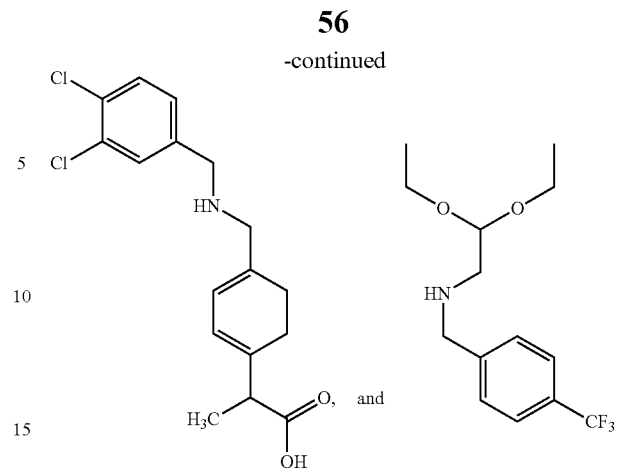

or a pharmaceutically acceptable salt or derivative thereof, and wherein the administration results in an improvement in a cognitive deficit in the patient.

41. A method of improving a cognitive deficit in a patient, said method comprising the step of administering a therapeutically effective amount of a composition to the patient, wherein the composition comprises a compound of the formula

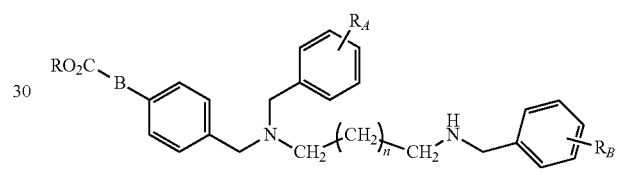

or a pharmaceutically acceptable salt thereof, wherein
B is a bond or $(CH_2)_x$ where x is 1, 2, 3, or 4;
n is 1, 2, or 3;
R is C1-C6 alkyl or hydrogen;
$R_A$ represents from 1 to 4 substituents independently selected in each instance from the group consisting of F and $CF_3$; and
$R_B$ is C1-C6 alkyl, F, Cl, Br, CN, or $CF_3$, and wherein the administration results in an improvement in a cognitive deficit in the patient 42. A method of improving a cognitive deficit in a patient, said method comprising the step of administering a therapeutically effective amount of a composition to the patient, wherein the composition comprises a compound selected from the group consisting of

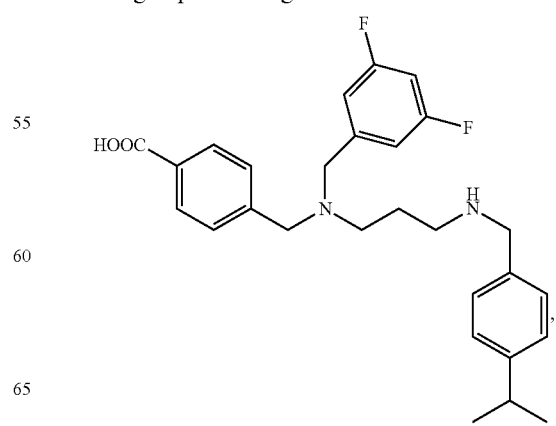

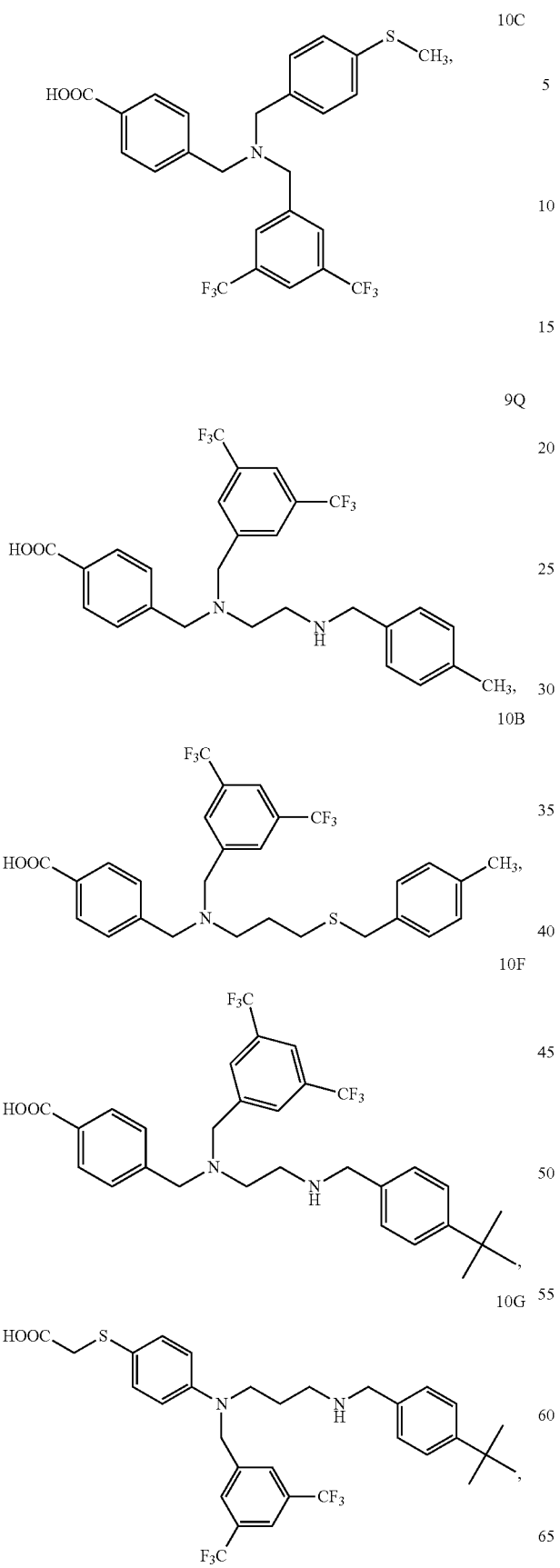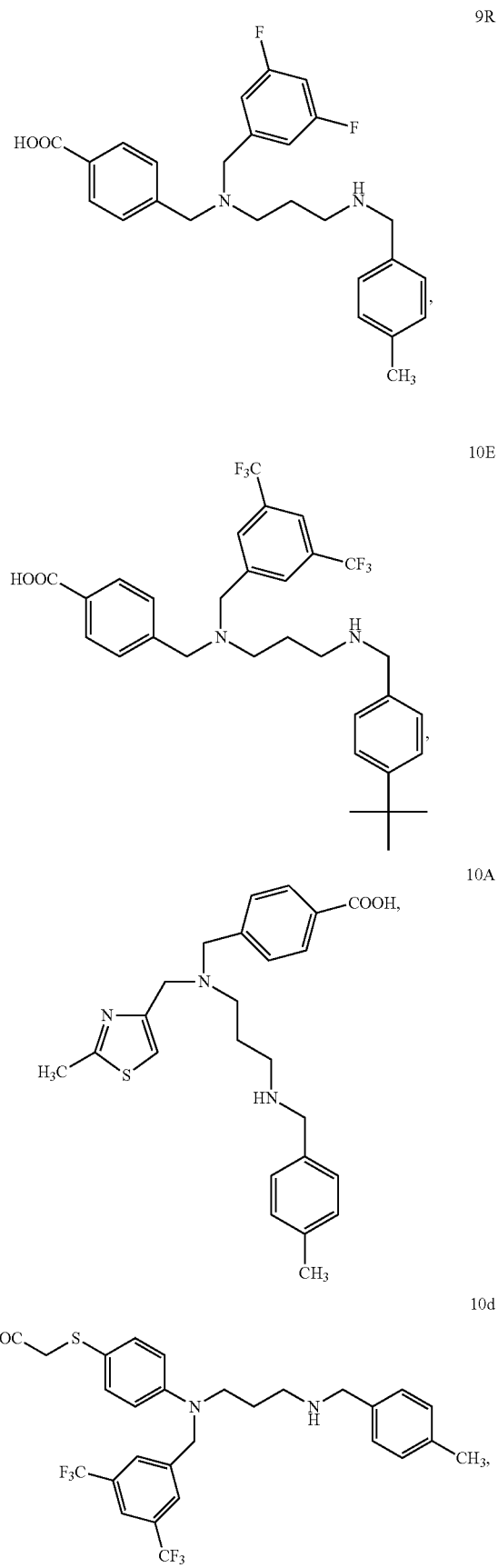

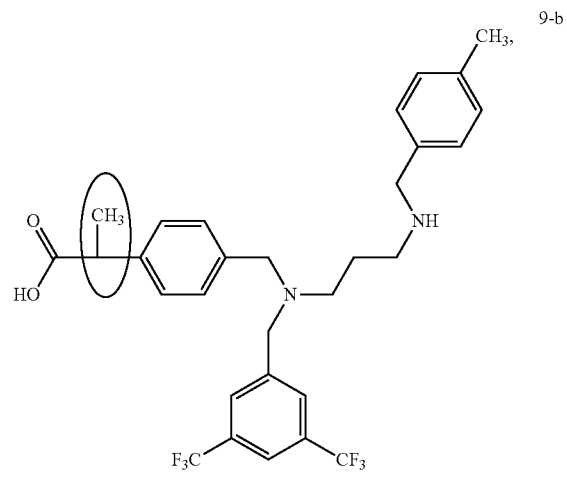
9-b
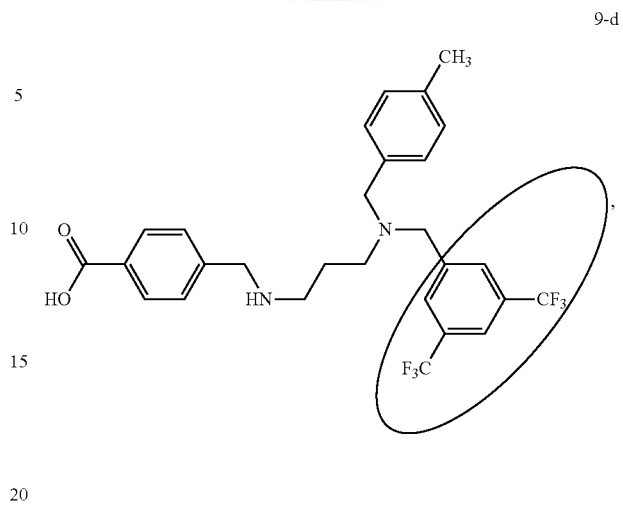
9-d
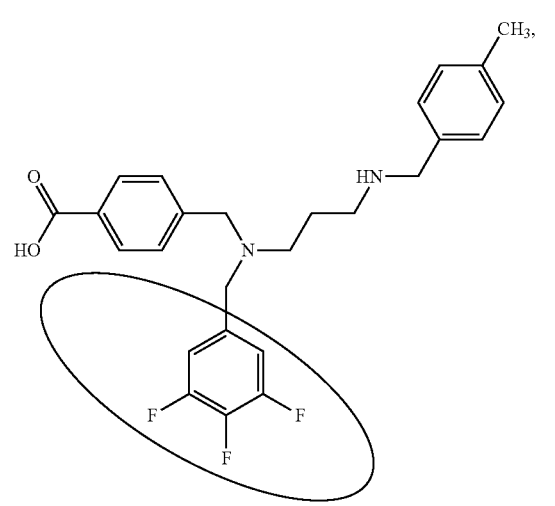
9-f
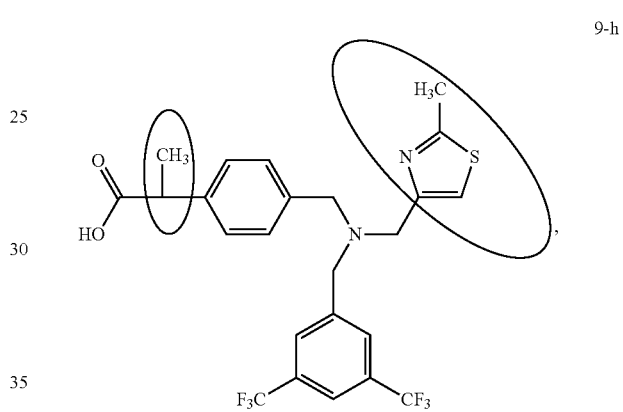
9-h
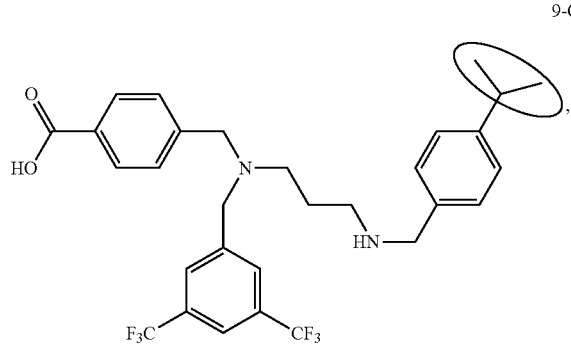
9-c
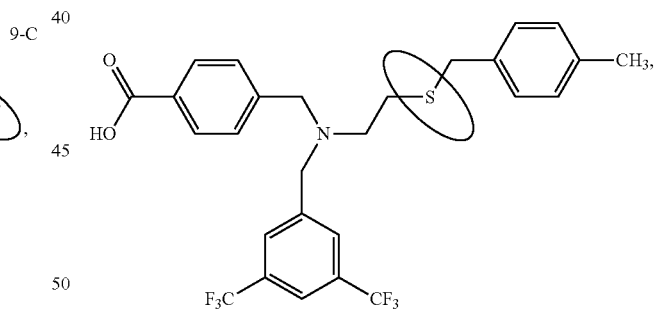
9-e
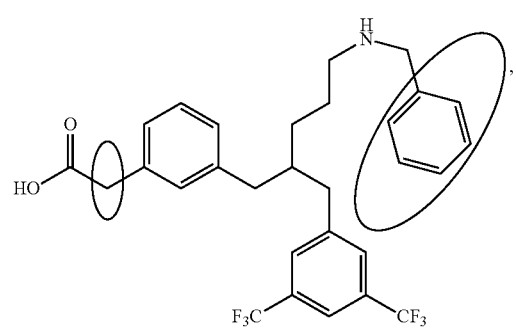
9-g
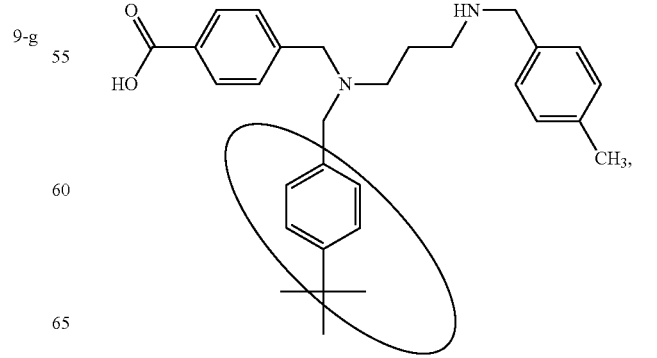
9-i

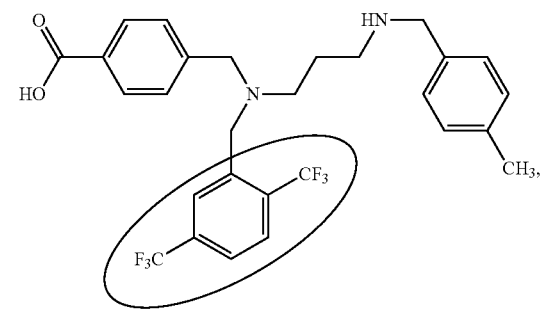
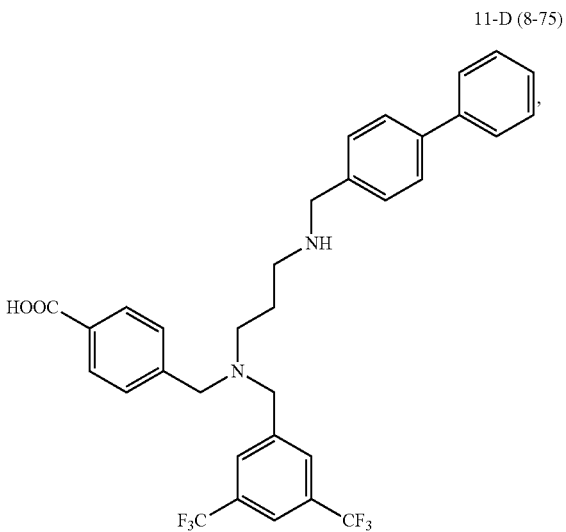
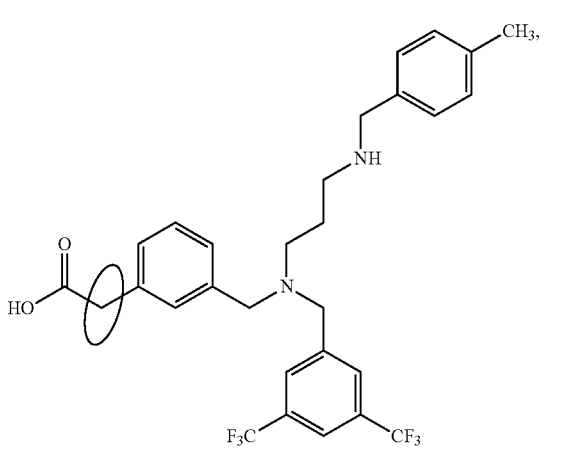
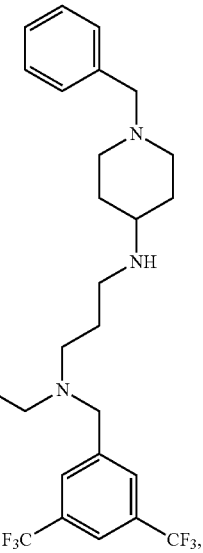

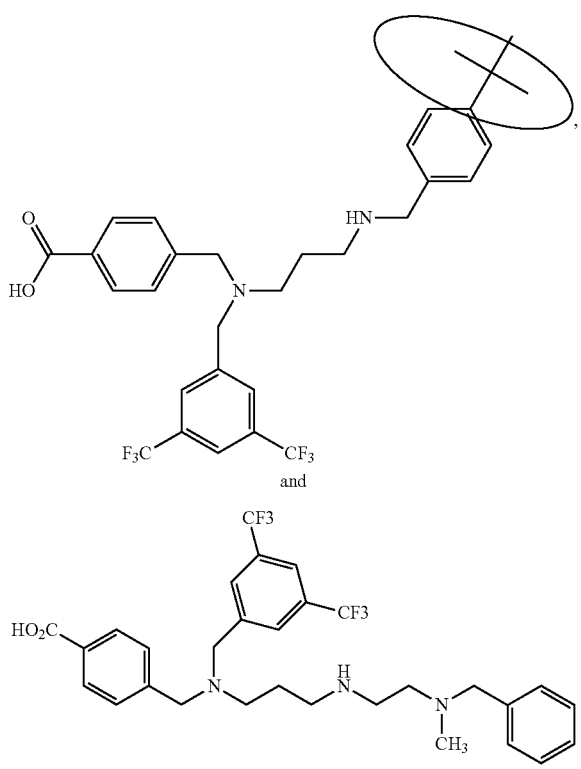

or a pharmaceutically acceptable salt or derivative thereof, and wherein the administration results in an improvement in a cognitive deficit in the patient.

43. The method of any of the above clauses, wherein the method is associated with improved insulin sensitivity in the patient.

44. The method of any of the above clauses, wherein the method is associated with improved glucose utilization in the patient.

45. The method of any of the above clauses, wherein the method is associated with improved induction of mitochondrial biogenesis in the patient.

46. The method of any of the above clauses, wherein the method is associated with improved insulin signaling in the brain of the patient.

47. The method of any of the above clauses, wherein the method is not associated with lipid accumulation in the patient.

48. The method of any of the above clauses, wherein the lipid accumulation is ectopic lipid accumulation.

49. The method of any of the above clauses, wherein the method is not associated with adverse cardiovascular event in the patient.

50. The method of any of the above clauses, wherein the adverse cardiovascular event is heart failure.

51. The method of any of the above clauses, wherein the adverse cardiovascular event is a myocardial infarction.

52. The method of any of the above clauses, wherein the method does not induce an increase in lipid accumulation in the patient.

53. The method of any of the above clauses, wherein the lipid accumulation is ectopic lipid accumulation.

54. The method of any of the above clauses, wherein the diabetes mellitus is Type 1 diabetes mellitus.

55. The method of any of the above clauses, wherein the diabetes mellitus is Type 2 diabetes mellitus.

56. The method of any of the above clauses, wherein the method is associated with improvement of a cognitive deficit in the patient.

57. The method of any of the above clauses, wherein the cognitive deficit is memory impairment.

58. The method of any of the above clauses, wherein the method is associated with an improvement in cognition in the patient.

59. The method of any of the above clauses, wherein the method is associated with central PPARγ activation.

60. The method of any of the above clauses, wherein the central PPARγ activation is in the hippocampus of the patient.

61. The method of any of the above clauses, wherein the method is associated with an improvement in synaptic plasticity in the patient.

62. The method of any of the above clauses, wherein the method is associated with a decrease in Tau phosphorylation in the hippocampus of the patient.

63. The method of any of the above clauses, wherein the method is associated with a decrease in PTEN expression in the hippocampus of the patient.

64. The method of any of the above clauses, wherein the method is associated with an increase in BDNF expression in the hippocampus of the patient.

65. The method of any of the above clauses, wherein the method is associated with improved insulin sensitivity in the patient.

66. The method of any of the above clauses, wherein the method is associated with improved glucose utilization in the patient.

67. The method of any of the above clauses, wherein the method is associated with improved induction of mitochondrial biogenesis in the patient.

68. The method of any of the above clauses, wherein the method is associated with improved insulin signaling in the brain of the patient.

69. The method of any of the above clauses, wherein the method is not associated with lipid accumulation in the patient.

70. The method of any of the above clauses, wherein the lipid accumulation is ectopic lipid accumulation.

71. The method of any of the above clauses, wherein the method is not associated with adverse cardiovascular event in the patient.

72. The method of any of the above clauses, wherein the adverse cardiovascular event is heart failure.

73. The method of any of the above clauses, wherein the adverse cardiovascular event is a myocardial infarction.

74. The method of any of the above clauses, wherein the method does not induce an increase in lipid accumulation in the patient.

75. The method of any of the above clauses, wherein the lipid accumulation is ectopic lipid accumulation.

Figure 1:
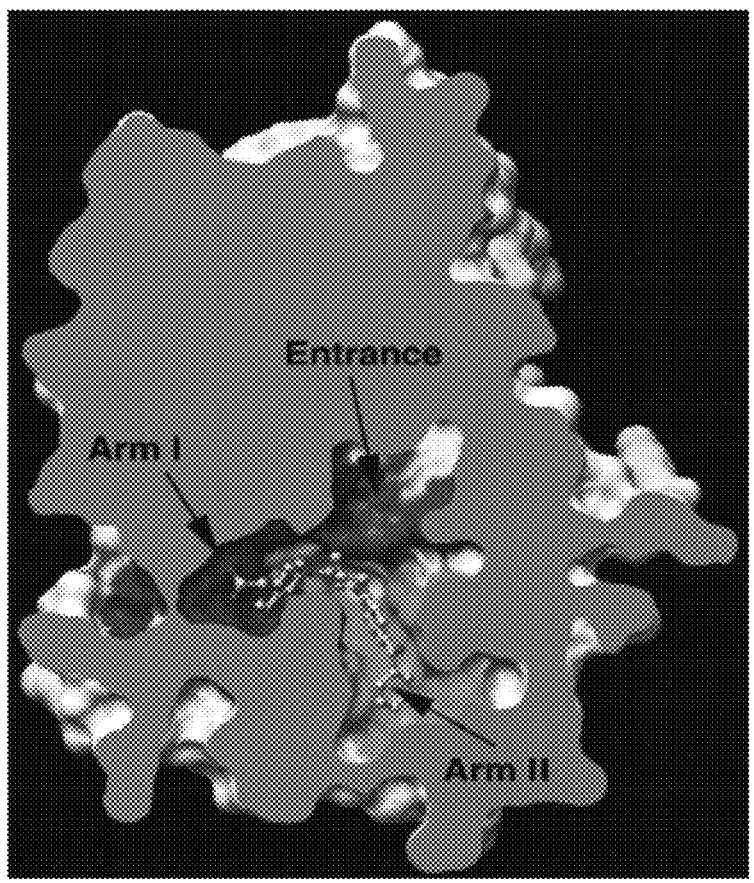
FIG. 1 shows the ligand binding domain of PPARγ bound with an agonist.

Various embodiments of the invention are described herein as follows. In one embodiment described herein, a composition is provided. The composition comprises a compound selected from the group consisting of

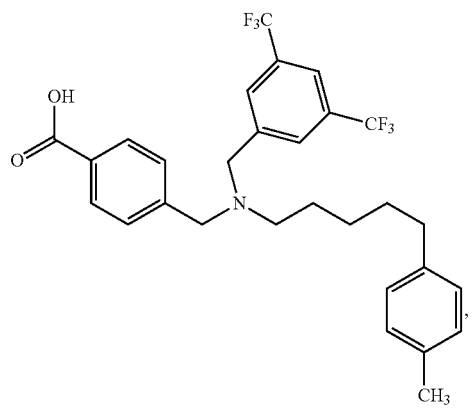

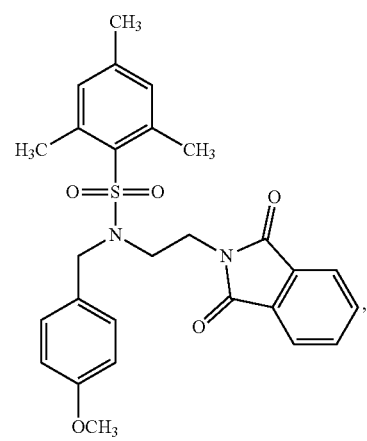

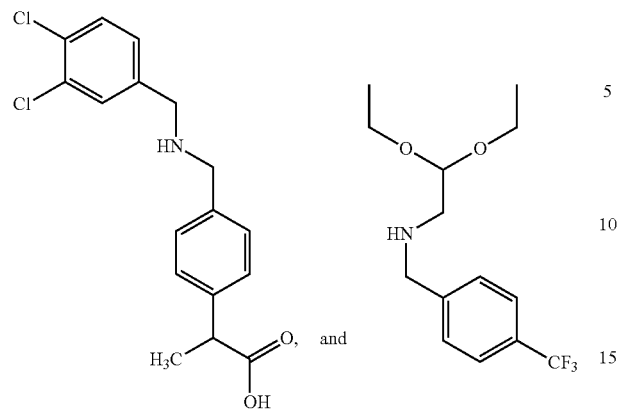

or a pharmaceutically acceptable salt or derivative thereof.

In other embodiments described herein, a composition is provided of the formula

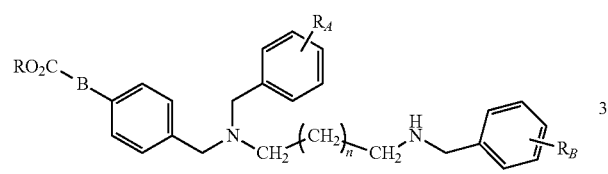

or a pharmaceutically acceptable salt thereof, wherein

B is a bond or $(CH_2)_x$ where x is 1, 2, 3, or 4;

n is 1, 2, or 3;

R is C1-C6 alkyl or hydrogen;

$R_A$ represents from 1 to 4 substituents independently selected in each instance from the group consisting of F and $CF_3$; and $R_B$ is C1-C6 alkyl, F, Cl, Br, CN, or $CF_3$.

In various embodiment described herein, another composition is provided. The composition comprises a compound selected from the group consisting of

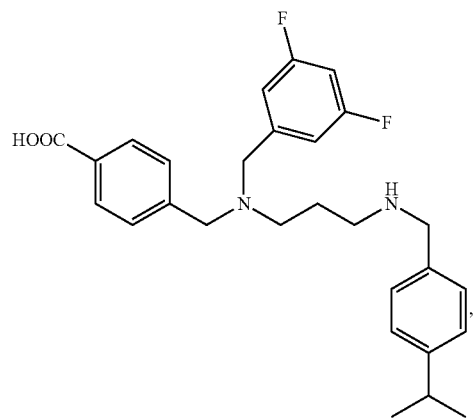
9S

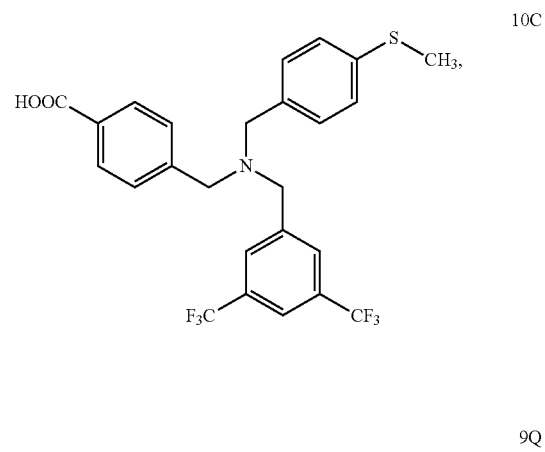
10C

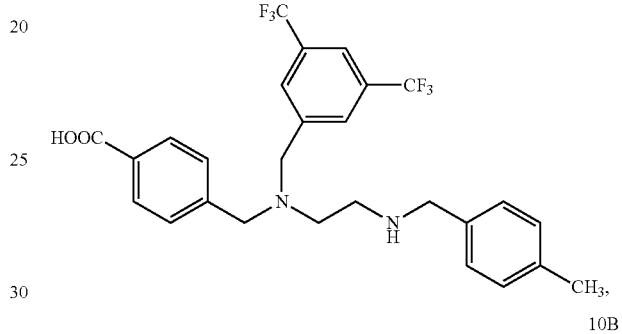
9Q

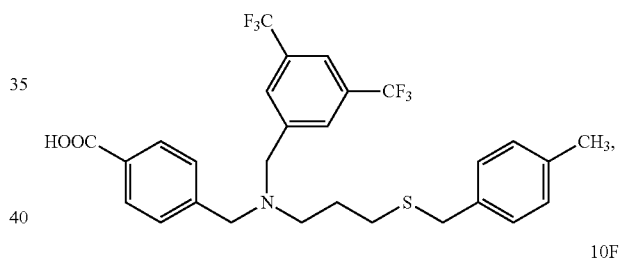
10B

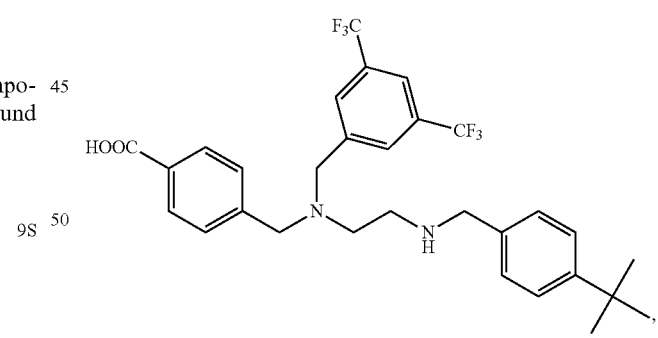
10F

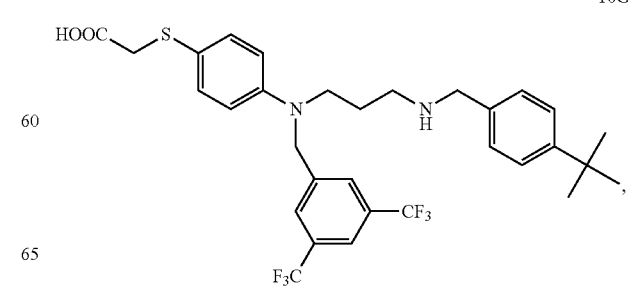
10G

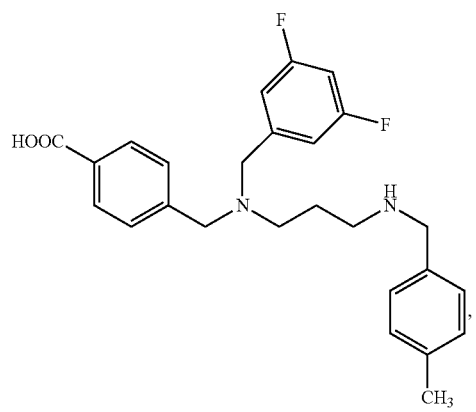
9R
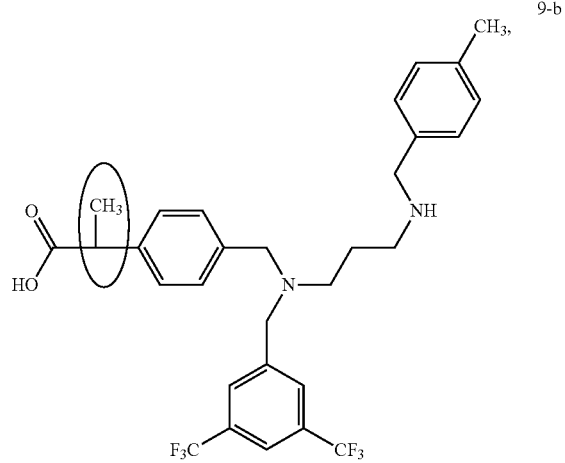
9-b
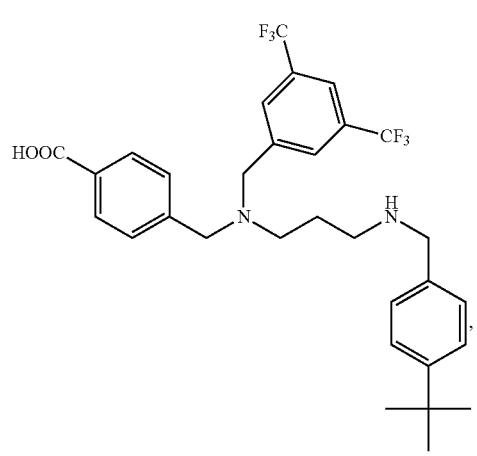
10E
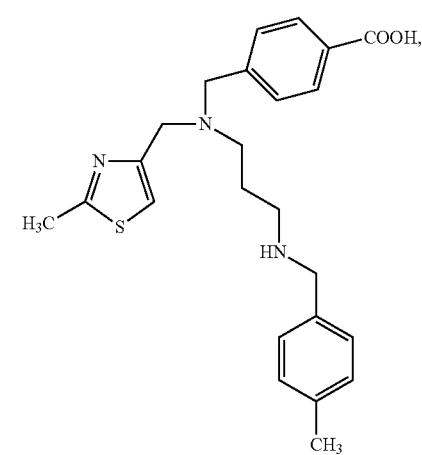
10A
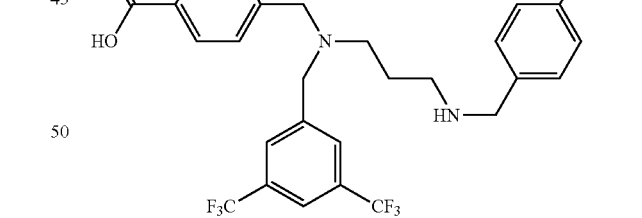
9-f
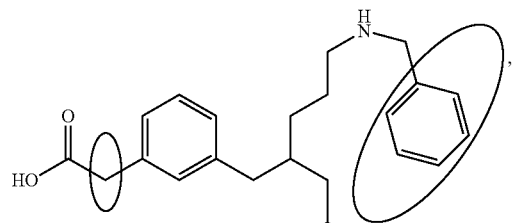
9-C
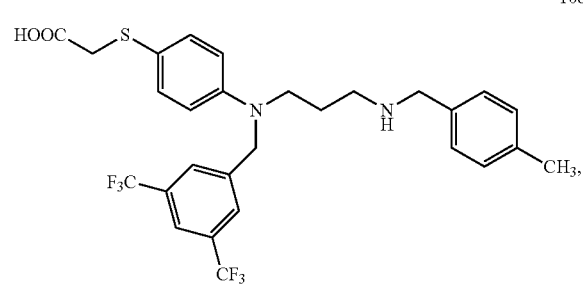
10d
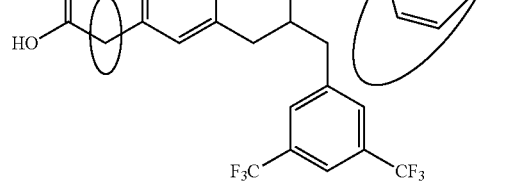
9-g

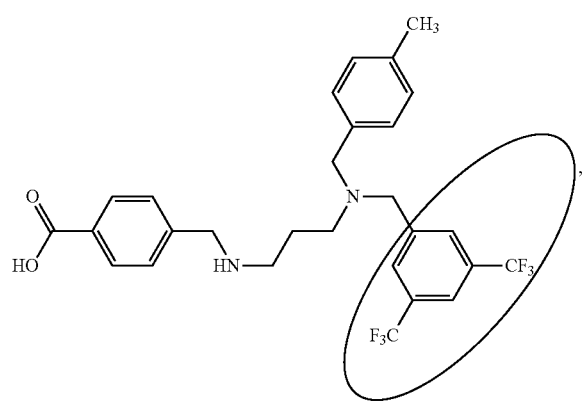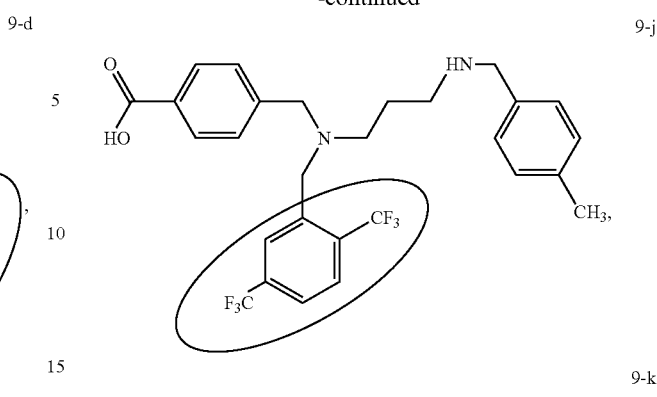

11-D (8-75)

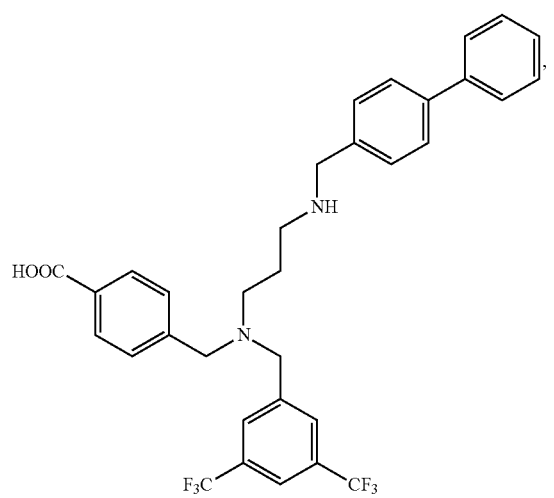

9-M

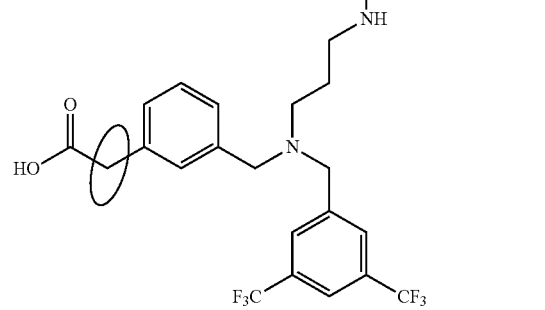

11-b (8-58a)

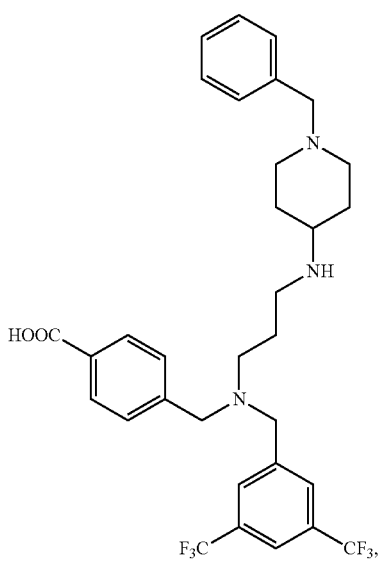

9-t

[structures shown]

or a pharmaceutically acceptable salt or derivative thereof. Such compounds can be made according to known processes in the art.

In other embodiments, a pharmaceutical formulation is provided. The pharmaceutical formulation comprises a therapeutically effective amount of a compound of any of the described compounds or formulas described herein, or a pharmaceutically acceptable salt or derivative thereof, and one or more pharmaceutically acceptable carriers.

In other embodiments, a method of treating diabetes mellitus in a patient in need thereof is provided. The method comprises the step of administering a composition to the patient, wherein the composition comprises a compound of any of the described compounds or formulas described herein, or a pharmaceutically acceptable salt or derivative thereof, and wherein the administration results in improvement of at least one symptom associated with diabetes mellitus in the patient.

In yet other embodiments, a method of treating Alzheimer's disease in a patient in need thereof is provided. The method comprises the step of administering a composition to the patient, wherein the composition comprises a compound of any of the described compounds or formulas described herein, or a pharmaceutically acceptable salt or derivative thereof, and wherein the administration results in improvement of at least one symptom associated with Alzheimer's disease in the patient.

In yet other embodiments, a method of improving insulin sensitivity in a patient is provided. The method comprises the step of administering a composition to the patient, wherein the composition comprises a compound of any of the described compounds or formulas described herein, or a pharmaceutically acceptable salt or derivative thereof, and wherein the administration results in an increase in insulin sensitivity in the patient.

In other embodiments, a method of improving glucose utilization in a patient is provided. The method comprises the step of administering a composition to the patient, wherein the composition comprises a compound of any of the described compounds or formulas described herein, or a pharmaceutically acceptable salt or derivative thereof, and wherein the administration results in an increase in glucose utilization in the patient.

In yet other embodiments, a method of improving a cognitive deficit in a patient is provided. The method comprises the step of administering a composition to the patient, wherein the composition comprises a compound of any of the described compounds or formulas described herein, or a pharmaceutically acceptable salt or derivative thereof, and wherein the administration results in an improvement in a cognitive deficit in the patient.

In various aspects, the compounds of the present disclosure are compounds of the following chemical structures:

("Compound 9")

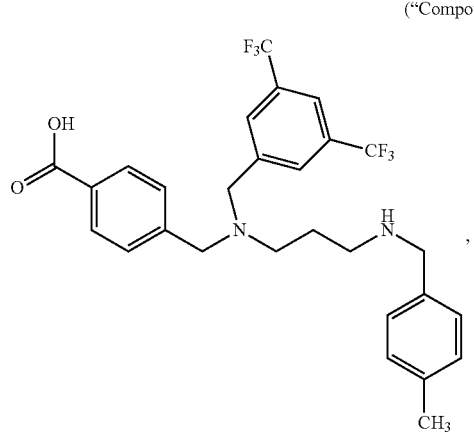

("Compound 4-23")

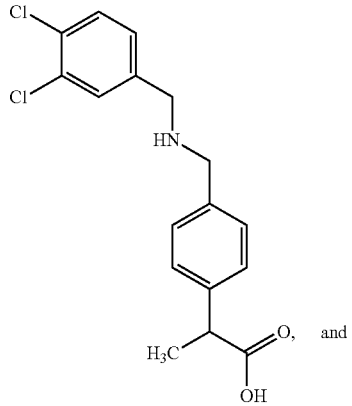

("Compound 3-121")

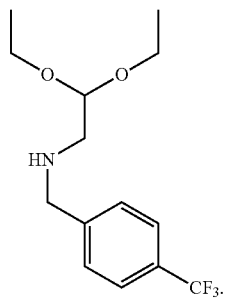

("Compound 3-91")

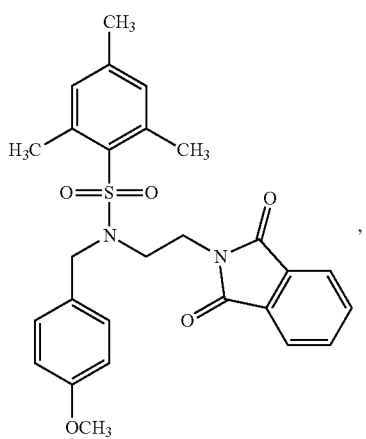

For ease of reference, the compounds of the above structures may be referred to herein as "Compound 9," "Compound 3-91," "Compound 4-23," and "Compound 3-121," respectively. It will be understood that, in the practice of the present disclosure, reference to "Compound 9" means Compound 9, pharmaceutically acceptable salts thereof, or derivatives thereof. The same nomenclature applies to "Compound 3-91," "Compound 4-23," and "Compound 3-121." Furthermore, the same nomenclature applies to any of the other compounds described herein.

Pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol. 66, No. 1, January 1977.

In other aspects, the compounds of the present disclosure are of the formula

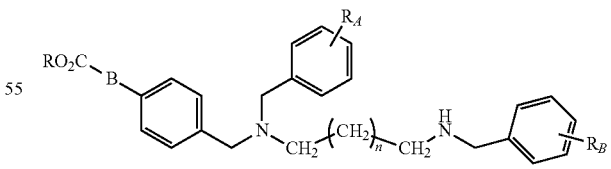

or a pharmaceutically acceptable salt thereof, wherein
B is a bond or $(CH_2)_x$ where x is 1, 2, 3, or 4;
n is 1, 2, or 3;
R is C1-C6 alkyl or hydrogen;
$R_A$ represents from 1 to 4 substituents independently selected in each instance from the group consisting of F and $CF_3$; and
$R_B$ is C1-C6 alkyl, F, Cl, Br, CN, or $CF_3$.

As used herein, the term "alkyl" includes a chain of carbon atoms, which is optionally branched. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, and the like.

In each of the foregoing and each of the following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to be a description of such hydrates and/or solvates, including pharmaceutically acceptable solvates.

In each of the foregoing and each of the following embodiments, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non crystalline and/or amorphous forms of the compounds.

As used herein, the term "solvates" refers to compounds described herein complexed with a solvent molecule. It is appreciated that compounds described herein may form such complexes with solvents by simply mixing the compounds with a solvent, or dissolving the compounds in a solvent. It is appreciated that where the compounds are to be used as pharmaceuticals, such solvents are pharmaceutically acceptable solvents. It is further appreciated that where the compounds are to be used as pharmaceuticals, the relative amount of solvent that forms the solvate should be less than established guidelines for such pharmaceutical uses, such as less than International Conference on Harmonization (ICH) Guidelines. It is to be understood that the solvates may be isolated from excess solvent by evaporation, precipitation, and/or crystallization. In some embodiments, the solvates are amorphous, and in other embodiments, the solvates are crystalline.

In various aspects, the compounds of the present disclosure may also include one or more of the following compound structures:

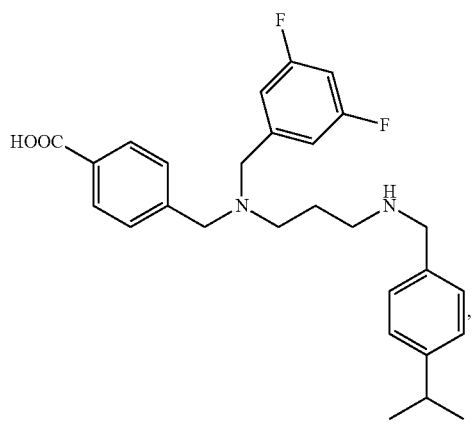

9S

-continued

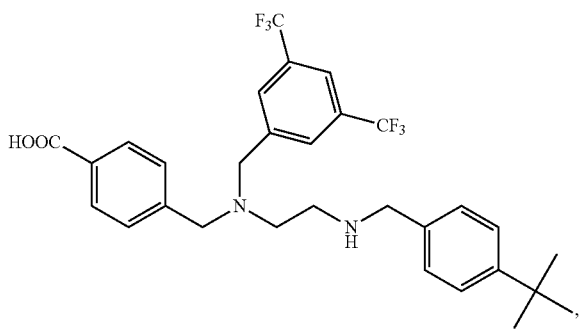

10F

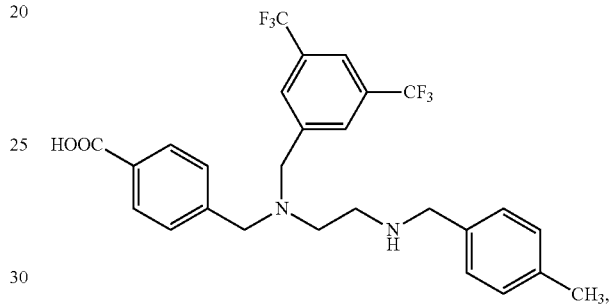

9Q

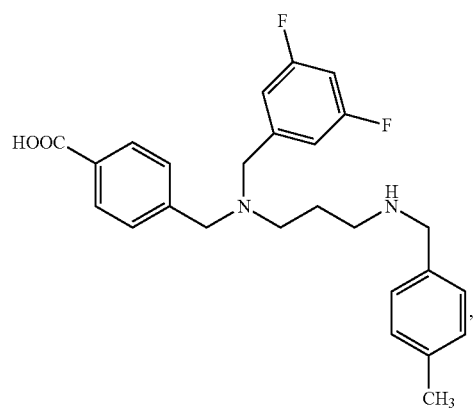

9R

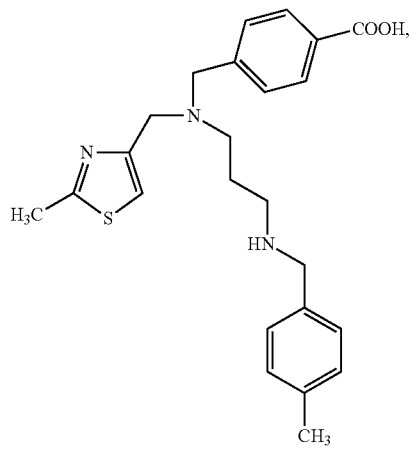

10A

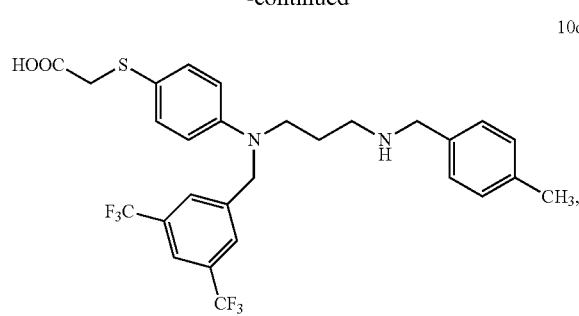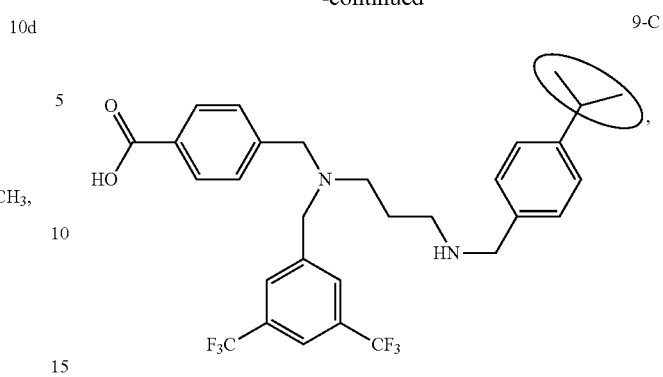

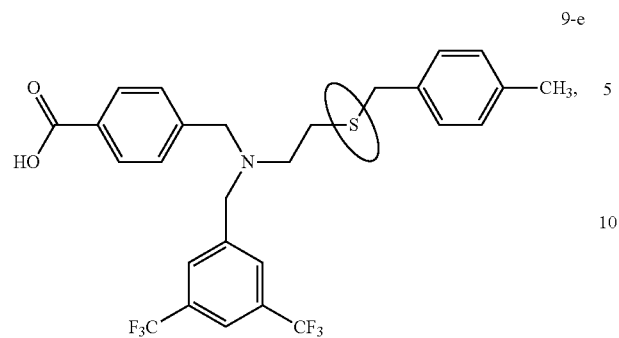
9-e
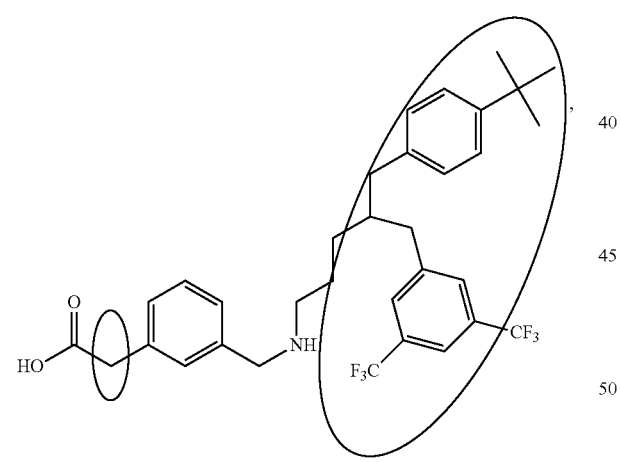
9-f
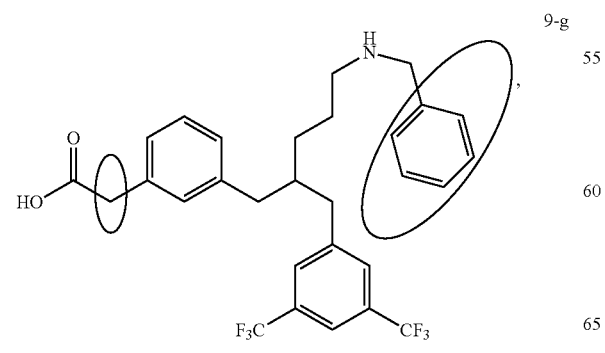
9-k
9-g
9-h
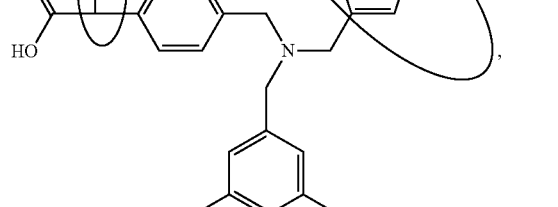
9-L
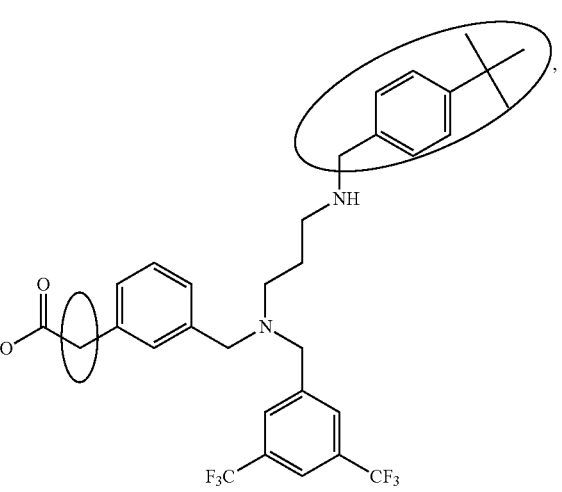
9-i
9-M
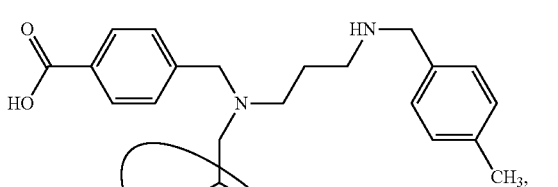

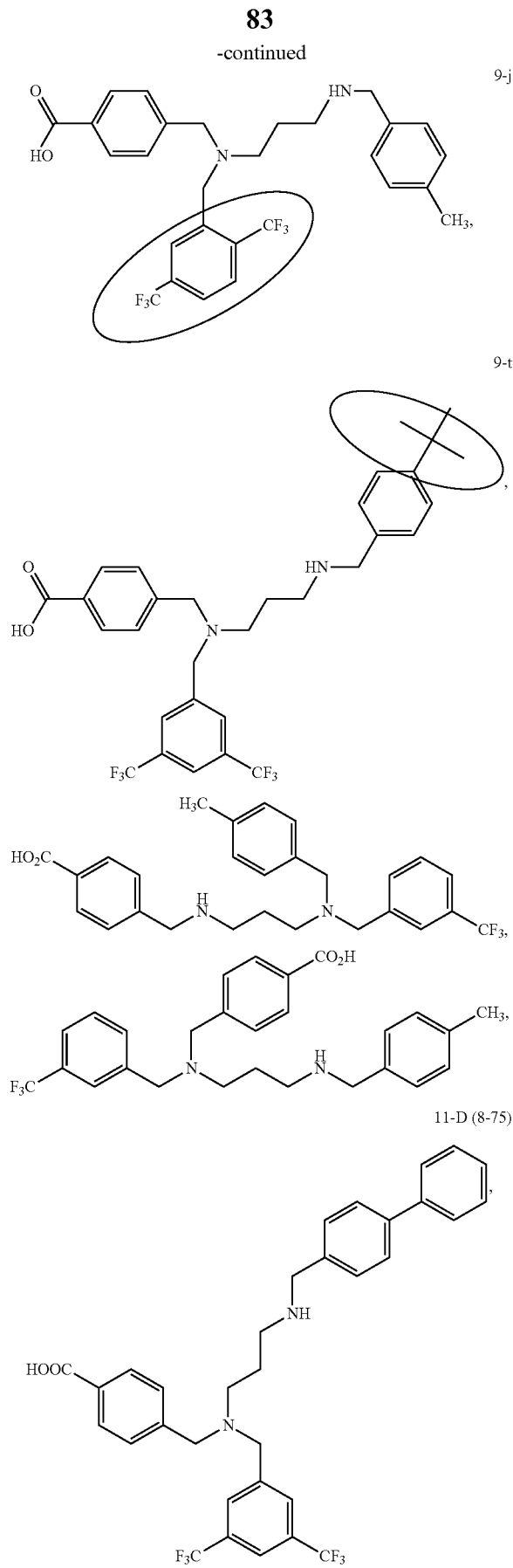

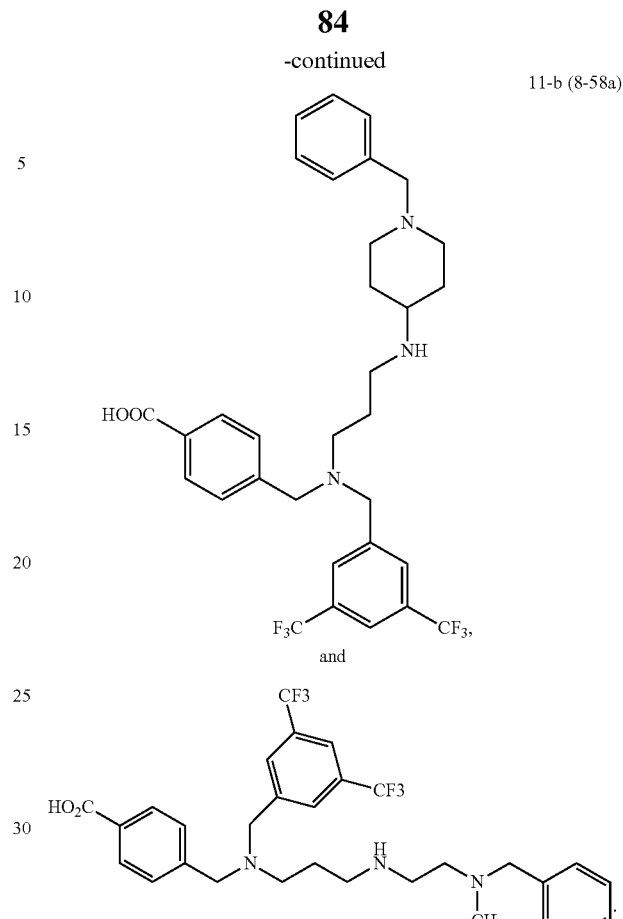

Any of the compounds described herein, and their pharmaceutically acceptable salts or derivatives, may be prepared as a pharmaceutical formulation for systemic administration. Such pharmaceutical formulations and processes for making the same are known in the art for both humans and non-human mammals. See, e.g., REMINGTON: THE SCIENCE AND PRACTICE OF PHARMACY, (A. Gennaro, et al., eds., 19th ed., Mack Publishing Co., 1995). The pharmaceutical formulation may further comprise at least one additional active ingredient.

In various aspects, the compounds of the present disclosure are agonists of PPARδ. As used herein, the term "agonist" refers to the ability of a compound to interact with a receptor and evoke a maximal effect. This effect is known as the intrinsic efficacy. In contrast, "partial agonists" interact with a receptor but produce a less than maximal response. As used herein, the term "PPARδ" refers to the Peroxisomal Proliferator Activating Receptor beta or delta (PPAR-β or PPAR-δ), also known as NR1C2 (nuclear receptor subfamily 1, group C, member 2). In certain embodiments, the compounds have a specified binding affinity. As used herein, the term "binding affinity" has its generally accepted meaning in the art, for example a measure of the intrinsic binding strength of the reaction between the compounds and the PPARδ receptor. In some embodiments, the compound has a binding affinity between −10.0 and −12.0 kcal/mol.

In other embodiments, the compounds bind with an amino acid residue of the PPARδ binding pocket. As used herein, the term "binding pocket" refers to a region of a molecule or molecular complex (such as a receptor) that, as a result of its shape, favorably associates with another chemical entity or compound. In some embodiments, the amino acid residue is selected from the group consisting of Cys285, Thr288, Thr289, Leu330, Val334, Leu339, Leu353, and Phe368. In yet other embodiments, the binding between the compound and the amino acid residue is a hydrogen bond.

In various aspects, the compounds of the present disclosure are agonists of PPARγ. As used herein, the term "PPARγ" refers to the Peroxisomal Proliferator Activating Receptor gamma (PPAR-γ or PPARG), also known as the glitazone receptor, or NR1C3 (nuclear receptor subfamily 1, group C, member 3). In certain embodiments, the compounds have a specified binding affinity. In some embodiments, the compound has a binding affinity between −10.0 and −12.0 kcal/mol.

In other embodiments, the compounds bind with an amino acid residue of the PPARγ binding pocket. In some embodiments, the amino acid residue is selected from the group consisting of Leu228, Cys285, Gln286, Arg288, Ser289, Glu295, Met329, Leu330, Ser342, Glu343, Phe363, and His 449. In yet other embodiments, the binding between the compound and the amino acid residue is a hydrogen bond.

In certain aspects, the compound is an agonist of PPARδ and an agonist of PPARγ. In other aspects, the compound permeates the blood-brain barrier. As used herein, the term "blood-brain barrier" has its generally accepted meaning in the art, such as the selective permeability barrier that separates the circulating blood from the brain extracellular fluid (BECF) in the central nervous system (CNS).

In various aspects of the present disclosure, methods are provided. In some embodiments, a method of treating diabetes mellitus in a patient in need thereof is provided. As used herein, the term "diabetes mellitus" has its generally accepted meaning in the art, such as a variable disorder of carbohydrate metabolism caused by a combination of hereditary and environmental factors and usually characterized by inadequate secretion or utilization of insulin, by excessive urine production, by excessive amounts of sugar in the blood and urine, and by thirst, hunger, and loss of weight. In some embodiments, the diabetes mellitus is Type 1 diabetes mellitus. In other embodiments, the diabetes mellitus is Type 2 diabetes mellitus.

In certain aspects, the methods include the step of administering a therapeutically effective amount of a composition to a patient. As used herein, the term "administering" refers to any suitable means of delivering the composition of the present disclosure the patient. In some embodiments, the administration is a parenteral administration. Suitable routes for such parenteral administration include intravenous, intraarterial, intraperitoneal, intrathecal, intradermal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques. In other embodiments, the administration is an oral administration. The term "oral administration" refers to the provision of a composition via the mouth through ingestion, or via some other part of the gastrointestinal system including the esophagus. Examples of oral dosage forms include tablets (including compressed, coated or uncoated), capsules, hard or soft gelatin capsules, pellets, pills, powders, granules, elixirs, tinctures, colloidal dispersions, dispersions, effervescent compositions, films, sterile solutions or suspensions, syrups and emulsions and the like.

As used herein, the term "therapeutically effective amount" refers to an amount which gives the desired benefit to a patient and includes both treatment and prophylactic administration. The amount will vary from one patient to another and will depend upon a number of factors, including the overall physical condition of the patient and the underlying cause of the condition to be treated. As used herein, the term "composition" can refer to any of the compounds described in the present disclosure. As used herein, the term "patient" refers to an animal, for example a human.

In some embodiments, the administration results in improvement of at least one symptom associated with diabetes mellitus in the patient. There are many symptoms associated with diabetes mellitus that are known in the art, for example: impaired insulin sensitivity, impaired glucose utilization, excessive thirst and appetite, increased urination, fatigue, nausea, vomiting, blurred vision, dry mouth, slow-healing sores or cuts, and itching skin.

In some embodiments, the method is associated with improved insulin sensitivity in the patient. As used herein, the term "insulin-sensitivity" refers to ability of a patient to reduce serum glucose levels in response to increased levels of insulin.

In other embodiments, the method is associated with improved glucose utilization in the patient. As used herein, the term "glucose utilization" refers to the absorption of glucose from the blood by muscle and fat cells and utilization of the sugar for cellular metabolism. The uptake of glucose into cells is stimulated by insulin.

In yet other embodiments, the method is associated with improved induction of mitochondrial biogenesis in the patient. The term "mitochondrial biogenesis" refers to processes of growth, amplification and healthy maintenance of the mitochondria.

In some embodiments, the method is associated with improved insulin signaling in the brain of the patient. Insulin signaling in the brain is a component of cognitive process in an animal, and can be monitored by any method known in the art.

In some embodiments, the method is not associated with lipid accumulation in the patient. Lipid accumulation refers to, for example, an increase in the level of total lipids, an increase in at least one type of fatty acid (e.g., very long chain fatty acids), or an increase in cholesterol or lipoproteins (e.g., chylomicrons, very-low-density lipoprotein (VLDL), intermediate-density lipoprotein (IDL), low-density lipoprotein (LDL), and high-density lipoprotein (HDL)). In other embodiments, the method does not induce an increase in lipid accumulation in the patient. In certain embodiments, the lipid accumulation is ectopic lipid accumulation. Ectopic lipid accumulation refers to lipid accumulation in non-adipose tissue and is believed to be an important consideration in diabetes management.

In other embodiments, the method is not associated with adverse cardiovascular event in the patient. As used herein, the term "adverse cardiovascular event" refers, generally, to a disorder or disease of the cardiovascular system resulting from progressive vascular damage. Although the event may have a rather sudden onset, it can also refer to a progressive worsening of such a disorder or disease. Examples of cardiovascular events include, without limitation: claudication, cardiac arrest, myocardial infarction, ischemia, stroke, transient ischemic attacks, worsening of angina, heart failure, congestive heart failure, or left ventricular hypertrophy. Examples of progressive vascular diseases are those that affect the cerebral, coronary, renal, or peripheral circulations. In one embodiment, the adverse cardiovascular event is heart failure.

In another embodiment, the adverse cardiovascular event is myocardial infarction.

In other aspects, a method of treating Alzheimer's disease in a patient in need thereof is provided. The previously described embodiments of the method of treating diabetes mellitus in a patient are applicable to the method of treating Alzheimer's disease in a patient described herein.

In some embodiments, the method is associated with improvement of a cognitive deficit in the patient. The term "cognitive deficit" may include one or more of the following: loss of or important deterioration in short-term and/or long-term memory or loss of or important deterioration in learning ability, loss of executive functions (rational decision making, judgment), decline in the ability to carry out activities of daily living, personality changes, and hallucinations or delusions. Cognitive decline in learning means significantly prolonged period of time required to acquire new skills or information, and a decline in memory means significantly shortened periods for retaining such skills or information. In certain embodiments, the cognitive deficit is memory impairment. Methods to evaluate cognitive deficit can be performed according to known methods in the art.

In other embodiments, the method is associated with an improvement in cognition in the patient. The term "cognition" as used herein refers to the mental process of knowing, including aspects such as awareness, perception, reasoning, and judgment. It may also be referred to as the operation of the mind by which one becomes aware of objects of thought or perception, including all aspects of perceiving, thinking, and remembering. Methods to evaluate cognition can be performed according to known methods in the art.

In yet other embodiments, the method is associated with central PPARγ activation. The term "central PPARγ activation" refers to activation of PPARγ receptors in the central nervous system of the patient, for example in the brain of the patient. In some embodiments, the central PPARγ activation is in the hippocampus of the patient. Methods to evaluate central PPARγ activation can be performed according to known methods in the art.

In some embodiments, the method is associated with an improvement in synaptic plasticity in the patient. Synaptic plasticity refers to the cellular process that results in lasting changes in the efficacy of neuro-transmission. More specifically, it refers to the variability of the strength of a signal transmitted through a synapse. Methods to evaluate synaptic plasticity can be performed according to known methods in the art.

In other embodiments, the method is associated with a decrease in Tau phosphorylation in the hippocampus of the patient. Tau hyperphosphorylation represents a classic hallmark for the evidence of Alzheimer's disease due to the involvement of Tau in microtubule disassembly and neuronal degeneration. The mechanism underlying the Aβ-induced Tau hyperphosphorylation as mediated by impaired insulin signal transduction has been delineated, finding that pAKT and GSKp upon insulin stimulation was compromised under Aβ conditions. Furthermore, in post mortem Alzheimer's brain, reduced mediators have been found in the insulin signaling cascade including the insulin receptor, insulin receptor substrate (IRS-1), and the pro-survival protein AKT. Methods to evaluate Tau phosphorylation can be performed according to known methods in the art.

In yet other embodiments, the method is associated with a decrease in PTEN expression in the hippocampus of the patient. The term "PTEN" refers to the tumor suppressor phosphatase and tensin homologue deleted on chromosome 10. PTEN acts as a tumor suppressor gene through the action of its phosphatase protein product, which is involved in the regulation of the cell cycle. Methods to evaluate PTEN expression can be performed according to known methods in the art.

In certain embodiments, the method is associated with an increase in BDNF expression in the hippocampus of the patient. The term "BDNF" refers to brain-derived neurotropic factor, a member of the "neurotrophin" family of growth factors found in the brain and the periphery of patients. BDNF acts on certain neurons of the central nervous system and the peripheral nervous system, helping to support the survival of existing neurons and encourage the growth and differentiation of new neurons and synapses. In the brain, it is active in the hippocampus, cortex, and basal forebrain, and is important for long-term memory. Methods to evaluate BDNF expression can be performed according to known methods in the art.

In other aspects, a method of improving insulin sensitivity in a patient is provided. The previously described embodiments of the method of treating diabetes mellitus in a patient are applicable to the method of improving insulin sensitivity described herein.

In various aspects, method of improving glucose utilization in a patient is provided. The previously described embodiments of the method of treating diabetes mellitus and the method of improving insulin sensitivity are applicable to the method of improving glucose utilization described herein.

In certain aspects, a method of improving a cognitive deficit in a patient is provided. The previously described embodiments of the method of treating Alzheimer's disease are applicable to the method of improving a cognitive deficit in a patient described herein.

In other aspects, a pharmaceutical formulation comprising a therapeutically effective amount of a compound, or a pharmaceutically acceptable salt or derivative thereof, and one or more pharmaceutically acceptable carriers is provided. The previously described embodiments of the compounds are applicable to the pharmaceutical formulations described herein. "Compound 9," "Compound 3-91," "Compound 4-23," and "Compound 3-121," and their pharmaceutically acceptable salts or derivatives, may be prepared as a pharmaceutical formulation for systemic administration. Such pharmaceutical formulations and processes for making the same are known in the art for both humans and non-human mammals. See, e.g., REMINGTON: THE SCIENCE AND PRACTICE OF PHARMACY, (A. Gennaro, et al., eds., 19th ed., Mack Publishing Co., 1995). The pharmaceutical formulation may further comprise at least one additional active ingredient.

As used herein, the term "carrier" means any ingredient other than the active component(s) in a formulation. The choice of carrier may depend on factors such as the particular mode of administration, the effect of the carrier on solubility and stability, and the nature of the dosage form.

In various embodiments, the pharmaceutical formulation is suitable for administration to a patient at a specified dose range. In one embodiment, pharmaceutical formulation is suitable for administration at a dose of about 0.001 to about 1000 mg of the compound per kg of patient body weight. In another embodiment, the pharmaceutical formulation is suitable for administration at a dose of about 0.001 to about 100 mg of the compound per kg of patient body weight. In yet another embodiment, the pharmaceutical formulation is suitable for administration at a dose of about 0.01 to about 100 mg of the compound per kg of patient body weight. In one embodiment, the pharmaceutical formulation is suitable for administration at a dose of about 0.1 to about 100 mg of the compound per kg of patient body weight. In another embodiment, the pharmaceutical formulation is suitable for administration at a dose of about 0.1 to about 10 mg of the compound per kg of patient body weight. In yet another embodiment, the pharmaceutical formulation is suitable for administration at a dose of about 1 to about 5 mg of the compound per kg of patient body weight. In one embodiment, the pharmaceutical formulation is suitable for administration at a dose of about 2 mg of the compound per kg of patient body weight. In another embodiment, the pharmaceutical formulation is suitable for administration at a dose of about 3 mg of the compound per kg of patient body weight. In yet another embodiment, the pharmaceutical formulation is suitable for administration at a dose of about 4 mg of the compound per kg of patient body weight. In another embodiment, the pharmaceutical formulation is suitable for administration at a dose of about 5 mg of the compound per kg of patient body weight.

While the invention is susceptible to various modifications and alternative forms, specific embodiments are herein described in detail. It should be understood, however, that there is no intent to limit the invention to the particular forms described, but on the contrary, the intention is to cover all modifications, equivalents, and alternatives falling within the scope of the invention.

EXAMPLE 1

Preparation of an Exemplary Novel Compound: "Compound 9"

A scheme to prepare an exemplary novel compound, "Compound 9," is shown and explained below. Reagents and conditions for the scheme are as follows: (a) Fmoc, $Na_2CO_3$, dioxane, water, at 0° C.; (b) 2-chlorotrityl chloride resin, DIPEA, COMU, methanol, DCM, DMF; (c) 3,5-bis (trifluoromethyl) benzyl bromide, DIPEA, NaH, DCM; (d) DCM, DMF, piperidine, 1:1:2; (e) 3-bromopropylamine hydrobromide, Fmoc chloride, Na2CO3, dioxane, water at 0° C.; (f) (8), DIPEA, NaH, DCM, DMF; (g) 4-methylbenzyl bromide, DIPEA, NaH, DCM, DMF; (h) DCM, DMF, piperidine, 1:1:2; (i) 90% TFA, DCM.

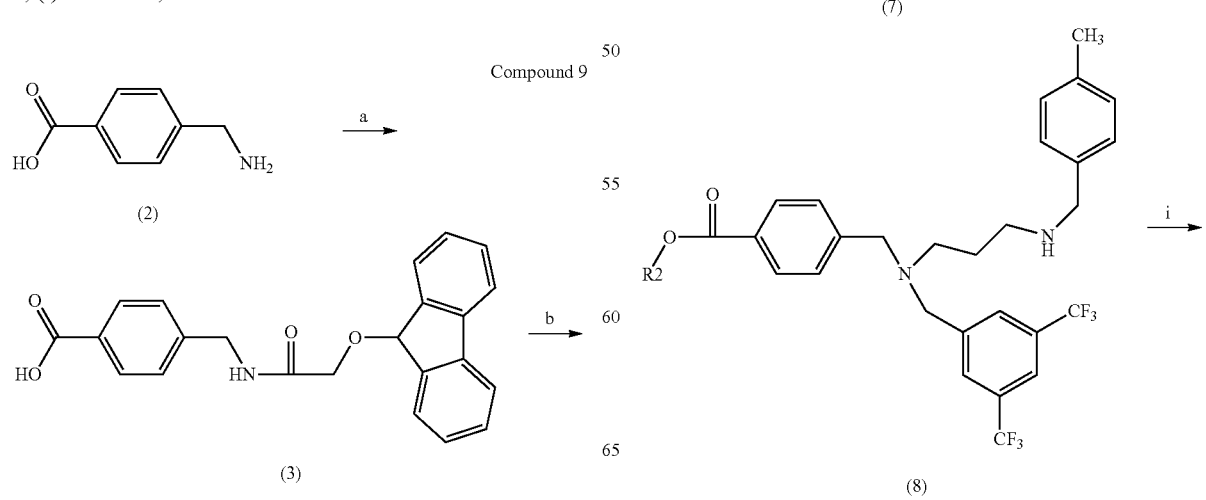

Compound 9

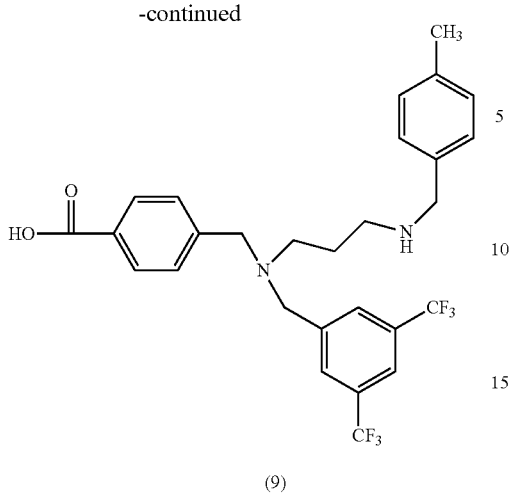

(9)

Treatment of 4-(aminomethyl)benzoic acid 2 with Fmoc chloride, Na₂CO₃, dioxane, water, at 0° C. provided 3. Nucleo-philic substitution of 3 with 2-chlorotrityl chloride resin, D-IPEA, COMU, methanol, DCM, and DMF provided intermediate 4.

Subsequent treatment of 4 with 3,5-bis(trifluoromethyl) benzyl bromide, DIPEA, sodium hydride and DCM, followed by deprotection of Fmoc using DCM, DMF, Piperidine in a 1:1:2 ratio, yielded 5. The Fmoc protected amino propyl bromide intermediate 6 was created by reacting 3-bromopropylamine hydrobromide with Fmoc chloride, sodium carbonate, dioxane, water, at 0° C.

The intermediate compound 6 was reacted with 5, DIPEA, sodium hydride, DCM, DMF to generate 7. 4-Methylbenzyl bromide, DIPEA, sodium hydride, DCM, DMF were reacted with 7 for 12 hours before subsequent treatment with DCM, DMF, Piperidine in a 1:1:2 ratio to remove the Fmoc and generate 8. The last step involved to generate the final compound 9 was to clip it from the resin using 90% TFA and DCM for 1.5 h to dissociate resin from final compound 9.

EXAMPLE 2

Preparation of an Exemplary Novel Compound: "Compound 3-121"

A scheme to prepare an exemplary novel compound, "Compound 3-121," is shown and explained below. Reagents and conditions for the scheme are as follows: (a) 2-mesitylenesulfonyl chloride, 10% NaOH, CH₂Cl₂ 24 h; (b) 4-(trifluoro-methyl) benzyl bromide, NaH, DMF; (c) HBR solution of 33% acetic acid, phenol, EtoAC.

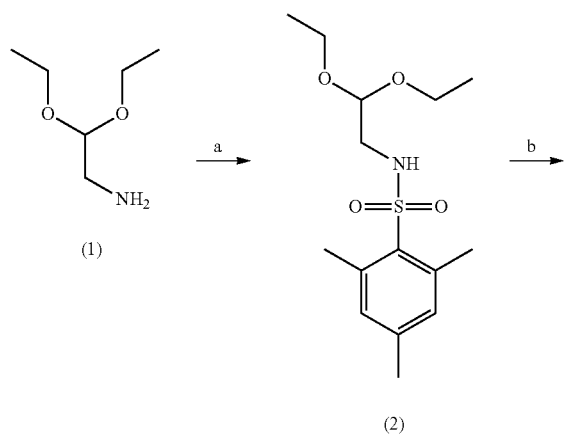

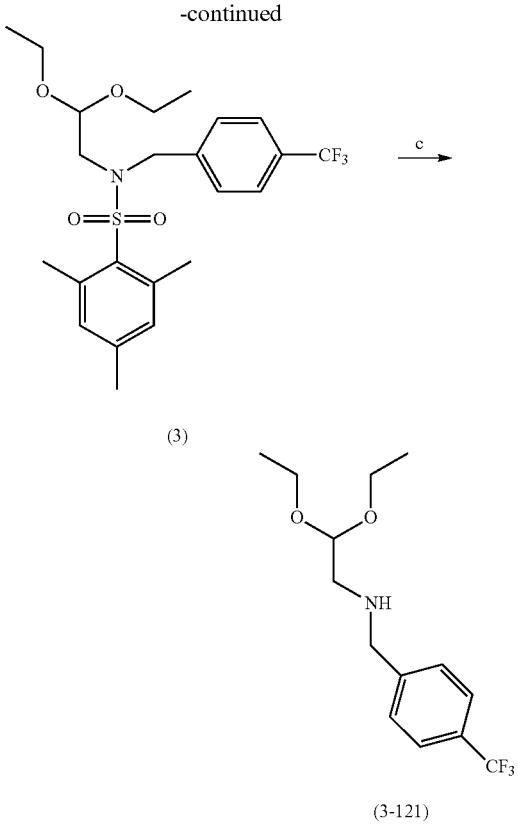

Treatment of aminoacetaldehyde diethyl acetal 1 with 2-mesitylenesulfonyl chloride, 10% NaOH, CH2Cl2 for 24 hours, provided 2. Nucleophilic substitution of 4-(triflouromethyl)benzyl bromide, NaH, DMF, under nitrogen, with 2 yielded 3. The last step required to generate 3-121 was reacting 3 with HBr solution (33% acetic acid), phenol, ethyl acetate, for 24 hours, to create 3-121.

EXAMPLE 3

Computational Methods for Docking Simulation of Novel Compounds

AutoDock Vina (O. Trott, A. J. Olson, "AutoDock Vina: improving the speed and accuracy of docking with a new scoring function, efficient optimization and multithreading," *Journal of Computational Chemistry*, 31 (2010) 455-461) was used to dock known and proposed agonists of PPARδ and PPARγ. Initial Cartesian coordinates for the protein-ligand structures were derived from a reported 1.95 Å crystal structure of PPARγ (PDB ID: 3ET3) and a 2.00 Å crystal structure of PPARδ (PDB ID: 3GZ9). In the case of PPARγ, the present model included the active site and all residues within 15 Å of it. Clipped residues were capped with acetyl or N-methylamine. The reduced PPARγ model consisted of ~2800 atoms and 162 residues out of 275 residues. The PPARδ model used the protein in its entirety.

The protein targets were prepared for molecular docking simulation by removing water molecules and bound ligands. Auto-Dock Tools (ADT) was used to prepare and analyze the docking simulations for the AutoDock Vina program. All ligands were constructed using PyMOL with subsequent geometry optimizations carried out using the semi empirical method PDDG/PM3 and the BOSS program. Polar hydrogens were added, and in the case of AutoDock, Gasteiger charges were assigned. Nonpolar hydrogen was subsequently merged.

The protonation state of the ligands was adjusted to the species assumed predominant at physiological pH, specifically, carboxylic acid moieties were deprotonated. Conjugate gradient minimizations of the systems were performed using MCPRO15 and GROMACS. A grid was centered on the catalytic active site region and included all amino acid residues within a box size set at 26 A for AutoDock Vina.

Standard flexible protocols of AutoDock Vina using the iterated local search global optimizer algorithm were employed to evaluate the binding affinities of the molecules and interactions with the receptors. All ligands and active site residues, as defined by the box size used for the receptors, were set to be rotatable. Calculations were carried out with the exhaustiveness of the global search set to 100, number of generated binding modes set to 20, and maximum energy difference between the best and the worst binding modes set to 5. Following completion of the docking search, the final compound pose was located by evaluation of AutoDock Vina's empirical scoring function where the conformation with the lowest docked energy value was chosen as the best.

The PPAR ligand binding domain resembles a large Y-shaped cavity starting from the entrance and extending into Arm I and Arm II pockets (see FIG. 1). Arm I is substantially polar while the entrance and Arm II are primarily hydrophobic. Of the tested novel compounds, compound 9 possesses the highest binding affinity for both PPARγ and PPARδ (see Table 1).

TABLE 1

Predicted binding affinities (kcal/mol) for proposed agonists in PPARγ and PPARδ

| PPARγ | | PPARδ | |
| --- | --- | --- | --- |
| Molecule | Affinity (kcal/mol) | Molecule | Affinity (kcal/mol) |
| 9 | −12.0 | 9 | −10.8 |
| 3-91 | −11.0 | 3-91 | −10.2 |
| 4-23 | −9.2 | 4-23 | −8.6 |
| 3-121 | −7.7 | 3-121 | −8.6 |

Figure 2:
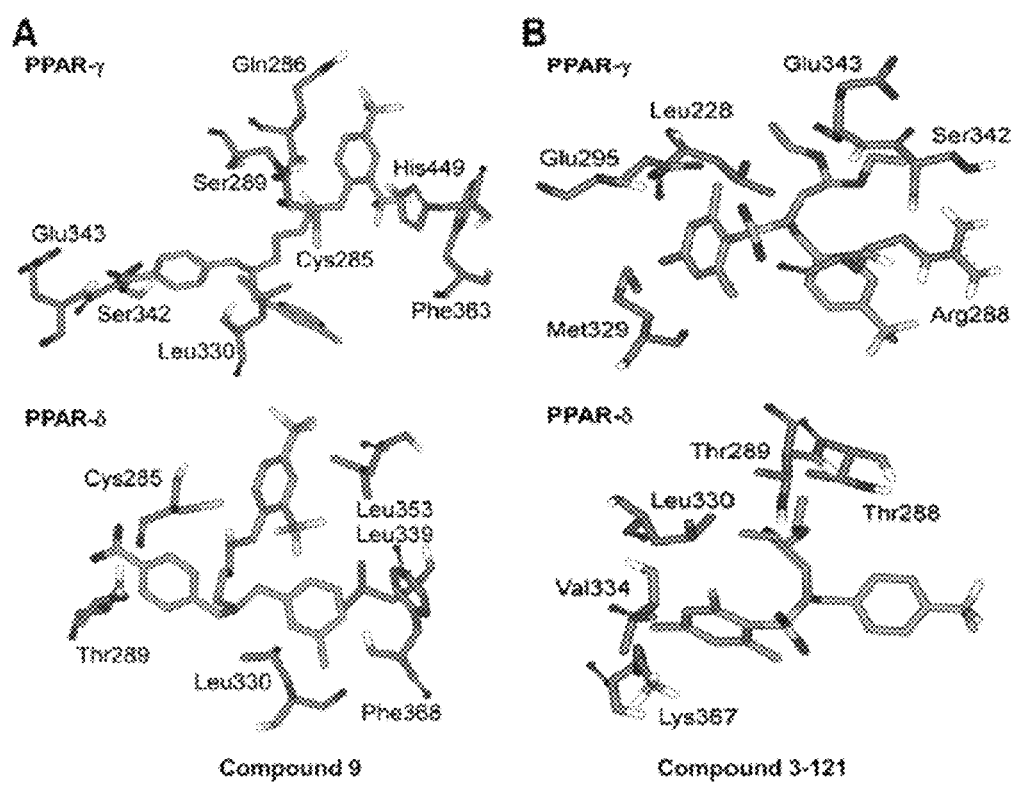
FIG. 2 shows the predicted images of compounds 9 and 3-121 bond patterns. (A) Compound 9 bound to the active site of PPARγ (top) and PPARδ (bottom) with key residues shown. (B) Compound 3-121 bound to the active site of PPARγ (top) and PPARδ (bottom) with key residues shown.

Inspection of the in silico PPARγ/compound 9 complex suggests that the carboxylate group of compound 9 forms a hydrogen bond at a distance of 2.02 A with the entrance residue Glu343 while the 2° amine donates a tighter hydrogen bond of 1.85 A with the polar Ser289 residue of Arm I (see FIG. 2A). The noncanonical X—H-p hydrogen bond has been shown to be of great importance in proteins and compound 9's trifluoromethyl disubstituted phenyl ring is revealed to accept a N—H-p hydrogen bond of ca. 2.69 A from His449. This interaction holds the ring moiety in position, making compound 9 avoid contact with Tyr473 which is ca. 4.8 A away. This residue is crucial to the stabilization of the AF2 helix H12 which allows the binding of co-activators that lead to the activation of the genes responsible for adipogenesis. These conformational changes of the PPARγ binding pocket by compound 9 selectively activates PPARγ target genes to have negligible effects on lipid accumulation while activating other genes involved in regulating fatty acid oxidation (HSL, ATGL and MCAD).

Docking studies of our compounds on PPARδ shows that the carboxylate group of the receptor forms a hydrogen bond of 3.03 A with Thr289 in Arm I which is part of the His323, His449 and Tyr473 hydrogen bond network. This site is specifically involved in the carboxylate group of fatty acids and eicosanoic acids (the endogenous ligands) binding, which are natural ligands for PPARδ in circulation. The 2° amine also donates an H-bond of 2.87 A to the Sulfur atom of the polar residue Cys285 in Arm I. Furthermore, the methyl substituted phenyl ring in compound 9 located between the entrance and Arm II and surrounded by the hydrophobic residues Leu330, Leu339 and Phe368 stabilize the ligand binding domain.

It was predicted that the ether oxygen atoms of compound 3-121 accept two hydrogen bonds of ca. 2.17 and 2.86 A from the backbone NH group of the polar residue Glu343 in the entrance region of PPARγ (see FIG. 2B). The calculations do not predict binding with any of the polar residues located in Arm I; this appears consistent with the lipid accumulation studies which demonstrate an insignificant induction of adiposity with compound 3-121 compared to full PPARγ agonists (see FIG. 5). The docking studies also predicted 3-121 to bind weakly to PPARδ due to the absence of the conserved hydrogen bonding.

Compound 3-91 was predicted to display high PPARγ activation capacity because it possesses the same binding mode as the full PPARγ agonist rosiglitazone. This was demonstrated in the docking analysis, which predicted that the PPARγ receptor forms two hydrogen bonds with the isoindoledione substituent group of 3-91, the hydrogen on His323 and a carbonyl oxygen, and the hydrogen on His449 and the nitrogen at distances of 2.38 and 2.66 A, respectively (Supplementary data S 10).

In addition, the OH group of Ser289 also forms a hydrogen bond of 2.57 A with the N of the isoindoledione substituent group. This binding mode is consistent with known full agonists, for example, rosiglitazone.

EXAMPLE 4

Binding Capacity of Novel Compounds to Peroxisome Proliferator Response Elements (PPRE)

To validate the specificity of the novel compounds towards activation of PPARγ/δ targets, we tested the compounds capacity to bind to select PPARγ/δ Peroxisome Proliferator Response Elements (PPRE). The PPRE are unique sites located in the promoter region where PPARs bind and transcriptionally activate the target genes. AP2-PPRE is the PPARγ target involved in adipocyte growth and differentiation. PDK4-PPRE is a PPARδ target involved in regulating energy metabolism in the cell. These PPREs were inserted into a PGL3 luciferase vectors containing CMV promoters (ADDGENE) using PCR. These vectors were co-transfected with RXR, PPARγ/PPARδ and p-galactosidase vectors into HEK-293 cells using Lipofectamine 2000 (Invitrogen). Relative light units (RLU) were measured using a Glomax Luminometer (Promega). Data were standardized to p-galactosidase activity using ONPG (Promega).

Figure 3:
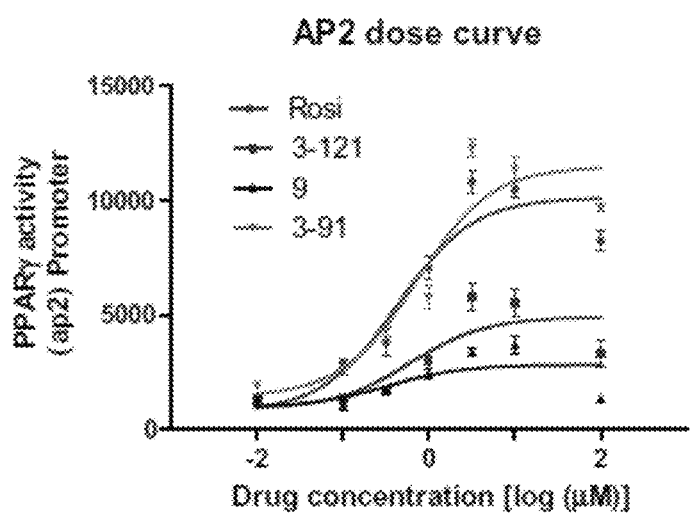
FIG. 3 shows the AP2-PPRE dose-response curve. The lipid accumulation (percent change from control) is shown for each of control, rosiglitazone, compound 3-91, compound 3-121, compound 9, and compound 4-23 over time.

FIG. 3 shows a dose-response curve of various drugs for AP2-PPRE activity. Data from luciferase assays shows that compound 3-91 and rosiglitazone (10 μM) have strong binding affinity for the AP2-PPRE. However compounds 9 and 3-121 show less binding affinity for the AP2-PPRE. Accordingly, transcriptional assays demonstrate that compound 9 minimally activates the AP2-PPRE.

Figure 4:
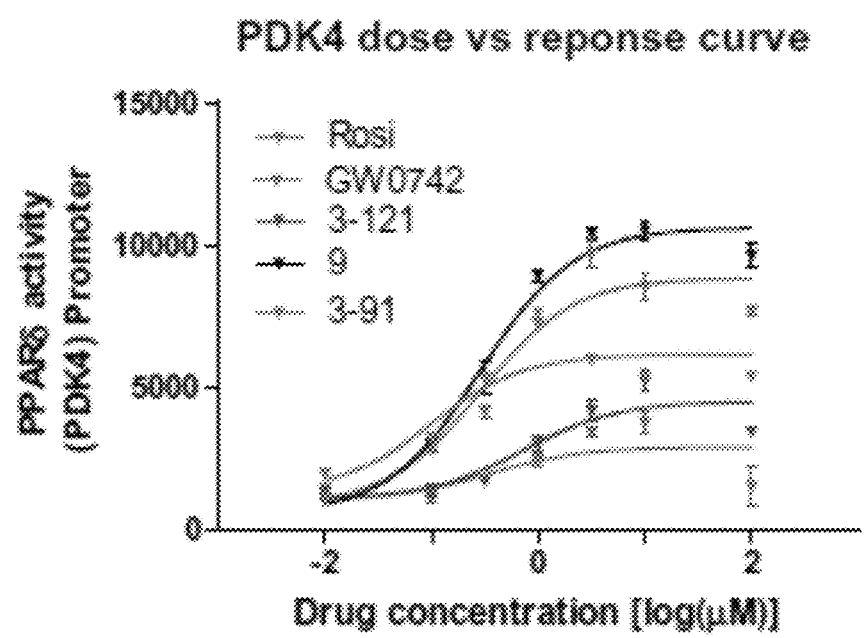
FIG. 4 shows the PDK4-PPRE dose-response curve. The PPARδ activity of the PDK4 promoter is shown for each of rosiglitazone, GW0742, compound 3-121, compound 9, and compound 3-91 at various drug concentrations [log(μM)].

The biological significance of compound modifications was also determined by luciferase assays and a PDK4-PPRE dose-response curve is shown in FIG. 4. Data from luciferase assays shows that compound 9 and GW0742 have strong binding affinity for the PDK4-PPRE, a direct PPARα target.

However, compounds 3-91 and 3-121 show less binding affinity for the PDK4-PPRE.

EXAMPLE 5

Physiological Effects of Novel Compounds Upon Lipid Accumulation

3T3L1 adipocytes were cultured and treated with the novel compounds for a period of 6 days. Lipid accumulation was determined by oil red-o staining, and measured the absorbance spectrophotometrically at a wavelength of 510 nm and standardized to total protein concentrations. Data from lipid accumulation studies were compared to cells treated with rosiglitazone (a full PPARγ agonist).

Figure 5:
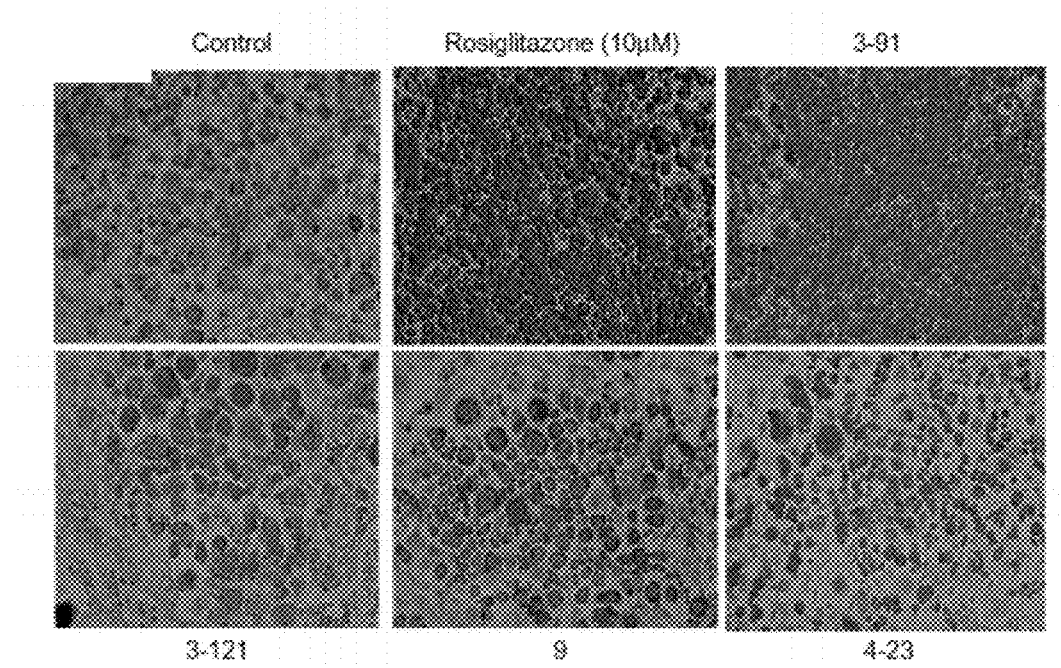
FIG. 5 shows induction of lipid accumulation in 3T3-L1 adipocytes for each of control, rosiglitazone, compound 3-91, compound 3-121, compound 9, and compound 4-23, as demonstrated by the oil red-o stain.

In the lipid accumulation assays, compound 3-91 induces lipid accumulation comparable to rosiglitazone in 3T3-L1 adipocytes, as demonstrated by the oil red-o stain (see FIG. 5). Accordingly, compound 3-91 was verified to be a strong PPARγ activator. In comparison, compounds 9, 3-121 and 4-23 induce less lipid accumulation. In particular, compound 9 demonstrates negligible effects upon lipid accumulation in adipocytes.

Figure 6:
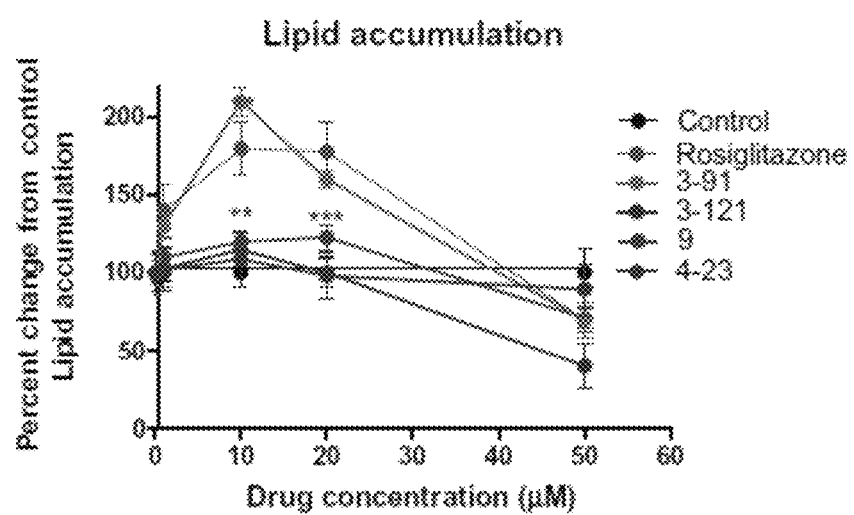
FIG. 6 shows quantification of lipid accumulation levels by measuring the absorbance at a wavelength of 510 nm and graphically represented as a percent change from vehicle treated cells (control). *P<0.05, P<0.005, *P<0.0001.

As shown in FIG. 6, lipid accumulation levels were quantitated by measuring the absorbance at a wavelength of 510 nm and graphically represented as a percent change from vehicle treated cells (control).

Figure 7:
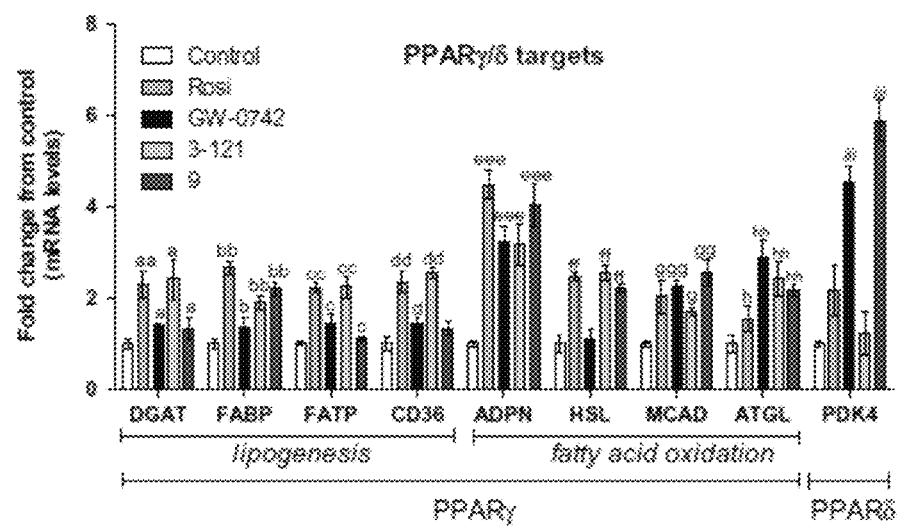
FIG. 7 shows mRNA analyses of PPARγ/δ targets. Rosiglitazone, GW0742, 3-121, and 9 (10 μM dose for all compounds) were applied to 3T3-L1 adipocytes to determine effects on PPARγ/δ target mRNA expression levels. Values represent the fold change from control mRNA expression levels, where a, b, d, g, h; P<0.05, aa, bb, cc, dd, ee, ff, gg, hh; P<0.005, eee, ggg, iii; P<0.0001.

Furthermore, FIG. 7 shows mRNA analyses of PPARγ/δ targets. Rosiglitazone, GW0742, compound 3-121 and compound 9 (10 μM dose for all compounds), were applied to 3T3-L1 adipocytes to determine effects on PPARγ/δ target mRNA expression levels. Compound 9 increased the gene expression of PPARγ targets MCAD, HSL, ATGL and adiponectin. Compound 9 marginally induced the expression of genes associated with lipid accumulation and synthesis such as FATP, CD36 and DGAT (see FIG. 7). Furthermore compound 9 also increased the gene expression of the PPAR δ target PDK4 in adipocytes.

EXAMPLE 6

Effects of Novel Compounds on Mitochondrial Biogenesis

PPARδ agonists have been shown to induce mitochondrial biogenesis. Therefore, to test the effects of the novel compounds on mitochondrial biogenesis, $C_2C_{12}$ skeletal muscle cells were cultured and treated with the novel compounds for 4 days. Changes associated with markers for mitochondrial biogenesis were determined by quantitative real time PCR.

Figure 8:
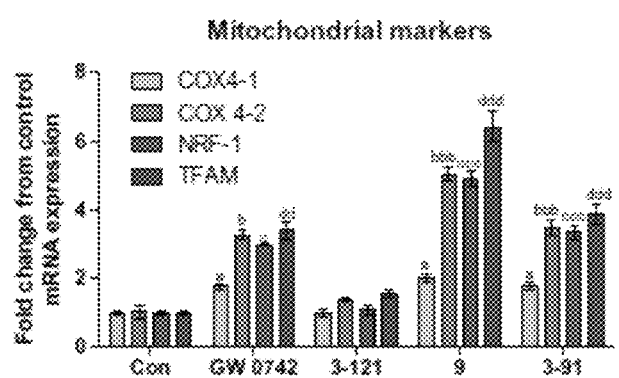
FIG. 8 shows gene expression of various mitochondrial markers in $C_2C_{12}$ skeletal muscle cells as demonstrated by quantitative RT-PCR. Data are means±SEM from 3 independent experiments. Values were set fold change from control. *P<0.05, "P<0.005, ***P<0.0001.

An increased gene expression of various mitochondrial markers is shown in FIG. 8. Compound 9 and GW0742 increases the gene expression of mitochondrial markers in $C_2C_{12}$ skeletal muscle cells as demonstrated by quantitative RT-PCR. Data are means±SEM from 3 independent experiments. Interestingly, compound 9 significantly increased cytochrome oxidase c 4-2 subunit, which is involved in inducing mitochondrial respiration and biogenesis in response to ischemia in the heart. This suggests a possible mechanism by which compound 9 can offer cardiovascular protection against ischemic injury.

EXAMPLE 7

Biodistribution Studies of Novel Compound 9

The biodistribution of the novel compounds of the present disclosure can be evaluated and compared to known TZDs, for example rosiglitazone. In the instant example, compound 9 was used as the exemplary novel compound. Compound 9 was administered orally for 1 day to see how much would collect into the brain and other tissues after 4 hours. This time point was selected because it is the half-life of rosiglitazone. Compound 9 was administered at a dose of 1 mg/kg of mouse given orally in saline. Rosiglitazone was administered at 10 mg/kg oral dose. After 4 hours, mice were euthanized and blood was drawn. Tissues were harvested and snap frozen in liquid nitrogen. Tissues were then ground up into powder form and de-suspended in DMSO and compared to pure drug by LC-Mass Spectral analysis. All samples and metabolic products were determined for stability, bioavailability and life span of drug in the system.

As shown in Table 2, the biodistribution properties of compound 9 is very different than rosiglitazone. In particular, compound 9 was detected in the brain of mice, evidencing that the drug crosses the blood brain barrier. In contrast, rosiglitazone was not detected in the brain of mice.

TABLE 2

Biodistribution of Compound 9 compared with Rosiglitazone

| Drug | Tissue | Concentration (ng/ml) | Tissue Concentration (ng/ml) | Tissue Distribution (ng/ml) |
|---|---|---|---|---|
| Compound 9 (3 mg/kg) | Blood | 144.08 | | |
| | Brain | 38.66 | 17.22 | 2.96 |
| | Adipose | 40.44 | 15.17 | 3.47 |
| | Heart | 22.09 | 3.19 | 1.35 |
| | Liver | 199.59 | 24.83 | 11.88 |
| Rosiglitazone (3 mg/kg) | Blood | 246.92 | | |
| | Brain | Not Detected | Not Detected | Not Detected |
| | Adipose | 13.01 | 5.00 | 2.24 |
| | Heart | 12.85 | 2.12 | 0.64 |
| | Liver | 250.32 | 8.89 | 4.95 |

EXAMPLE 8

Effects of Novel Compounds on Increase in Heart Size

The increase in heart size following administration of the novel compounds of the present disclosure compared to known TZDs, for example rosiglitazone, can be evaluated. In the instant example, compound 9 was used as the exemplary novel compound.

Figure 9:
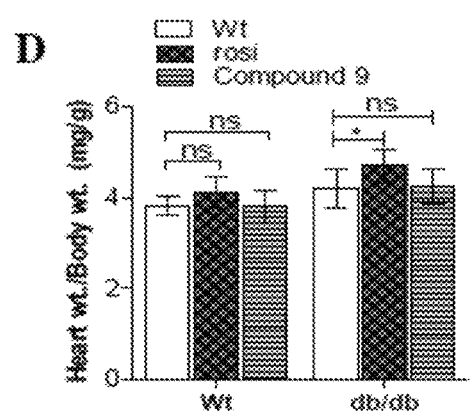
FIG. 9 shows that compound 9 (10 mg/kg) lacks increase in heart size as found in rosiglitazone treated mice (10 mg/kg). N=5 mice *; P<0.05.

In the instant example, compound 9 was used as the exemplary novel compound. Diabetic db/db mice were fed a normal rodent chow diet. Mice were given either oral concentrations of rosiglitazone (10 mg/kg) or compound 9 (10 mg/kg) daily for a duration of 1 month. Mice were then weighed and their hearts were extracted and weighed. The heart weight of the mice compared to the body weight of the mice was then calculated based upon heart weight to body weight ratio. Compared to rosiglitazone, administration of compound 9 resulted in decreased heart size in both wild type and db/db mice (see FIG. 9).

EXAMPLE 9

Effects of Novel Compounds on Blood Brain Barrier (BBB) Permeability

The predicted blood brain barrier (BBB) permeability of the novel compounds of the present disclosure compared to known TZDs, for example rosiglitazone, can be evaluated. In the instant example, compound 9 was used as the exemplary novel compound.

QikProp software provides fast predictions (10,000 molecules/hour) for seventeen physically significant descriptors and seven pharmaceutically relevant properties that are useful in predicting ADME (adsorption, distribution, metabolism, and excretion) characteristics of drug compounds. QikProp is the only currently available property prediction program that determines Caco-2 permeability and blood-brain barrier permeability of drug compounds. Data are evaluated based upon factors such as computed dipole moment of the molecule, molecular weight, hydrophobic components, C bonding with hydrogen, and the like.

Addition of unbranched chains to compound 9 enhances the lipophilicity of the molecule, resulting in enhanced lipophilicity to further facilitate the BBB permeability based upon calculations using QikProp software (see Table 3).

TABLE 3

Comparison of TZDs for BBB Permeability

| Drug | Molecular Weight | Log (p) partition coefficient | CNS Activity |
| --- | --- | --- | --- |
| Rosiglitazone | 357.4 | 2.45 | −1.0 |
| Pioglitazone | 356.4 | 2.3 | −2.0 |
| Compound 9 | 538 | 4.18 | 1.0 |

EXAMPLE 10

Effects of Novel Compounds on Cognition in Db/Db Mice

Groups of mice can be subjected to Y-maze tests and object recognition tests (ORT) to determine the improvement of working and declarative memory. Briefly the Y-maze test involves the novel arm being blocked, so mice are allowed to explore the other two arms for 15 minutes. Appropriate external and internal cues are assigned for each arm. After 15 minute training sessions, the mice are caged in the same room for 4 hours (holding session) followed by the novel arm exploration where mice are allowed to explore the novel arm for 4 hours.

Figure 10:
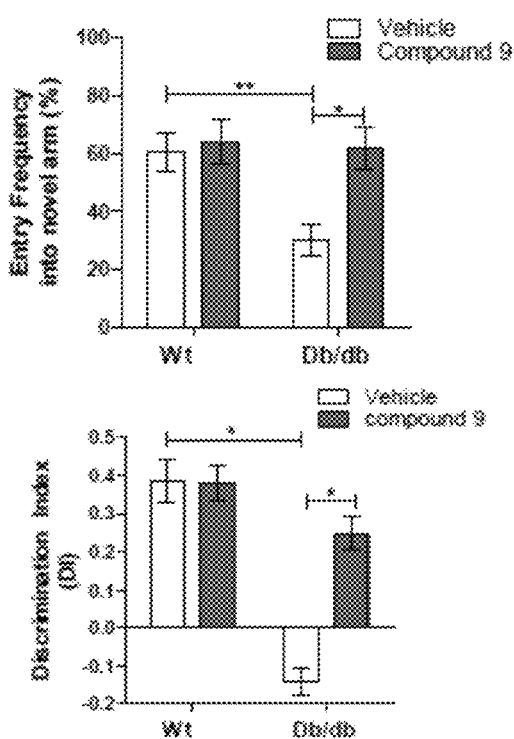
FIG. 10 shows that compound 9 (1 mg/kg) improves cognition in db/db mice as determined by Y maze behavioral tests. N=4 mice, DI (preliminary data) was determined after 1 hour of exploration. *; P<0.4, **; P<0.005.

In the instant example, compound 9 was used as the exemplary novel compound. As shown in FIG. 10, oral administration of compound 9 in db/db mice improves cognition as determined by Y maze behavioral tests.

EXAMPLE 11

Intracerebroventricular (ICV) Delivery of Rosiglitazone Improves Memory in Mice

Impaired hippocampal long term potentiation (LTP) has been shown in the CA1 and the CA3 subfield of type 2 diabetic mice hippocampus. These findings have been explained at the molecular level, where alterations in post synaptic receptor expression including glutamatergic AMPAR subtypes lead to impairments in synaptic plasticity. Furthermore, the degree of LTP deficit was directly related to the duration of diabetes and the severity of hyperglycemia.

Recent studies demonstrate that improvement in insulin sensitivity in the brain may ameliorate memory deficits by improving synaptic plasticity. PPARγ agonists such as rosiglitazone (rosi) and pioglitazone are insulin sensitizing agents that improve neuronal insulin receptor function in the hippocampus in high fat diet induced diabetic rats. In regard to how the activation of PPARγ improves cognition in AD, it has been determined that rosiglitazone enhances learning and synaptic plasticity in the dentate gyrus in middle aged rats with chronic rosiglitazone treatment by reversing basal plasma insulin abnormalities and increased hippocampal glucose transporter (GLUT)-3 expressions. PPARγ agonists have also been found to attenuate Aβ plaque mediated impairment of hippocampal post tetanic potentiation (PTP) and LTP and thus offer an alternative mechanism by which these insulin sensitizing agents improve synaptic plasticity. Moreover, rosiglitazone in Alzheimer's transgenic mice was found to mitigate amyloid and tau pathologies. These studies verify that global PPARγ activation has an effect upon mitigating impaired memory and synaptic plasticity in models of diabetes and AD. However, the molecular mechanisms of how central PPARγ improves synaptic plasticity in rodent models are not fully elucidated. To highlight the significance of PPARγ towards impaired cognition, Pro12Ala polymorphism in the human PPARγ gene was found to induce cognitive impairment.

Male C57/b16 and leptin deficient (db/db) mice were purchased from Jackson Laboratories (Bar Harbor, Me.). Animals were maintained in 12 hours of dark-light cycle. Oral/intracranial delivery of rosiglitazone was initiated at 4 months of age. Mice were randomly separated into several groups with 10 mice per group; db/db and C57b16 mice formed four independent groups that received rosiglitazone either orally (3 mg/kg) or intracerebroventricular (ICV) (0.3 mg/kg by Alzet mini-osmotic pump). Both drugs were suspended in sterile saline. Four additional groups comprised the control portion of the study and received physiological saline in the place of the drug treatment either orally or by ICV. Intracranial targeted delivery of rosiglitazone or saline into ventricles was accomplished by fixing the anesthetized mouse in a stereotaxic frame and using the coordinates established in the mouse brain with the aid of a stereotaxic coordinates map. All treatments extended for 2 weeks.

Y-Maze:

After 2 weeks of rosiglitazone treatment, behavioral studies were performed in all animal groups following acclimation of mice in the experimental environment for 24 hours. The training session for the Y-maze involved the blockage of the novel arm allowing the mice to explore the other two arms for 15 minutes. Appropriate external and internal cues were assigned to each arm. After the training session, mice were housed in the experimental environment in the same room for 5 minutes, 2, 4 and 24 hours. Mice were then introduced into the Y-maze where the novel arm was opened and was allowed to explore for 5 minutes. The percentage entry into the novel vs previously explored arms (% novel arm entry), and spontaneous alternation scores for each mouse were calculated as a measure of short-term working memory and spatial navigation. All animal activities were recorded by Logitech video camera. An animal was considered to enter an arm whenever he had all four paws inside that arm. Five trials were performed after a 24 hour interval for each training session. Results were analyzed by Prism software and the significance of the results was analyzed by using a two-tailed Student's t-test.

Object Recognition Task (ORT):

Mice were divided into four experimental groups as discussed above. Object recognition tasks (ORT) were performed as described elsewhere (Escribano et al., 2010). ORT was performed in a squared arena (30 cm×30 cm×25 cm) with clear plexiglass walls and a black painted plastic-covered floor. Approximately 1 hour prior to testing, mice were allowed to explore the apparatus without objects for 5 minutes. After habituation, two sessions of familiarization were administered (T1 and T2, 10 minutes apart), in which the animals were left to explore for 10 minutes two identical objects (black cylinder blocks) that were placed in opposite sides of the apparatus 10 cm from the sidewall. The trial of choice (T3), tested memory retention and was given 5 minutes, 1, 4 and 24 hours after T2. In this session, two objects were presented, one of the blocks was used in the familiarization session (T1 and T2) and other was different in shape and color; therefore the mice were re-exposed to a similar and a new object. Exploration was defined as directing the nose to an object at a distance 2 cm and/or touching the object with the nose. To avoid the presence of olfactory trails, the apparatus and the objects were thoroughly cleaned with ethanol after each trial. The time spent by the animals in exploring each object was recorded digitally and number of associations and times were analyzed by a naive subject. The reaction to the new object or novel arm (Y-Maze) during T3 was measured by calculating the discrimination index (DI): an index of cognitive assessment, was calculated as the difference between the time spent exploring the novel object or arm (N) and the familiar one (F) in relation to the total time spent exploring the objects [(N−F)/(N+F)]. Thus, a ratio of less than 0.5 reflects equal exploration of the familiar and the new object, indicating no learning retention.

Figure 11A:
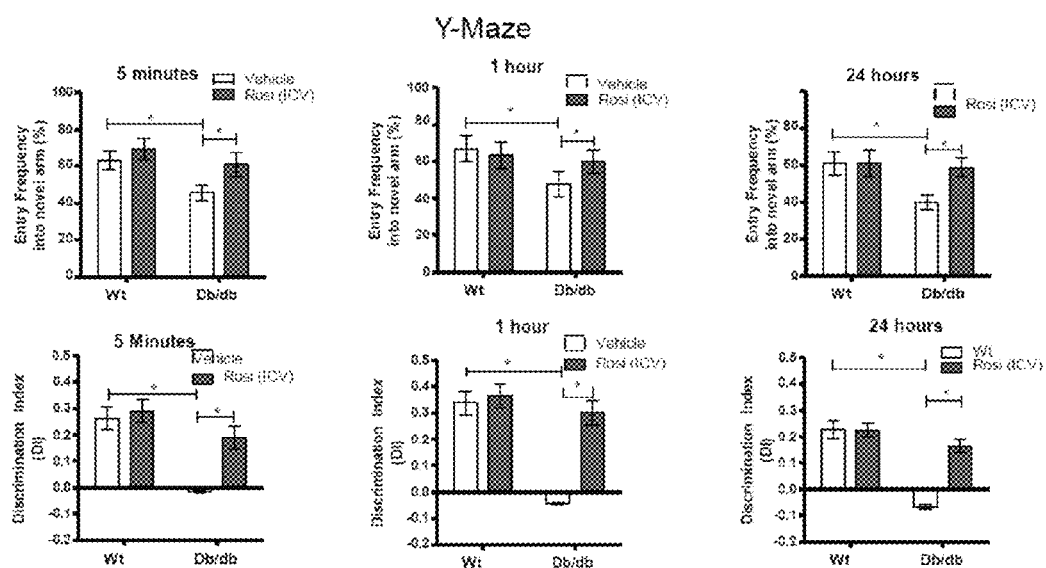
FIG. 11 shows that PPARγ activation improves short-term and long-term spatial memory in the diabetic mouse. (A) Results from frequency of entry into novel or familiar other arm (5 minutes, 1 hour and 24 hours) as demonstrated percent entry. (B) Results for object recognition tests reflect time spent by the animals in exploring each object and number of associations and times were analyzed by a naive subject. The reaction to the new object or novel arm (Y-Maze) during T3 was measured by calculating the discrimination index (DI) which describes the difference between the times spent exploring the novel arm (A) or object (B) and the familiar one. Rosiglitazone delivered intracranially into db/db mice, improved the impaired preference and entry for the novel arm in the all training intervals. Where n=10 mice per group of treatment and *; p<0.05. Furthermore, PPARγ activation in the diabetic hippocampus improves basal synaptic transmission and long term potentiation. (C) Extra cellular field recordings of excitatory post synaptic potential (EPSP) amplitude and slope were recorded. (D) Long term potentiation (LTP) was significantly improved in rosiglitazone treated diabetic (db/db) mice in comparison to control diabetic mice by high frequency stimulation (3×100 Hz trains with a 20 second intertrain interval). Quantification of post-tetanic potentiation (PTP), a form of short lived synaptic plasticity which results in increased currents (mEPSCs). Where n=10 mice per group of treatment and *; P<0.05, ; P<0.005, *; P<0.0001.
Figure 11B:
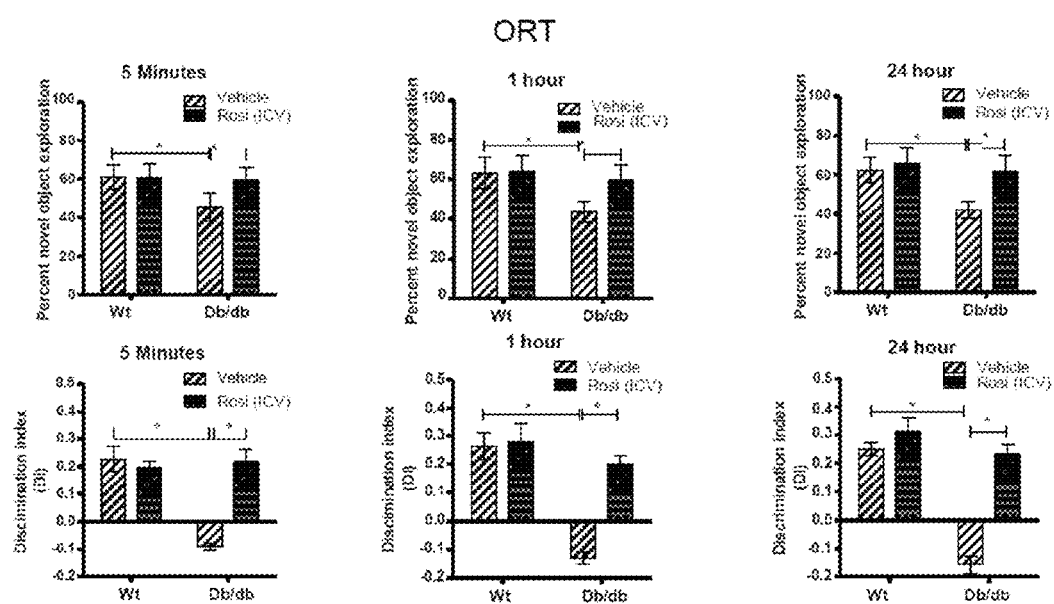

The results of the Y-Maze experiments are shown in FIG. 11A and the results of the ORT are shown in FIG. 11B. Significant deficits in spatial memory were observed in db/db mice when compared to c57/b16 mice in the entry frequency (%) in novel arm, and time spent in the novel arm in Y maze (see FIG. 11A). Student t-test was used to analyze the significance between the groups for the Y-maze and ORT to determine the level of exploration as measured by novel arm or novel object discrimination index (DI). The DI was significantly impaired in db/db mice (FIG. 11B; p<0.05). There were no significant differences in Y-maze or ORT after 24 hour outcomes in in mice treated orally with rosiglitazone.

After two weeks of rosiglitazone treatment, mice were decapitated under anesthesia. Brains were processed and coronal hippocampal slices (350-400 µm) were obtained using a Vibratome and were incubated in artificial cerebrospinal fluid (aCSF) for an hour at 30° C. Electrophysiological recordings were accomplished according to known methods. Briefly, field excitatory postsynaptic potentials (fEPSPs) were recorded from the CA1 stratum radiatum with a glass electrode (1-4 mΩ) filled with aCSF, and test pulses (0.033 Hz) were delivered through a platinum bipolar electrode placed in the Schaffer-collateral commissural pathway between CA3 and CA1 regions. Input-output curves were recorded by varying stimulus intensity between 0 µA to 300 µA in steps of 50 µA and measuring the slope of the fEPSPs as well as the amplitude of fiber volley. Paired-pulse facilitation (PPF) was evaluated by stimulating with twin pulses at the inter pulse intervals of 40, 60, 80, 150, and 200 milliseconds. For LTP and PPF experiments, the fEPSPs, were recorded at 40% of maximal response. Following stable baseline recordings of at least 30 minutes, a high frequency stimulus was applied using the test pulse stimulus intensity. The high frequency stimuli protocol for inducing LTP consisted of 3 trains of 100 pulses (100 Hz), with an inter-train interval of 20 seconds. LTP was measured as the percentage of the baseline fEPSP slope. During the 30 minute baseline and 1 hour following the tetanus, fEPSP peak amplitude and slope were analyzed online using WinLTP acquisition software. The data are presented as mean+/−SEM. Results were analyzed by Prizm software and the significance of the results was analyzed by using a two-tailed Student's t-test.

Figure 11C:
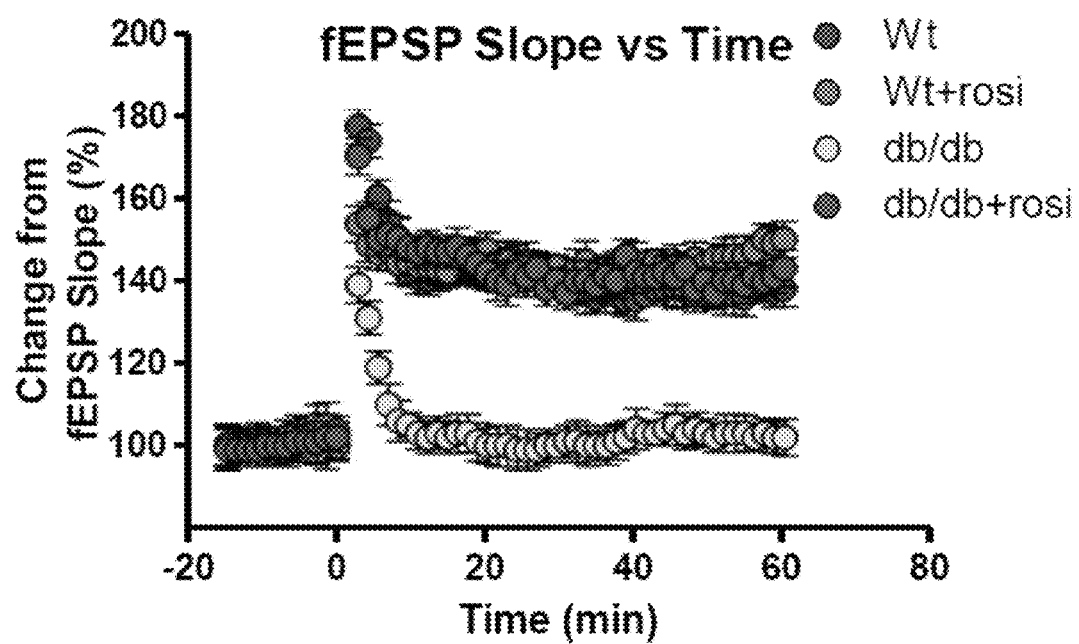
Figure 11D:
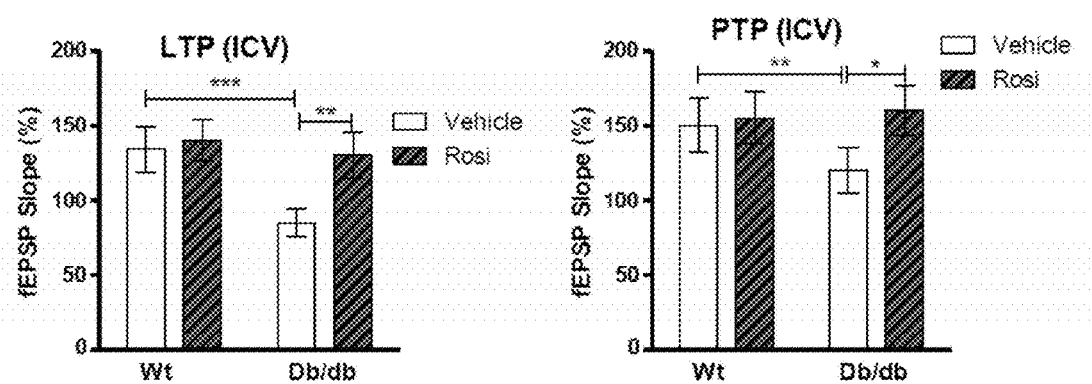

To further consolidate the improvement of memory by central activation of PPARγ, changes in synaptic plasticity were analyzed using the magnitude of long term potentiation (LTP) and post-tetanic stimulation (PTP) in ICV as well as oral rosiglitazone treated db/db and wild type mice. Interestingly, LTP was significantly reduced in db/db mice (approximately 50%) when compared to the wild type mice. This effect was ameliorated by ICV (>50%) and rosiglitazone treatment (see FIG. 11D). More specifically, a change of 148.33±2.5 percent in the slope of fEPSP was observed after sixty minutes of induction of LTP in db/db mice treated with rosi (ICV). However an inconsequential improvement was observed (126±5.3) in the fEPSP slope (LTP studies) in db/db mice treated with oral rosiglitazone when compared to untreated db/db mice. In contrast, db/db mice receiving rosi by ICV had significantly improved fEPSP slope, similar to the slope observed in wild type mice (see FIG. 11C). PTP, which measures short-term plasticity was detrimentally affected in db/db mice and was improved with both oral and ICV rosiglitazone treatment (see FIG. 11D).

EXAMPLE 12

Effects of Novel Compounds on PPARγ Targets in the Hippocampus

The selective activation of PPARγ targets in hippocampi of the novel compounds of the present disclosure compared to known TZDs, for example rosiglitazone, can be evaluated. In the instant example, compound 9 was used as the exemplary novel compound.

Male C57/b16 and leptin deficient (db/db) mice were purchased from Jackson Laboratories (Bar Harbor, Me.). Animals were maintained in 12 hours of dark-light cycle. Oral/intracranial delivery of rosiglitazone was initiated at 4 months of age. Mice were randomly separated into several groups with 10 mice per group; db/db and C57b16 mice formed four independent groups that received rosiglitazone either orally (3 mg/kg) or intracerebroventricular (ICV) (0.3 mg/kg by Alzet mini-osmotic pump). Both drugs were suspended in sterile saline. Four additional groups comprised the control portion of the study and received physiological saline in the place of the drug treatment either orally or by ICV. Intracranial targeted delivery of rosiglitazone or saline into ventricles was accomplished by fixing the anesthetized mouse in a stereotaxic frame and using the coordinates established in the mouse brain with the aid of a stereotaxic coordinates map. All treatments extended for 2 weeks.

Total RNA was isolated from hippocampi using RNAeasy Lipid Tissue Mini Kit (Qiagen, Valencia, Calif.) and was converted to cDNA (iScript cDNA synthesis kit—Bio Rad, Hercules, Calif.). Real-time PCR was performed in triplicate using a RT2 SYBR Green/Fluorescein fast master mix (SA-Bioscience) and an iCycler real-time PCR thermocycler (Bio-Rad). Gene expression was normalized to β-actin. Relative gene expression was determined by the comparative CT method (30). The data is presented as mean+/−SEM.

Figure 12:
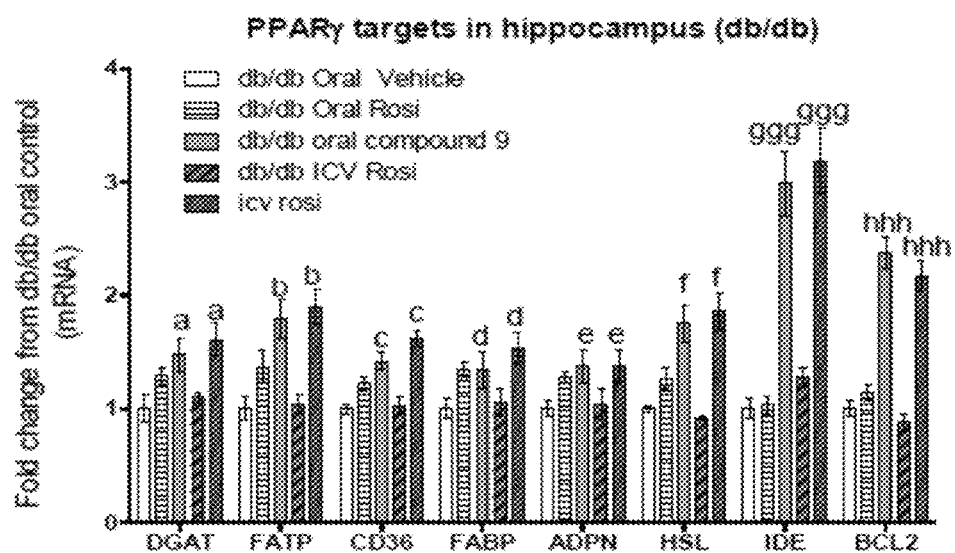
FIG. 12 shows that compound 9 (1 mg/kg) orally mediates selective activation of PPARγ targets in comparison to rosiglitazone (ICV) in hippocampi. Changes in gene (mRNA) expression are in comparison to control. Rosiglitazone (0.1 mg/kg ICV). a, g, h, i; P<0.05, aa, bb, cc, dd, ff, gg, hh; P<0.005, eee, hhh; P<0.0001 as measured by qRT-PCR analysis.

As shown in FIG. 12, compound 9 (1 mg/kg) orally mediates selective activation of PPARγ targets in hippocampi compared to rosiglitazone (delivered ICV) and control as measured by changes in gene (mRNA) expression.

EXAMPLE 13

Effects of Novel Compounds on Synaptic Plasticity in Alzheimer's Disease

Mouse models for AD (034830-JAX) can be purchased from the Jackson Laboratories. Mice homozygous for all three mutant alleles (3xTg-AD; homozygous for the Psen1 mutation, APPSwe and tauP301L transgenes (Tg(APPSwe, tauP301L)1Lfa)) are viable and fertile. Translation of the overexpressed transgenes is restricted to the hippocampus and cerebral cortex. Amyloid beta peptide deposition with plaque and tangle pathology associated with synaptic dysfunction is observed as early as 3-4 months. Synaptic transmission and LTP are impaired in mice at 5-6 months of age, which can be the age evaluated in the instant example. Breeding colonies have been established at the Auburn Animal Facilitates (Veterinary Medical Center, AAALAC accredited) with full time staff to help in regulating mice population. Male mice can begin drug therapy at 6 months of age and given the drugs for 4 weeks daily by oral gavage.

i. 3xTg-AD-Transgenic Male Mice (6 Mice Per Group); 1 Daily Dose of Compound 9; 1 mg/kg (4 Weeks Dosing).

The bioavailability in the brain for required dose is determined from pharmacokinetic (PK) parameters (AUC, T(max) and C(max)) and compared across liquid blood, plasma matrices, cerebrospinal fluid and hippocampal lysate by LC Mass Spec analysis. Compound 9 dosing values were analyzed by behavior and gene expression data in mice to achieve a dose of 0.1 mg/kg in the brain based upon preliminary data rosiglitazone concentrations which improved behavior and LTP in db/db mice delivered ICV by mini-osmotic pumps for 2 weeks. Cell viability assays (MTT and Annexin V—propidium iodide) for LD50 and EC50 concentrations upon neurons and concentrations to attain gene expression levels similar to rosiglitazone were established.

ii. 3xTg-AD-Transgenic Male Mice with Rosiglitazone. (6 Male Mice).

A dose of 10 mg/kg for compound 9 was determined to accumulate in the brain after 3 weeks. Thus, a 10 mg/kg dose for 4 weeks can be administered.

iii. 3xTg-AD-Transgenic Male Mice (6 Mice Per Group): Sham Mice can be Given Oral Gavage of Saline Daily.

Control mice can be given an oral gavage of saline daily.

iv. Three Groups of 6 Wild Type (C57b16J) Male Mice can be Given Either Compound 9 (1 mg/kg) or Rosiglitazone (10 mg/kg) for 4 Weeks and a Control Group.

At the end of the study, heart weight and cardiac function can be measured by echo-cardiography, available as part of a core-facility at Veterinary Medical Hospital to researchers at Auburn University. This can allow evaluation of mice for cardiotoxicity associated with rosiglitazone.

Experimental Approaches & Methods—Electrophysiology & Synaptic Plasticity:

Hippocampal long term potentiation (LTP) electrophysiological studies can be carried out on treated mice. First, basal excitatory synaptic transmission before LTP can be evaluated (Theta Burst Stimulations (TBS)). The contributions of AMPAR and NMDAR postsynaptic basal transmission can be determined from electrophysiological measurements of both spontaneous and evoked excitatory post synaptic currents (EPSCs).

First, the frequency and amplitude of AMPA receptor mediated spontaneous miniature EPSCs can be measured in the presence of tetrodotoxin. This may reveal whether drug treatment can alter the overall levels of excitatory synaptic input. The AMPA and NMDA receptor components can be analyzed at negative (−80) and positive (+40) membrane potentials, respectively and can be confirmed with utilization of pharmacological inhibitors CNQX (AMPAR antagonist) and AP5 (NMDAR antagonist). Patch clamp electrophysiological (field) recordings to assess the amplitude and maintenance of LTP, plus pharmacological blockers can be used to confirm the role of the NMDA receptor in LTP induction. Confirmation of the contributions of NMDA and AMPA receptors to long term changes in synaptic strength can be determined.

EXAMPLE 14

Effects of Novel Compounds on Improvement in Cognition

Mice can be acclimated to the experimental environment for 24 hrs. Groups of mice can be subjected to Y-maze tests and object recognition tests (ORT) to determine the improvement of working and declarative memory. Briefly the Y-maze test involves the novel arm being blocked, so mice are allowed to explore the other two arms for 15 minutes. Appropriate external and internal cues are assigned for each arm. After 15 minute training sessions, the mice are caged in the same room for 4 hours (holding session) followed by the novel arm exploration where mice are allowed to explore the novel arm for 5 minutes, 1 hour, 4 hours, 8 hours, and 24 hours. Novel arm entry frequency and resting times plus discrimination indices can be determined and all animal activities can be recorded by Logitech video camera and software. The same form of study can be accomplished in object recognition (ORT) study in a clear plexiglass square: 30 centimeters tall each side wall. Significance of data can be analyzed by two-tailed Student's t-test. Oral administration of compound 9 has been shown to improve cognition in db/db mice, 1 hour after the holding session. This time point is significant for LTP and thus synaptic consolidation and memory formation.

EXAMPLE 15

Effects of Novel Compounds on Insulin Signaling (IRS-1)

There exists a significant gap in knowledge as to how central PPARγ improves insulin signaling in the hippocampus. In the instant example, compound 9 was used as the exemplary novel compound. The utilization of compound 9 can focus upon the effects of improving central insulin signaling cascade upon cognition. More specifically, the mechanism by which central mediators in the insulin signaling cascade improve dendritic microtubule stability can be determined.

Tau hyperphosphorylation represents a classic hallmark for the evidence of AD due to the involvement of Tau in microtubule disassembly and neuronal degeneration. The mechanism underlying the Aβ-induced Tau hyperphosphorylation as mediated by impaired insulin signal transduction has been delineated, finding that pAKT and GSKβ upon insulin stimulation was compromised under Aβ conditions. Furthermore, in post mortem Alzheimer's brain, reduced mediators have been found in the insulin signaling cascade including the insulin receptor, insulin receptor substrate (IRS-1), and the pro-survival protein AKT.

The application of rosiglitazone, an insulin sensitizing agent, has been shown to mitigate Tau hyperphosphorylation, and suggests that improving the insulin signaling cascade dysregulation in AD may offer potential for a therapeutic approach for AD. However, there is a lack in knowledge for specific molecular targets in the insulin signaling cascade that are regulated by PPARγ to improve memory in AD.

Figure 13:
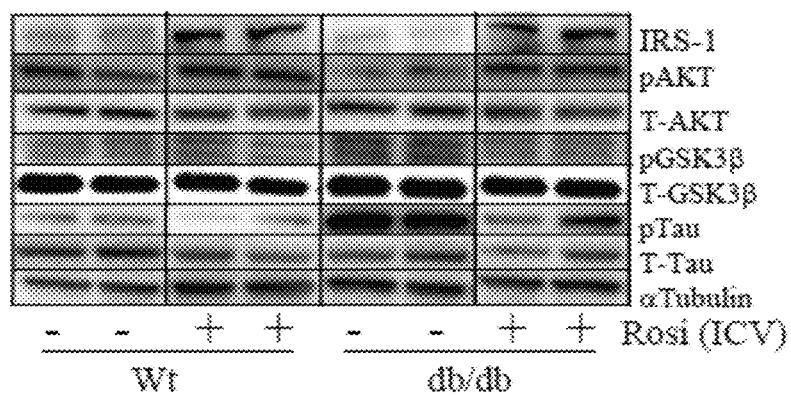
FIG. 13 shows that rosiglitazone (ICV) improves IRS-1 expression, the insulin signaling cascade, and decreases Tau phosphorylation in wild type and db/db hippocampi.

As shown in FIG. 13, administration of rosiglitazone (0.1 mg/kg ICV) daily for 14 days increases IRS-1 protein expression in db/db mice. Thus, it is hypothesized that elevated PTEN levels in AD increase Tau hyperphosphorylation and PPARγ activation ameliorates this by increasing IRS2. This hypothesis can identify a new molecular target for therapeutic potential.

Previous findings in skeletal muscle confirm that PPARγ increases insulin signaling via IRS-1 signaling and thus offers a mechanism as to how PPARγ agonism improves insulin sensitivity in skeletal muscle. It can be explored how central PPARγ improves the insulin signaling cascade by involving IRS-1 which mitigates the development of Tau hyperphosphorylation (see FIG. 13). Compound 9 and rosiglitazone given orally can be evaluated for their improvement in IRS1 expression and the subsequent insulin signaling mediators (PI3K-AKT) in an AD model. Furthermore, the significance of PPARγ mediated IRS-1 expression against Ap mediated Tau hyperphosphorylation cab be explored in primary neuronal cells by mitigating the tumor suppressor phosphatase and tensin homologue deleted on chromosome 10 (PTEN). This protein is known to suppress activation of the pro-survival protein AKT.

EXAMPLE 16

Effects of Novel Compounds on Tau Hyperphosphorylation

3xTG-AD mice and primary hippocampal neuronal cells can be utilized to determine whether the PPARγ mediated increase in IRS-1 attenuates Aβ mediated Tau hyperphosphorylation.

Tissue acquired from previously describe experiments can be utilized in this example and compared to primary cell culture studies for the effects of PPARγ activation upon Tau hyperphosphorylation as determined by western analysis.

Primary hippocampal cells: Rat primary neuron cultures for luciferase assays as well as westerns and all other cell cultured assays are described herein. Rat primary neuron cultures can be generated from embryonic day 18-21 rat embryo (male and female) brains (Sprague Dawley) following known protocols. Briefly, the cortices, together with hippocampi, can be dissected and cells can be dissociated with 0.25% trypsin (Invitrogen), treated with 0.05% DNase I (Roche). To remove alternative cells and RBC's, tissue slurry can be allowed to sediment by gravity for 30 minutes at room temperature. Lower cellular suspension can then be plated on poly-D-lysine-coated dishes in Neurobasal A medium (Invitrogen) with B27 supplement (Invitrogen), penicillin (PAA Laboratories, 100 U/ml), streptomycin (PAA Laboratories, 0.1 mg/ml), and 1 mM L-glutamine (PAA Laboratories). Mitotic inhibitor 5-fluoro-2'-deoxyuridine (Sigma) can be added to the medium (10 μM) at 2 days in vitro (DIV) to remove fibroblast and astrocyte contamination. To test isolation purity for neurons, markers for neurons (MAP2) specificity can be measured by gene and western analysis.

Handling of p-amyloid peptide: pAP1-42, pAP1-40, and pAP25-35 can be purchased from ANASPEC (Freemont, Calif.). Aβ can be dissolved in sterile, doubly distilled water at a concentration of 2.5 mM and stored at −20° C. Before the experiments, pAP1-42 and pAP1-40 stock solutions can be kept for 1 week in a 37° C. incubator so as to allow aggregation. Primary neuronal cells can be grown to 90 percent confluence and then transfected for IRS-1 RNAi (cat #SR506443, ORIGENE, Rockland, Mass.) to down regulate IRS-1 expression. Cells can then be treated for 24 hours with compound 9 (1 μM) or rosiglitazone (10 μM). These doses are compatible for inducing many PPARγ regulatable genes in cell culture. The different forms of Aβ can then be applied to the neuronal cells for 12 and 24 additional hours (1-20 μM).

Western analysis for Insulin signaling mediators and Tau hyperphosphorylation (pS396/404 Tau) (Cell Signaling) can be resolved by western analysis.

PPARγ activation may significantly impair Aβ mediated Tau hyperphosphorylation and IRS-1 may be implicitly involved in the signaling pathway. In the event that cell viability is detrimentally affected by Aβ application, less exposure time and reduced concentrations can be utilized. Alternatively, hippocampal neuronal cell lines can be utilized; H19-7 cells can be grown and induced for differentiation. H19-7 hippocampal cell are chosen because they develop post synaptic receptor expression.

As a positive control and to define the significance of IRS-1 towards protecting the neurons from Aβ mediated Tau hyperphosphorylation, the IRS-1 plasmid can be transfected into another set of primary cells, thus allowing overexpression of IRS-1 and application of Aβ as indicated above. Tau phosphorylation (pS396/404 Tau) can then be measured by western analysis.

EXAMPLE 17

Central PPARγ Activation Attenuates PTEN Expression

Neurofibrillary tangles (NFTs), containing abnormally hyperphosphorylated tau, are implicated in the pathogenesis of several neurodegenerative diseases including Alzheimer's disease (AD). The molecular mechanisms underlying the regulation of tau phosphorylation are largely unknown. While the PI3K/Akt pathway, which is central in the insulin signaling pathway, has been shown to regulate multiple cellular events pertinent to AD pathogenesis, the potential functions of tumor suppressor phosphatase and tensin homologue deleted on chromosome 10 (PTEN) in AD pathogenesis has been minimally explored.

Figure 14:
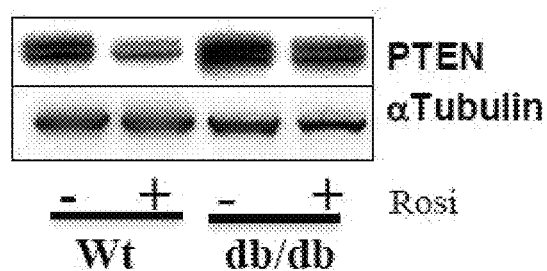
FIG. 14 shows that rosiglitazone (0.1 mg/kg) (ICV) mitigates PTEN expression in wild type and db/db mice.

It has recently been found that Aβ results in over-expression of PTEN resulting in a negative regulation of PIP320. Further, the overexpression of wild-type (WT) PTEN has been found to alter tau phosphorylation at several sites, increase tau-microtubule association and decreases formation of tau aggregates. These findings suggest a link between malfunction of PTEN and tauopathy, and imply PTEN as a therapeutic target for tauopathy. It has been determined that rosiglitazone (0.1 mg/kg ICV) mitigates the increased expression of PTEN in the hippocampus of severely diabetic db/db mice (see FIG. 14). Accordingly, the effects of PPARγ upon Aβ-PTEN mediated tau phosphorylation, the associated microtubule association and formation of aggregates, and consequentially neuronal morphology can be evaluated. More specifically PPARγ mediated increased IRS-1 expression may result in mitigating PTEN and improve PI3K and reduce Tau phosphorylation.

New molecular signaling targets for therapeutic potential for AD are disclosed due to a novel set of tools to better investigate how central PPARγ improves pathologies associated with AD. Thus, tissue samples from 3x-Tg-AD and wild type mice from prior experiments can be utilized and western analysis can be performed to determine whether central PPARγ activation (e.g., via compound 9) can reduce expression of PTEN and the downstream mediator Tau hyperphosphorylation in the AD hippocampus by western analysis.

In addition, the levels of PI3Kinase, pAKT/Total AKT ratio, pGSK3b/total GKS3b and pTau levels can be determined by western analysis. It can be investigated in primary neuronal cells whether increased IRS-1 expression results in mitigating PTEN and improves PI3K and diminished Tau phosphorylation. In this regard, IRS-1 expression can be attenuated and the levels of PTEN expression can be measured. IRS-1 (Addgene #11027) can be overexpressed in primary neuronal cells and apply Aβ as previously described PTEN, PI3K and pAKT expression levels can be measured by western analysis. All western studies, a-tubulin can be utilized as a standardizing marker.

PTEN may be centrally involved in the Aβ mediated development of Tau hyperphosphorylation. As a negative control, a PTEN inhibitor VO—OHpic trihydrate (Sigma-Aldiche) can be utilized to further implicate the involvement of PTEN in the signaling pathway towards the development of Aβ mediated Tauopathy. Finally, AD may alter the balance of PTEN-IRS-1 upon regulating the expression of PI3K towards preventing the activation of the pro-survival protein AKT resulting in Tau hyperphosphorylation.

EXAMPLE 18

Relation of BDNF to Improved Cognition

Neurotrophins are a family of proteins that are essential for differentiation and survival of the neural network by modulating the synaptic structure and function, including BDNF. Importantly, it has been discovered that telmisartan, a unique angiotensin receptor blocker that has partial PPARγ activity, induced an increase in BDNF in hypertensive rat. Localization of BDNF to glutamate synapses suggests that BDNF is a regulator of excitatory transmission and plasticity. BDNF activates distinct mechanisms to regulate the induction, early maintenance, and late maintenance phases of LTP. More specifically, BDNF triggers protein synthesis-dependent late phase LTP, a process referred to as synaptic consolidation, as well as through transcriptional regulation of AMPAR mRNA. Further, BDNF also regulates AMPAR trafficking to the postsynaptic sites and up-regulates surface AMPAR in cultured hippocampal and cortical neurons. BDNF has also been shown to increase dendritic spine formation and postsynaptic NMDA and GABA receptor expression and thus further validates it significance towards it role in regulating synaptic plasticity.

Figure 15A:
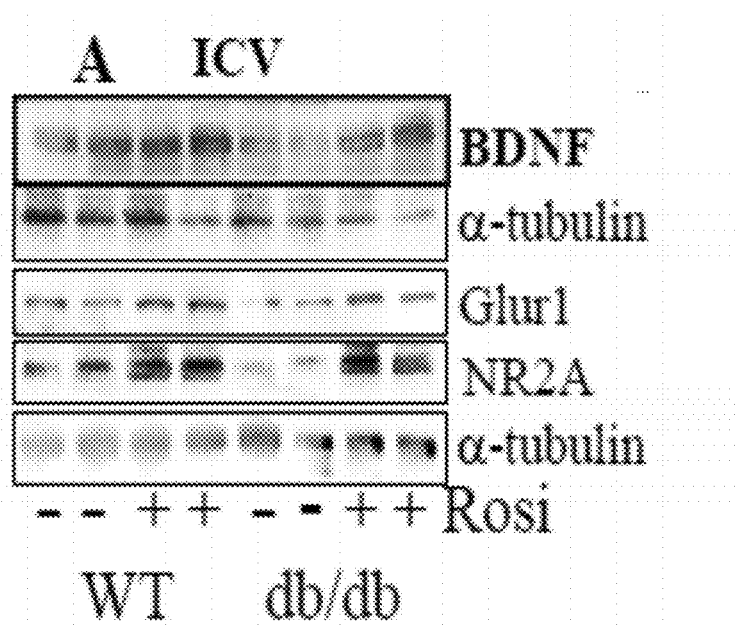
FIG. 15 shows that rosiglitazone and compound 9 increase BDNF and post synaptic markers. (A) Intracranial (IC) rosiglitazone (0.1 mg/kg) treatment induced an increase in BDNF protein and (B) mRNA (exon IX), as well as GluR1 and NR2A in db/db mice. (C) Rosiglitazone induces increased expression of BDNF, GluR1 and NR2A in hippocampal H19 cells. (D) Compound 9 increases BDNF expression in H19 cells. (E) Both constitutively active (CA)-PPARγ & compound 9 induce an increase in the post synaptic density marker PSD95 expression in H19-7 cells as demonstrated by western analysis. (F) Immunofluorescence localization validates rosiglitazone (10 μM) and compound 9 (1 μM) increases BDNF expression and PSD95 (green) (G) and spine density (red) in H-19 cells.

Interestingly, attenuated BDNF levels have been observed in hippocampi from AD patients, transgenic AD rodent models, and type 2 diabetic patients. It has been found that BDNF regulates glucose metabolism by modulating energy balance in diabetic mice brains. As shown in FIGS. 15A & B, reduced BDNF protein and gene expression is observed in db/db hippocampi which helps explain the observation that diabetes attenuates the expression of post synaptic receptor expression levels in db/db mice hippocampi. The delivery of rosiglitazone (ICV) improved BDNF and post synaptic receptors, NR2A, and GluR1 expression in the diabetic hippocampus (see FIG. 15A). These findings were replicated in H19-7 hippocampal neuronal cell culture model with rosiglitazone (10 μM) and by transient transfection (CA-PPARγ) which demonstrated increased mRNA and protein levels of BDNF, GluR1 and NR2A (see FIGS. 15B & C).

As mentioned above, BDNF is known to induce synaptogenesis, spine density, and post synaptic receptor expression in neurons but has been previously shown to be reduced in AD brains. The postsynaptic density-95 (PSD95) scaffolding protein has been identified as a marker for synaptic strength and spine density and therefore in hippocampal neurons, BDNF has been found to augment the levels of PSD-95 in spines. As shown in the imaging data of FIG. 15G, PPARγ activation induces increased PSD95 levels and spine formation in H19-7 hippocampal cells and aids in explaining the observation of increased synaptic plasticity in our rosiglitazone (ICV) treated db/db mice.

The novel compounds (e.g., compound 9) have been developed as tools to better study the effects of PPARγ activation in the hippocampus upon cognition in AD. As shown in FIG. 15D, compound 9 induces an increase in BDNF expression and also promotes spine formation in H19 cells (see FIGS. 15E and G).

EXAMPLE 19

Relation of PPARγ to BDNF and AMPAR

BDNF binds specifically to the tyrosine kinase receptor TrkB which then leads to auto-phosphorylation of tyrosine residues within the intracellular domains of the receptor. The ensuing signaling cascade leads to well established role of neurotrophin in neuronal differentiation, survival and growth of the neuron during development. To determine the significance of PPARγ mediated BDNF expression on behavior, the TrkB receptor antagonist ANA12 (R&D Systems, cat #04781), which prevents BDNF activity in a non-competitive (IC50=45.6 nM & 41.1 μM) manner, can be utilized. To suppress BDNF activity, ANA12 can be administered into the ICV region after the above rosiglitazone and compound 9 treatments once daily for 5 days. Briefly, mice can be anaesthetized with avertin (1.2%, 0.02 ml/g, i.p.) and chronically implanted with double guide cannulas (Plastics One, Roanoke, Va., USA) in the CA1 region of the dorsal hippocampus using a high precision stereotaxic system, and fixed to the skull using dental cement. Coordinates can be based on the stereotaxic plates of the mouse brain atlas. Anterior posterior coordinates relative to the bregma were 1.6 mm, and lateral coordinates relative to the mid sagittal suture line were ±1.03 mm.

Behavioral: (Y-maze and object recognition) and electrophysiological studies as discussed previously can then be carried out to validate the significance of PPARγ-BDNF signaling on memory and long term potentiation by comparisons of rosiglitazone and compound 9 treated Tg2576AD mice with or without ANA12 compound (sham treated mice). Changes in downstream effectors of DBNF-TrkB activation can be measured by western analysis (pERK/T-ERK) to determine the relative attenuation of BDNF expression in the hippocampus. Gene (qRT-PCR) and western analysis studies can help measure changes in post-synaptic receptor and arboritization in the CA1-CA3 regions of the hippocampi.

PPARγ increases BDNF and AMPAR expression as well as improved synaptic plasticity. Thus, it is hypothesized that the increased BDNF expression mediated by PPARγ is significantly involved in the improved synaptic plasticity found in our preliminary data in db/db mice. However, a lenti-based shRNA (transcript variant 1 cat.#Mm24217, GeneCopoeia, Rockville, Md.) can also be utilized to suppress BDNF expression by administering it into the ICV region. The virus contains a GFP tag and thus can allow determination of the relative infection rate efficiency in the hippocampus.

Memory consolidation and synaptic consolidation refer to protein synthesis-dependent strengthening of synaptic transmission. Furthermore, plastic change results from the alteration of the number of receptors located on a synapse. In diabetic hippocampi, that rosiglitazone (ICV) improves both GluR1 and NR2A expression levels as determined by western analysis.

The development of late LTP, like long term memory, depends on de novo mRNA and protein synthesis. Thus, changes in gene expression can be measured for GluR1, GluR2, NR2A and NR2B by two step qRT-PCR using a syber green mix (Abgene, Thermo Scientific) and referenced with beta-actin. Changes in protein expression can be determined by western analysis from isolate proteins from the hippocampi and referenced with alpha tubulin. Although ANA12 is expected to specifically inhibit BDNF-TrkB activity, the lenti-based ShRNA can also be utilized to prevent BDNF expression as discussed above so levels of transfection can be measured relative to BDNF deletion.

EXAMPLE 20

Effects of Novel Compounds on PPAR Regulation of BDNF

Figure 15B:
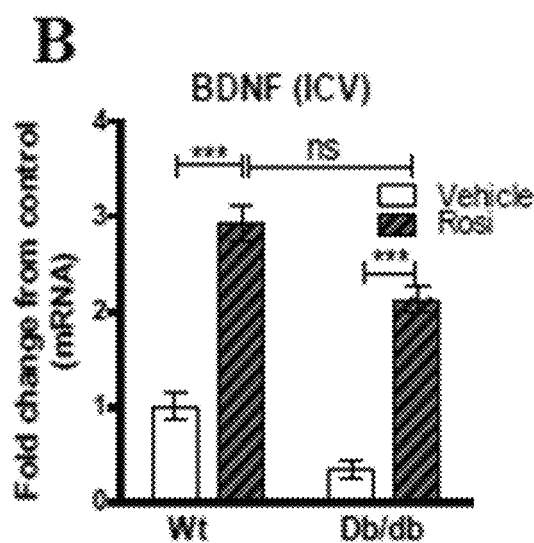
Figure 15C:
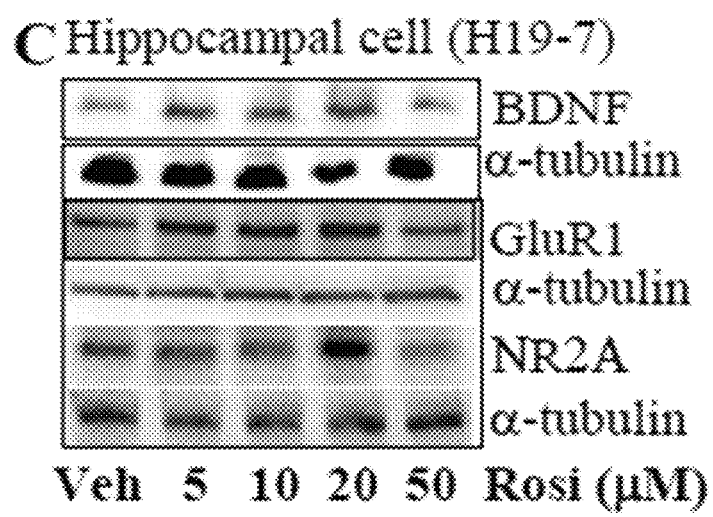
Figure 15D:
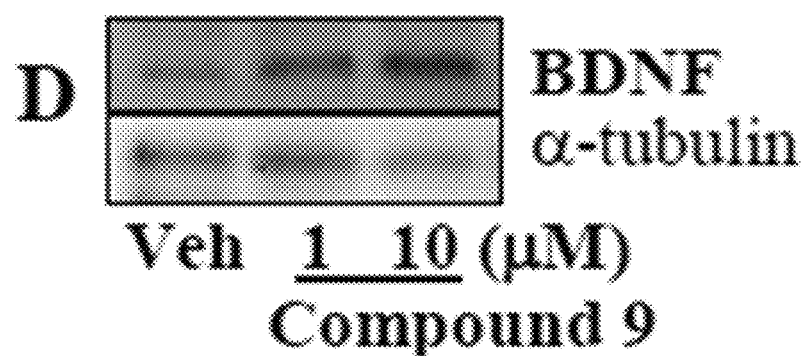
Figure 15E:
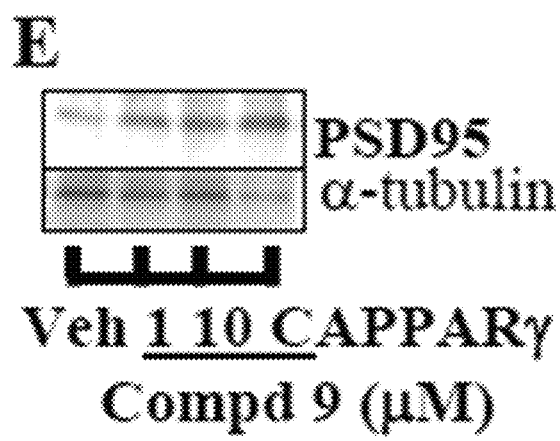
Figure 15F:
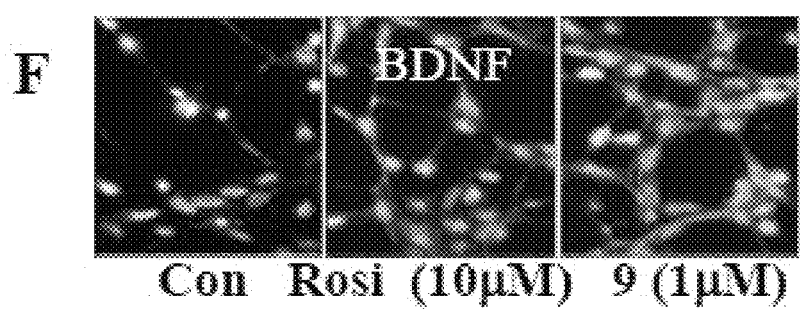
Figure 15G:
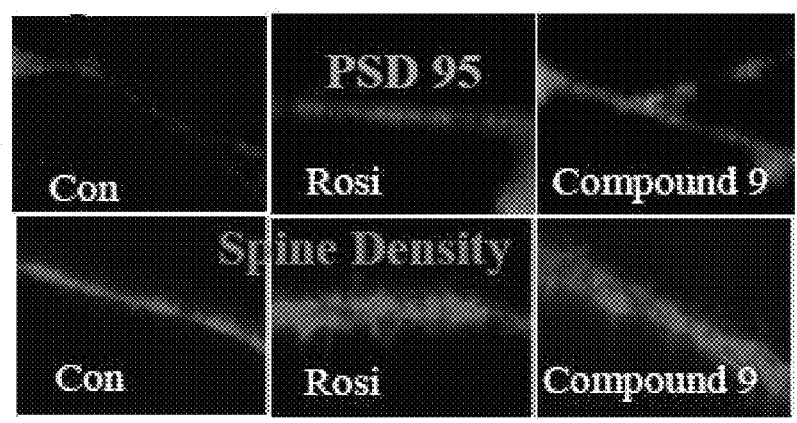

Activation of PPARγ by rosiglitazone (ICV) in wild type and db/db mice has been shown to increase mRNA and protein expression of BDNF (see FIGS. 15B and 15A, respectively). These findings were confirmed in H19-7 cells (see FIG. 15C). Accordingly, the mechanism by which PPARγ regulates the expression of BDNF can be identified, and how PPARγ transcriptionally regulates BDNF. PPARγ is a transcriptional factor that regulates the expression of many genes associated with energy regulation and cell viability.

Figure 16:
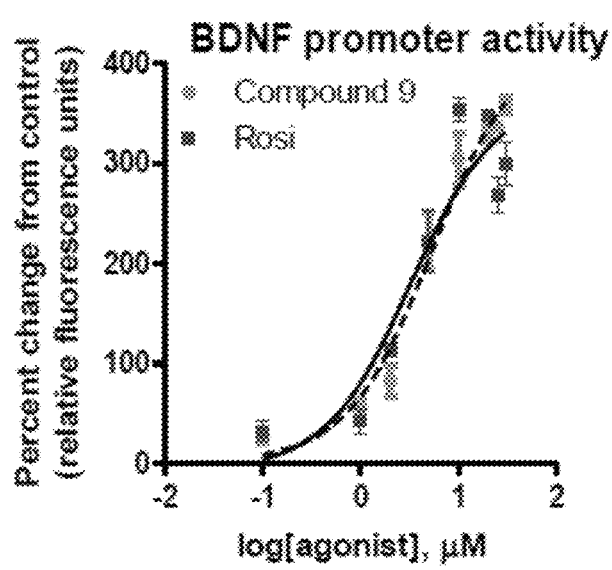
FIG. 16 shows a dose response curve of rosiglitazone and compound 9 inducing BNDF promoter activity in primary hippocampal neuronal cells as determined by luciferase activity standardized to p-Gal.

Nine distinct transcriptional initiation sites exist: eight in the 5' noncoding exon and one preceding coding exon IX, indicating nine different promoters control BDNF transcription sites. Data indicate that activation of PPARγ by rosiglitazone (ICV) in wild type and db/db mice increases mRNA expression of exon IXa (see FIG. 15B). Further, as shown in FIG. 16, PPARγ induces transcription of BDNF. A large fragment of the BDNF DNA containing multiple non-coding as well as the coding region of exon IX has been cloned into a PGL3 vector to confirm that PPARγ transcriptionally regulate BDNF expression.

What is claimed is:

1. A composition comprising a compound selected from the group consisting of

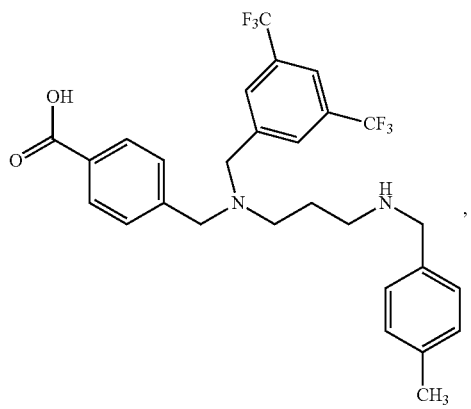

or pharmaceutically acceptable salt thereof.

2. The composition of claim 1, wherein the compound is an agonist of a PPARδ receptor.

3. The composition of claim 2, wherein the compound has a binding affinity for the PPARδ receptor between −10.0 and −12.0 kcal/mol.

4. The composition of claim 2, wherein the compound binds with an amino acid residue of the PPARδ receptor binding pocket, and wherein the amino acid residue is selected from the group consisting of Cys285, Thr288, Thr289, Leu330, Val334, Leu339, Leu353, and Phe368.

5. The composition of claim 4, wherein the binding between the compound and the amino acid residue is a hydrogen bond.

6. The composition of claim 1, wherein the compound is an agonist of a PPARγ receptor.

7. The composition of claim 6, wherein the compound has a binding affinity for the PPARγ receptor between −10.0 and −12.0 kcal/mol.

8. The composition of claim 6, wherein the compound binds with an amino acid residue of the PPARγ receptor binding pocket, and wherein the amino acid residue is selected from the group consisting of Leu228, Cys285, Gln286, Arg288, Ser289, Glu295, Met329, Leu330, Ser342, Glu343, Phe363, and His 449.

9. The composition of claim 8, wherein the binding between the compound and the amino acid residue is a hydrogen bond.

10. The composition of claim 1, wherein the compound is an agonist of a PPARδ receptor and an agonist of a PPARγ receptor.

11. The composition of claim 1, wherein the compound permeates the blood-brain barrier.

12. A pharmaceutical formulation comprising a therapeutically effective amount of a compound selected from the group consisting of

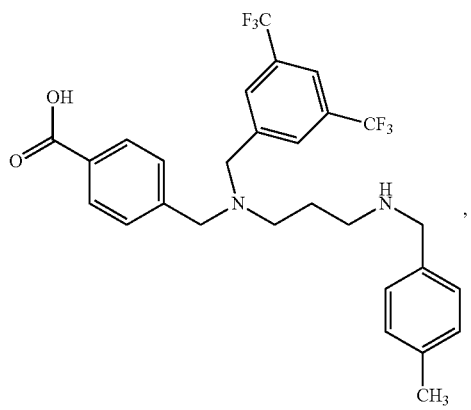

,

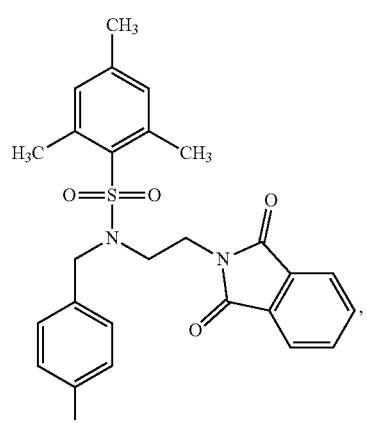

,

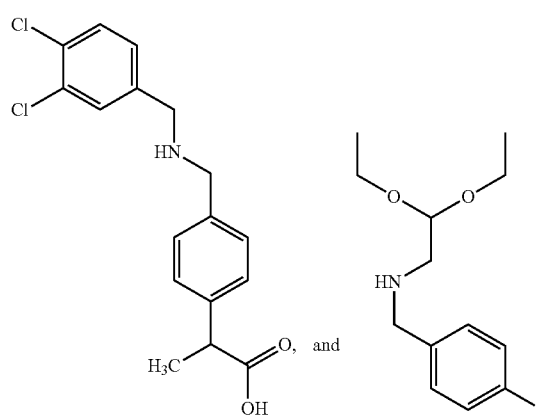

or a pharmaceutically acceptable salt thereof, and one or more pharmaceutically acceptable carriers.

13. The pharmaceutical formulation of claim 12 further comprising at least one additional active ingredient.

14. The pharmaceutical formulation of claim 12, wherein the pharmaceutical formulation is an oral formulation.

15. The pharmaceutical formulation of claim 12, wherein the compound permeates the blood-brain barrier.

16. The composition of claim 1, wherein the compound is

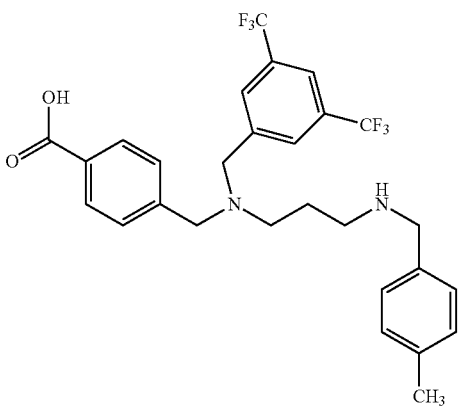

17. The composition of claim 1, wherein the compound is

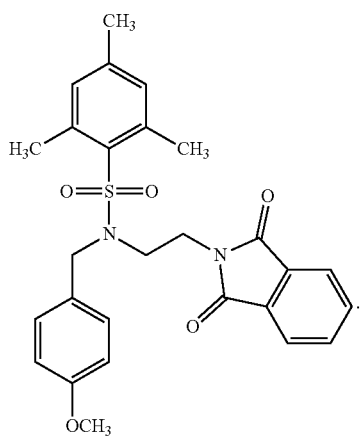 [SMILES: COc1ccc(CN(CCN2C(=O)c3ccccc3C2=O)S(=O)(=O)c2c(C)cc(C)cc2C)cc1]

18. The composition of claim 1, wherein the compound is

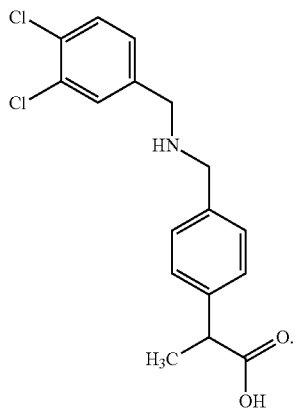 [SMILES: CC(C(=O)O)c1ccc(CNCc2ccc(Cl)c(Cl)c2)cc1]

19. The composition of claim 1, wherein the compound is

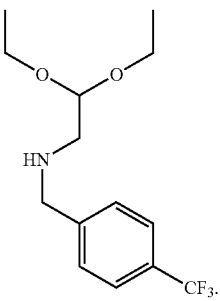 [SMILES: CCOC(CNCc1ccc(C(F)(F)F)cc1)OCC]

* * * * *